United States Patent
Bostick et al.

(10) Patent No.: US 12,065,644 B2
(45) Date of Patent: Aug. 20, 2024

(54) METHODS OF PREPARING NUCLEIC ACID LIBRARIES AND COMPOSITIONS AND KITS FOR PRACTICING THE SAME

(71) Applicant: Takara Bio USA, Inc., Mountain View, CA (US)

(72) Inventors: Magnolia Bostick, San Mateo, CA (US); Ishminder Mann, Milpitas, CA (US); Andrew Alan Farmer, Los Altos, CA (US); Sarah Taylor, Sunnyvale, CA (US)

(73) Assignee: Takara Bio USA, Inc., San Jose, CA (US)

( * ) Notice: Subject to any disclaimer, the term of this patent is extended or adjusted under 35 U.S.C. 154(b) by 22 days.

(21) Appl. No.: 16/465,134

(22) PCT Filed: Feb. 13, 2018

(86) PCT No.: PCT/US2018/018057
§ 371 (c)(1),
(2) Date: May 29, 2019

(87) PCT Pub. No.: WO2018/152129
PCT Pub. Date: Aug. 23, 2018

(65) Prior Publication Data
US 2020/0339978 A1    Oct. 29, 2020

Related U.S. Application Data
(60) Provisional application No. 62/459,858, filed on Feb. 16, 2017.

(51) Int. Cl.
*C12N 15/10* (2006.01)
*C12Q 1/6853* (2018.01)
*C12Q 1/686* (2018.01)

(52) U.S. Cl.
CPC ....... *C12N 15/1086* (2013.01); *C12Q 1/6853* (2013.01); *C12Q 1/686* (2013.01); *C12Q 2521/107* (2013.01); *C12Q 2525/191* (2013.01)

(58) Field of Classification Search
CPC .. C12N 15/1086; C12Q 1/6853; C12Q 1/686; C12Q 2521/107; C12Q 2521/191
See application file for complete search history.

(56) References Cited

U.S. PATENT DOCUMENTS

| | | | |
|---|---|---|---|
| 7,294,712 B2 * | 11/2007 | Hercend et al. | 536/24.5 |
| 9,410,173 B2 * | 8/2016 | Betts et al. | |
| 2014/0113332 A1 | 4/2014 | Betts et al. | |
| 2015/0111789 A1 * | 4/2015 | Betts et al. | C12N 15/1068 |
| 2015/0203906 A1 | 7/2015 | Betts et al. | |
| 2016/0244825 A1 * | 8/2016 | Vigneault | C12Q 1/6869 |
| 2019/0010489 A1 | 1/2019 | Chang et al. | |

FOREIGN PATENT DOCUMENTS

| WO | WO2015057319 A1 | 4/2015 |
| WO | WO2015168161 A2 | 11/2015 |
| WO | WO 2016/174199 A1 * | 11/2016 |

OTHER PUBLICATIONS

Tang et al. "mRNA-seq whole-transcriptome analysis of a single cell." Nat. Methods 6, 377-382 (2009) with Online Methods, two pages (Year: 2009).*
Zajac P, Islam S, Hochgerner H, Lönnerberg P, Linnarsson S (2013) Base Preferences in Non-Templated Nucleotide Incorporation by MMLV-Derived Reverse Transcriptases. Plos One 8(12): e85270 (Year: 2013).*
Watanabe et al., Expression Levels of B Cell Surface Immunoglobulin Regulate Efficiency of Allelic Exclusion and Size of Autoreactive B-1 Cell Compartment, J. Exp. Med., Aug. 16, 1999, vol. 190, No. 4, p. 461-469.
Trombetta et al., Preparation of Single-Cell RNA-Seq Libraries for Next Generation Sequencing, Curr Protoc Mol Biol., May 15, 2001, vol. 107, p. 4.22.1-4.22.17.
Taylor et al., Single-cell T-cell receptor profiling with SMART technology: Workflows for NGS library preparation from single cells isolated in 96-well plates or using the WaferGen ICELL8 Single-Cell System, Takara Bio USA, Inc.
Yaari et al., Practical guidelines for B-cell receptor repertoire sequencing analysis, Genome Medicine, 2015, vol. 7, No. 121, p. 1-14.
Redmond et al., Single-cell TCRseq: paired recovery of entire T-cell alpha and beta chain transcripts in T-cell receptors from single-cell RNAseq, Genome Medicine, 2016, vol. 8, No. 80, p. 1-12.
Mamedov et al., Preparing unbiased T-cell receptor and antibody cDNA libraries for the deep next generation sequencing profiling, Frontiers in Immunology, Dec. 23, 2013, vol. 4, Article 456, p. 1-10.
Macaulay et al., G&T-seq: parallel sequencing of single-cell genomes and transcriptomes, Nature Methods, Jun. 2015, vol. 12, No. 6, p. 519-526.
Han et al., Linking T-cell receptor sequence to functional phenotype at the single-cell level, Nature Biotechnology, Jul. 2014, vol. 32, No. 7, p. 684-695.
Ruggiero et al., High-resolution analysis of the human T-cell receptor repertoire, Nature Communications, Sep. 1, 2015, vol. 6, Article 8081, p. 1-7.

(Continued)

*Primary Examiner* — Nancy J Leith
*Assistant Examiner* — Jessica D Parisi
(74) *Attorney, Agent, or Firm* — Darya C. Cheng; Bret E. Field; Bozicevic, Field & Francis LLP

(57) ABSTRACT

Methods of preparing nucleic acid libraries are provided. Aspects of the methods include producing one or more libraries, including e.g., expression libraries and/or immune cell receptor repertoire libraries, from double stranded complementary DNA (cDNA) generated through a template-switching reaction involving a RNA sample. In some aspects, the methods include preparing a library from a single cell and/or a library indexed at the single cell level. Compositions and kits for use in performing the methods are also provided.

27 Claims, 17 Drawing Sheets

Specification includes a Sequence Listing.

(56) References Cited

OTHER PUBLICATIONS

Han et al., Dietary gluten triggers concomitant activation of CD4+ and CD8+ αβ T cells and γδ T cells in celiac disease, PNAS, Aug. 6, 2013, vol. 110, No. 32, p. 13073-13078.
Banu et al., Building and Optimizing a Virus-specific T Cell Receptor Library for Targeted Immunotherapy in Viral Infections, Scientific Reports, Feb. 25, 2014, vol. 4, No. 4166, p. 1-10.
Bostick et al., cDNA Library Generation for Transcriptome Analysis From Total RNA Equivalent to a Single Cell, Journal of Biomolecular Techniques, May 2013, vol. 24, Supplement, pg. S43.
Liss, Improved quantitative real-time RT-PCR for expression profiling of individual cells, Nucleic Acids Research, Sep. 1, 2002, vol. 30, No. 17, p. 1-9.
Egorov et al., Quantitative profiling of immune repertoires for minor lymphocyte counts using unique molecular identifiers, The Journal of Immunology, May 8, 2015, vol. 194, p. 6155-6163.
Freeman et al., Profiling the T-cell receptor beta-chain repertoire by massively parallel sequencing, Genome Research, Jun. 18, 2009, vol. 19, p. 1817-1824.
Meter et al., A simplified workflow for monoclonal antibody sequencing, PLoS ONE, Jun. 24, 2019, vol. 14, No. 6, p. 9 1-19.
Picelli et al., Full-length RNA-seq from single cells using Smart-seq2, Nature Protocols, Jan. 2, 2014, vol. 9, No. 1, p. 171-181.
Takara Bio USA, Inc., SMARTer(R) Mouse TCR a/b Profiling Kit User Manual, Oct. 2016, p. 1-21.

* cited by examiner

Step 3: Extraction and Clean up

Step 4 (PCR1): TCRα/β GSP PCR

Step 5 (PCR2): Indexed TCRα/β Nested GSP PCR

Off chip

METHODS OF PREPARING NUCLEIC ACID LIBRARIES AND COMPOSITIONS AND KITS FOR PRACTICING THE SAME

CROSS-REFERENCE TO RELATED APPLICATION

Pursuant to 35 U.S.C. § 119(e), this application claims priority to the filing date of U.S. Provisional Patent Application Ser. No. 62/459,858 filed Feb. 16, 2017; the disclosure of which application is incorporated herein by reference.

INCORPORATION BY REFERENCE OF SEQUENCE LISTING PROVIDED AS A TEXT FILE

A Sequence Listing is provided herewith as a text file, "CLON-141_Seq_Listing_as_of_Apr_2020_ST25.txt" created on Apr. 27, 2020, and having a size of 17,025 bytes. The contents of the text file are incorporated by reference herein in their entirety.

INTRODUCTION

The development of next generation sequencing (NGS) technologies has allowed for the rapid extraction of valuable genomic and transcriptomic information from produced nucleic acid libraries. High throughput NGS technologies, such as Illumina (Solexa) sequencing, ROCHE 454 sequencing, Ion torrent (Proton/PGM sequencing) and SOLID sequencing, allow the sequencing of nucleic acid molecules more quickly and cheaply than previously used Sanger sequencing, and as such these techniques have revolutionized biotechnology and biomedical research.

These powerful sequencing technologies place a particular emphasis on library preparation. Well prepared reverse transcribed complementary DNA (cDNA) libraries can be analyzed using NGS technologies for a diverse range of purposes. For example, depending on library preparation methodology, transcriptome data can be utilized to perform differential expression analysis to identify genes that are up or down regulated in certain contexts.

cDNA libraries can also be employed for T cell receptor (TCR) profiling by NGS. The TCR controls the selection, function and activation of T cells and determines which complexes of antigenic peptide-major histocompatibility complex (MHC) the T cell responds to. An individual's TCR repertoire is immensely diverse, due to the derivation of TCR α- and β-chain genes from somatic recombination of variable, diversity and joining (V(D)J) TCR gene segments in each cell. Profiling this diversity of TCRs promotes our understanding of immune repertoire dynamics, advancing our knowledge of the nature of immune response and the pathology of immune disorders. Such insights provide advances in various therapies, including the rapidly advancing field of immuno-oncology.

SUMMARY

Methods of preparing nucleic acid libraries are provided. Aspects of the methods include producing one or more libraries, including e.g., expression libraries and/or immune cell receptor repertoire libraries, from double stranded complementary DNA (cDNA) generated through a template-switching reaction involving a RNA sample. In some aspects, the methods include preparing a library from a single cell and/or a library indexed at the single cell level. Compositions and kits for use in performing the methods are also provided.

BRIEF DESCRIPTION OF THE FIGURES

FIG. 14A shows gene body coverage data with normalized coverage across all genes on the X axis and all mapped exon reads on they Y axis. The figure depicts one example CCRF-CEM cell. FIG. 14B shows a principle component analysis with the mapped reads from the 5'DE library from TALL, CCRF and treated (PMA) CCRF cells (arrows indicating separate groups) as described in FIG. 13.

DEFINITIONS

Figure 1:
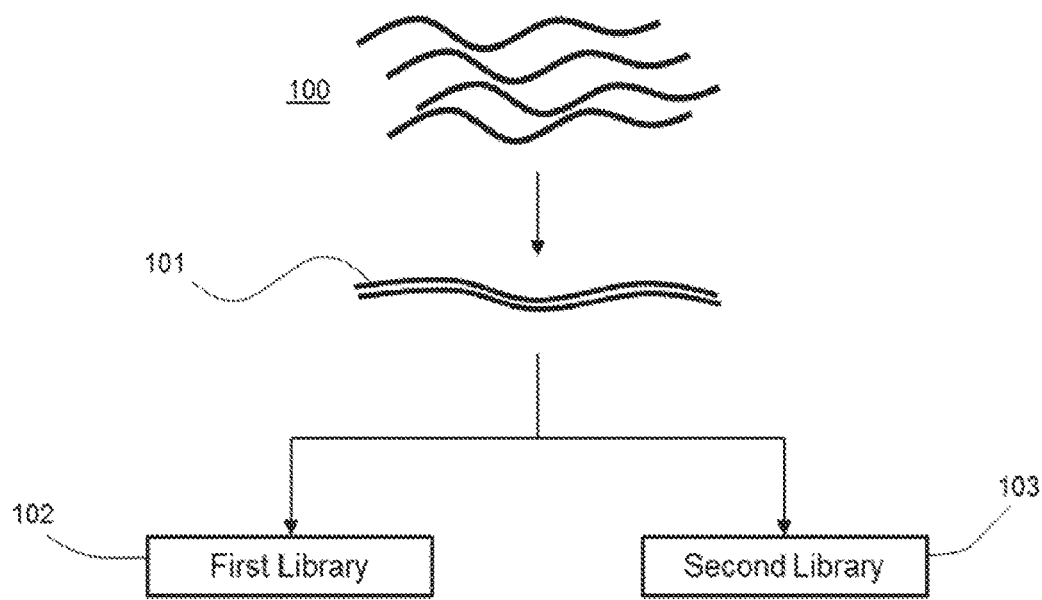
FIG. 1 provides a schematic representation of a method of preparing two nucleic acid libraries from a single RNA sample according to an embodiment of the present disclosure.

As used herein, the term "hybridization conditions" means conditions in which a primer, or other polynucleotide, specifically hybridizes to a region of a target nucleic acid with which the primer or other polynucleotide shares some complementarity. Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The Tm of a duplex may be experimentally determined or predicted using the following formula Tm=81.5+16.6(log 10[Na+])+0.41 (fraction G+C)−(60/N), where N is the chain length and [Na+] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The terms "complementary" and "complementarity" as used herein refer to a nucleotide sequence that base-pairs by non-covalent bonds to all or a region of a target nucleic acid (e.g., a region of the product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%).

The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

A domain refers to a stretch or length of a nucleic acid made up of a plurality of nucleotides, where the stretch or length provides a defined function to the nucleic acid. Examples of domains include Barcoded Unique Molecular Identifier (BUMI) domains, primer binding domains, hybridization domains, barcode domains (such as source barcode domains), unique molecular identifier (UMI) domains, Next Generation Sequencing (NGS) adaptor domains, NGS indexing domains, etc. In some instances, the terms "domain" and "region" may be used interchangeably, including e.g., where immune receptor chain domains/regions are described, such as e.g., immune receptor constant domains/regions. While the length of a given domain may vary, in some instances the length ranges from 2 to 100 nt, such as 5 to 50 nt, e.g., 5 to 30 nt.

DETAILED DESCRIPTION

Methods of preparing nucleic acid libraries are provided. Aspects of the methods include producing one or more libraries, including e.g., expression libraries and/or immune cell receptor repertoire libraries, from double stranded complementary DNA (cDNA) generated through a template-switching reaction involving a RNA sample. In some aspects, the methods include preparing a library from a single cell and/or a library indexed at the single cell level. Compositions and kits for use in performing the methods are also provided.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

Methods

As summarized above, methods of preparing one or more nucleic acid libraries are provided. Single libraries or multiple libraries may be prepared from a single RNA sample. For example, in some instances, a single immune cell receptor repertoire library may be prepared from an RNA sample. In some instances, an expression library and an immune cell receptor repertoire library are prepared from a single RNA sample.

Where the subject methods include preparation of multiple libraries from a single sample the multiple libraries may be prepared sequentially or simultaneously. For example, in some instances the present methods may include simultaneously preparing an expression library and an immune cell receptor repertoire library. By "prepared simultaneously" is meant that one or more library preparation steps (e.g., amplification, end-capturing, etc.) performed in preparing the two or more libraries occur at the same time or at least partially overlap in time. In some instances, the present methods may include sequentially preparing an expression library and an immune cell receptor repertoire library, including e.g., where the expression library is prepared before the immune cell receptor repertoire library or where the immune cell receptor repertoire library is prepared before the expression library. By "prepared sequentially" is meant that that preparation of the two libraries does not overlap in time, e.g., one or more library preparation steps performed in preparing the two libraries do not occur at the same time. In some instances, sequentially prepared libraries may involve the completion of a first library before preparation of the next library is begun. Accordingly, in some instances, simultaneously prepared libraries may involve the preparation of a second library before preparation of a first library is complete.

Figure 2:
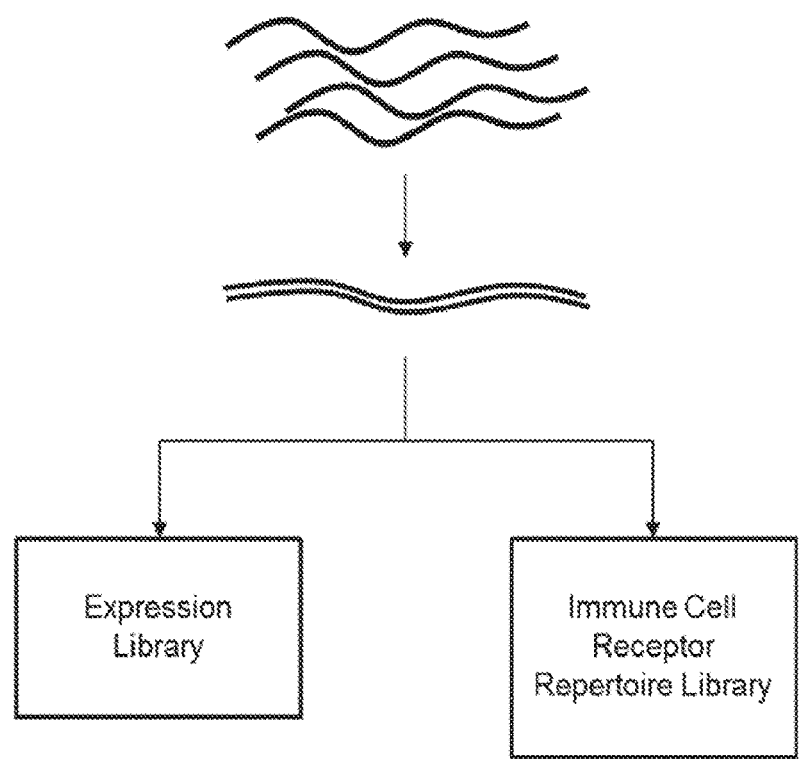
FIG. 2 provides a schematic representation of a method of preparing an expression library and an immune cell receptor repertoire library from a single RNA sample according to an embodiment of the present disclosure.

Whether prepared sequentially or simultaneously, where multiple libraries are prepared from a single RNA sample, the subject methods may include generating a product double stranded cDNA from the RNA sample and subsequently splitting the generated product double stranded cDNA into a first reaction mixture and a second reaction mixture. For example, as schematized in FIG. 1, a RNA sample (100) may be employed in a template switching reaction to generate a double stranded cDNA (101) from the RNA sample. The generated double stranded cDNA, which may or may not be amplified, as desired, may then be split, e.g., into two reactions and subsequently used to generate a first library (102) and a second library (103) as depicted. In some embodiments, the multiple reaction mixtures containing the split double stranded cDNA may be used to generate an expression library (200) and an immune cell receptor repertoire library (201), as depicted in FIG. 2. Accordingly, such split reaction mixtures may be separately employed to generate the multiple libraries as desired, including e.g., where the first reaction mixture is used to generate an expression library and the second reaction mixture is used to generate an immune cell receptor repertoire library.

Splitting of the generated product double stranded cDNA may be performed evenly or unevenly, such that the first and second reaction mixtures may receive an equal or an unequal amount of the generated product double stranded cDNA. For example, in some instances, a reaction mixture employed to generate an expression library may receive more of the split product double stranded cDNA as compared to the amount of the split product double stranded cDNA received by a reaction mixture employed to generate an immune cell receptor repertoire library. In some instances, a reaction mixture employed to generate an expression library may receive less of the split product double stranded cDNA as compared to the amount of the split product double stranded cDNA received by a reaction mixture employed to generate an immune cell receptor repertoire library. In some instances, a reaction mixture employed to generate an expression library may receive the same amount of the split product double stranded cDNA as the amount of the split product double stranded cDNA received by a reaction mixture employed to generate an immune cell receptor repertoire library.

Whereas product double stranded cDNA may be split between two reaction mixtures, as described above, splitting of a product double stranded cDNA is not necessarily limited to splitting between two reaction mixtures and, in some instances, the product double stranded cDNA may be split between more than two reaction mixtures. For example, in some instances, a product double stranded cDNA may be split between three or more reaction mixtures. Splitting of product double stranded cDNA between more than two reaction mixtures may be employed for various purposes including but not limited to e.g., where three or more libraries may be generated from a product double stranded cDNA, including a product double stranded cDNA generated from a single RNA sample.

Any convenient method of splitting generated product double stranded cDNA into different reaction mixtures may be employed in the subject methods. For example, in some instances, product double stranded cDNA may be manually split into reaction mixtures, e.g., by manually pipetting aliquots of the product double stranded cDNA into the reaction mixtures. In some instances, the produce double stranded cDNA may be automatically split into reaction mixtures, e.g., through the use of liquid handling robot or other automated device programmed to dispense aliquots of the product double stranded cDNA into the reaction mixtures. In some instances, the methods may include preamplifying the product double stranded cDNA, e.g., through a preamplification PCR step, prior to splitting into reaction mixtures utilized to generate the individual libraries.

In some instances, individually prepared reaction mixtures may be pooled prior to further processing and, as such, the performed methods may include a pooling step. For example, in some instances, individually prepared product double stranded cDNA may be pooled prior to preparation of one or more libraries. In some instances, a prepared product double stranded cDNA may be pooled prior to splitting the product double stranded cDNA into separate the reactions, e.g., for the preparation of two or more libraries as described above. Reactions individually prepared from separate single RNA samples may be pooled, including e.g., those single RNA samples prepared from a plurality of cells or those prepared from a single cell. Any convenient method of pooling may be employed including e.g., where entire reaction volumes are pooled together or portions of reaction volumes are pooled together. In some instances, individual reactions may be performed in individual containers or wells (e.g., wells of a multi-well plate) and the reaction mixtures of the containers of wells may be pooled into a single container or well.

In some instances, nucleic acids produced in an individual reaction that is subsequently pooled may contain or be modified to contain an identifying nucleic acid sequence that allows for retrospective identification of the individual reaction source of the nucleic acid following pooling. Useful identifying nucleic acid sequences include e.g., barcode nucleic acid sequences and indexing sequences as described in more detail below.

As noted above, product double stranded cDNAs, and subsequently one or more libraries, may be generated from a RNA sample. RNA samples are those that contain one or more types of template RNA, as described in more detail below. RNA samples may be derived from cellular samples including cellular samples that contain a single cell or a population of cells containing, e.g., two or more cells. Cellular samples may be derived from a variety of sources including but not limited to e.g., a cellular tissue, a biopsy, a blood sample, a cell culture, etc. Additionally, cellular samples may be derived from specific organs, tissues, tumors, neoplasms, or the like. Furthermore, cells from any population can be the source of a cellular sample used in the subject methods, such as a population of prokaryotic or eukaryotic single celled organisms including bacteria or yeast. However, where the instant methods include preparing an immune cell receptor repertoire library, eukaryotic cells including mammalian cells will generally be employed as the source of the RNA sample.

As such, in some instances, the source of an RNA sample utilized in the subject methods may be a mammalian cellular sample, such as a rodent (e.g., mouse or rat) cellular sample, a non-human primate cellular sample, a human cellular sample, or the like. In some instances, a mammalian cellular sample may be mammalian blood sample, including but not limited to e.g., a rodent (e.g., mouse or rat) blood sample, a non-human primate blood sample, a human blood sample, or the like.

In some embodiments, useful cellular samples may include those that contain one or more immune cell types. As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses.

In some instances, a RNA sample used in a method described herein will be derived from a population of immune cells, including but not limited to e.g., a mixed population of immune cells, a population of T cells, a population of B cells, or the like. In some instances, a RNA sample used in a method described herein will be derived from a single immune cell, including but not limited to e.g., a single T cell, a single B cell, or the like.

Libraries

As noted above, libraries produced in the subject methods may be produced from a generated product double stranded cDNA. By "product double stranded cDNA" is generally meant a double stranded DNA containing the complement of a template nucleic acid produced from a reverse transcription reaction. A product double stranded cDNA may be produced from a template RNA using a reverse transcription reaction, where any RNA template may be employed including e.g., an mRNA template. Accordingly, the methods provided may include generating a product double stranded cDNA from a template RNA present in an RNA sample through the use of a reverse transcription reaction, such as a template-switching reverse transcription reaction, described in more detail below.

In some instances, the subject methods include preparing a plurality of libraries, e.g., a plurality of expression libraries, a plurality of immune cell receptor repertoire libraries, a combination thereof, or the like, from a plurality of single cells. For example, in some instances, a plurality of individual RNA samples may each be derived from a single cell, including e.g., individual immune cells, and the individual RNA samples may be used in the preparation of product double stranded cDNAs and subsequently utilized to produce a plurality of libraries. Where a plurality of libraries is produced, components used in preparing the libraries (e.g., product double stranded cDNAs) or the libraries themselves may or may not be pooled. As noted above and described in more detail below, where libraries or library preparation components are pooled the nucleic acids may include non-templated identifying nucleic acid sequences that may be utilized in retrospectively identifying the source of a particular library component or sequence thereof. Such retrospective identification may be achieved, e.g., through demultiplexing.

In some embodiments, aspects of the present methods include preparing an expression library. By "expression library" is meant a nucleic acid library useful in evaluating nucleic acid expression of a cellular sample, including e.g., a single cell sample or a sample containing a population of cells. Preparation of expression libraries may include preparing the expression library for next generation sequencing (NGS), including where the NGS expression library is prepared from a RNA sample.

NGS libraries produced as described herein are those whose nucleic acid members include a partial or complete sequencing platform adapter sequence at their termini useful for sequencing using a sequencing platform of interest. Sequencing platforms of interest include, but are not limited to, the HiSeq™, MiSeq™ and Genome Analyzer™ sequencing systems from Illumina®; the Ion PGM™ and Ion Proton™ sequencing systems from Ion Torrent™; the PACBIO RS II Sequel system from Pacific Biosciences, the SOLID sequencing systems from Life Technologies™, the 454 GS FLX+ and GS Junior sequencing systems from ROCHE, the MinION™ system from Oxford Nanopore, or any other sequencing platform of interest.

As described above, the methods of the present disclosure include generating a product double stranded cDNA from an RNA sample, where the produced product double stranded cDNA may be split into two or more reaction mixtures, one of which may be employed to prepare an expression library. A prepared expression library may be a full length expression library or a non-full length expression library. By "full length expression library" is meant that the nucleic acid members of the library contain full length cDNA sequences that correspond to the full length RNA members from which they were reverse transcribed. For example, where an individual library member is a full length cDNA of an mRNA, the full length cDNA will include the entire coding sequence of the mRNA, e.g., the entire spliced mRNA coding sequence, i.e., the entire mRNA coding sequence between the 5'-cap and the poly(A) tail of the mRNA. A full-length cDNA may or may not include sequence corresponding to one or more untranslated regions (UTR) of an mRNA, e.g., a 3' UTR or a 5' UTR.

A prepared expression library may, in some instances, be a library specifically prepared to capture the ends of the subject RNA molecules. Such libraries may be referred to herein as an "end-captured" library or the members thereof may be referred to as end-captured nucleic acids. End-captured libraries include nucleic acids separately subjected to 3' end capture or 5' end capture methods and where the nucleic acids are subjected to both 3' and 5' end capture methods. End-capture methods may make use of an end amplification primer. As used herein, the term "end amplification primer" generally refers to a nucleic acid primer used in a PCR reaction to amplify from an end introduced in a double stranded DNA to be amplified. The end introduced into a double stranded DNA to which an end amplification primer binds is generally not an original end of the double stranded DNA (e.g., not an original 5' end, e.g., corresponding to an original 5' end of a reverse transcribed RNA or not an original 3' end, e.g., corresponding to an original 3' end of a reverse transcribed RNA) and may be a newly introduced end, e.g., an end generated as a product of a fragmentation and/or ligation reaction.

Accordingly, in certain embodiments, the methods of preparing expression libraries are end-capture methods.

End-capture methods may be employed for sequencing and/or quantifying RNA (e.g., mRNA transcripts), e.g., for differential expression analysis. End-capture methods may make use of a tagmentation reaction, where a subject double stranded DNA is fragmented and the produced fragments are ligated to desired oligonucleotides containing synthetic sequences, such as e.g., one or more of the non-templated sequences described herein. Tagmentation may be achieved through the use of transposase that mediates the fragmentation and ligation.

In certain embodiments, the end-capture method captures the 3' ends of RNAs, e.g., where end-capture is facilitated by the presence of an amplification primer binding site in the first strand cDNA primer and a 5' post-tagmentation PCR primer binding site introduced by tagmentation. In other embodiments, the end-capture methods capture the 5' ends of RNAs, e.g., where end-capture is facilitated by the presence of an amplification primer binding site in the template switch oligonucleotide and a 3' post-tagmentation PCR primer binding site introduced by tagmentation.

Figure 4:
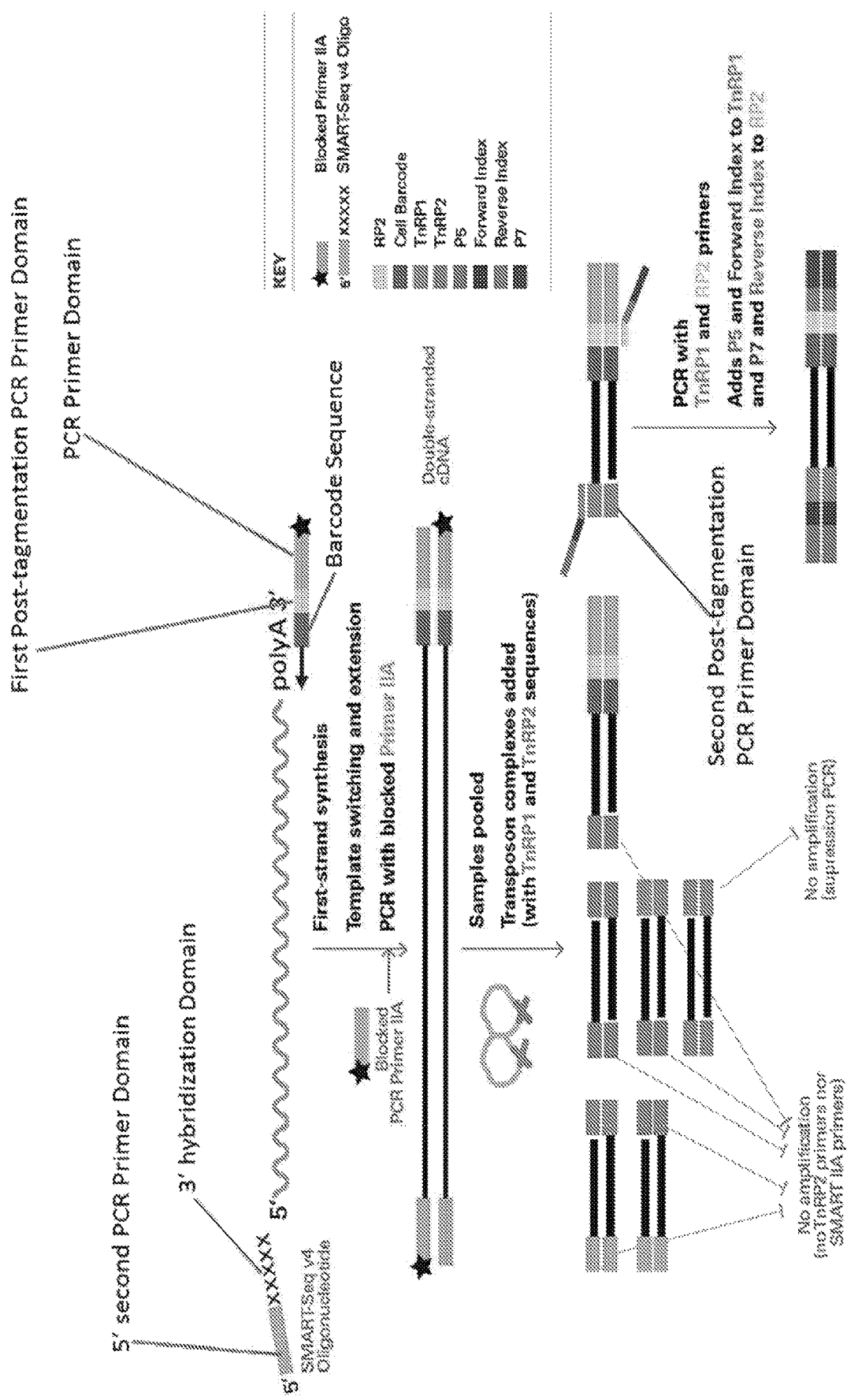
FIG. 4 provides an example of the use of tagmentation in a library preparation method that may be adapted for use in the methods of the present disclosure.

An example of an end-capture expression library preparation method is schematically illustrated in FIG. 4. The method includes combining a RNA sample, a first strand cDNA primer including a PCR primer binding domain, a template switch oligonucleotide including a 3' hybridization domain and a 5' second PCR primer binding domain, a reverse transcriptase (not shown), and dNTPs (not shown), in a reaction mixture under conditions sufficient to produce a double stranded product nucleic acid (not shown) including a template mRNA and the template switch oligonucleotide each hybridized to adjacent regions of a first strand cDNA. In this example, the RNA sample includes an mRNA (polyA+) template, and the first strand cDNA primer includes an oligo-dT 3' hybridization domain, a barcode, a sequencing adapter domain (here, an Illumina® Read Primer 2 sequence), a first PCR primer binding domain (here, a domain that binds the Clontech® Primer IIA), and a blocking modification (black star). During first strand synthesis, the reverse transcriptase template switches from the template mRNA to a template switch oligonucleotide (in this example, the Clontech SMART-SEQ v4 template switch oligonucleotide) that includes a 3' hybridization domain that includes an LNA and a 5' domain including a second PCR primer binding domain. In this example, the second PCR primer binding domain (a domain that binds the Clontech® Primer IIA) is the same as the first PCR primer binding domain. After first-strand synthesis, the cDNA is PCR amplified using a blocked Clontech® Primer IIA to generate product double stranded cDNA (labeled "Double-stranded cDNA" in FIG. 4).

In the example shown in FIG. 4, the production of the product double stranded cDNA is depicted for reference to facilitate identification of the primer binding domains and barcode sequences utilized in downstream amplification and sequencing. As described in more detail below, tagmentation employed in the methods provided may differ in the presence, absence and location of various elements (e.g., non-templated sequences) as compared to that depicted in FIG. 4. For example, while the schematic of FIG. 4 depicts 3' end capture, the components of the various steps of the method may be readily reconfigured for 5' end capture. In addition, as described above, the methods provided may generally include the generation of the product double stranded cDNA and subsequent splitting of produced double stranded cDNA between reaction mixtures prior to tagmentation. Further description of the production of libraries that involve a tagmentation reaction are provided in International Application No. PCT/US2016/051989; the disclosure of which is incorporated herein by reference in its entirety.

The expression libraries produced may exhibit a desired complexity (e.g., high complexity). The "complexity" of an expression library relates to the proportion of redundant sequencing reads (e.g., sharing identical start sites) obtained upon sequencing the library. Complexity is inversely related to the proportion of redundant sequencing reads. In a low complexity library, certain target sequences are over-represented, while other targets (e.g., mRNAs expressed at low levels) suffer from little or no coverage. In a high complexity library, the sequencing reads more closely track the known distribution of target nucleic acids in the starting nucleic acid sample, and will include coverage, e.g., for targets known to be present at relatively low levels in the starting sample (e.g., mRNAs expressed at low levels). According to certain embodiments, the complexity of an expression library produced according to the methods provided is such that sequencing reads are produced for 70% or more, 75% or more, 80% or more, 85% or more, 90% or more, 95% or more, 96% or more, 97% or more, 98% or more, or 99% or more of the different species of target nucleic acids (e.g., different species of mRNAs) in the starting nucleic acid sample (e.g., RNA sample). The complexity of a library may be determined by mapping the sequencing reads to a reference genome or transcriptome (e.g. for a particular cell type). Specific approaches for determining the complexity of sequencing libraries have been developed, including the approach described in Daley et al. (2013) *Nature Methods* 10(4):325-327.

In certain embodiments, the methods provided further include subjecting a prepared expression library to an NGS protocol. The protocol may be carried out on any suitable NGS sequencing platform. NGS sequencing platforms of interest include, but are not limited to, a sequencing platform provided by Illumina® (e.g., the HiSeq™, MiSeq™ and/or NextSeq™ sequencing systems); Ion Torrent™ (e.g., the Ion PGM™ and/or Ion Proton™ sequencing systems); Pacific Biosciences (e.g., the PACBIO RS II Sequel sequencing system); Life Technologies™ (e.g., a SOLID sequencing system); ROCHE (e.g., the 454 GS FLX+ and/or GS Junior sequencing systems); or any other sequencing platform of interest. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS sequencing system employed.

In certain embodiments, the subject methods may be used to generate an expression library corresponding to mRNAs for downstream sequencing on a sequencing platform of interest (e.g., a sequencing platform provided by Illumina®, Ion Torrent™, Pacific Biosciences, Life Technologies™, Roche, or the like). According to certain embodiments, the subject methods may be used to generate a NGS library corresponding to non-polyadenylated RNAs for downstream sequencing on a sequencing platform of interest. For example, microRNAs may be polyadenylated and then used as templates in a template switch polymerization reaction as described elsewhere herein. Random or gene-specific priming may also be used, depending on the goal of the researcher. The library may be mixed 50:50 with a control library (e.g., Illumina®'s PhiX control library) and sequenced on the sequencing platform (e.g., an Illumina® sequencing system). The control library sequences may be removed and the remaining sequences mapped to the transcriptome of the source of the mRNAs (e.g., human, mouse, or any other mRNA source).

A prepared expression library may be utilized in various downstream analyses and, in some instances the preparation of the library may be specifically reconfigured for a desired type of downstream analysis. For example, in some instances, a prepared expression library may be subjected to whole transcriptome analysis (WTA) that includes analysis of mRNA as well as non-mRNA RNA species such as non-coding RNA (e.g., snRNA and snoRNA). Therefore, in some instances, library preparation may be specifically configured to allow for analysis of non-mRNA RNAs within the transcriptome, e.g., by utilizing primers that do not rely on hybridization to the poly(A) tail (e.g., random primers) or by the addition of a tailing reaction, e.g., by adding a poly(A) tail to RNA species that are not naturally polyadenylated prior to production of product double stranded cDNA.

In some instances, preparation of a library, e.g., a library for WTA, may include a step of reducing the amount of ribosomal RNAs within the sample and/or library. Any convenient method of reducing and/or removing unwanted ribosomal RNAs may be employed for selective removal, including e.g., using affinity purification, degradation of the contaminating nucleic acid (e.g., using a RiboGone™ (Takara Bio USA Inc., Mountain View, CA) and those methods described in U.S. Pat. No. 9,428,794 and U.S. Patent Application Pub. No. US 2015/0225773 A1; the disclosures of which are incorporated herein by reference in their entirety), combinations thereof, and the like.

In certain embodiments, a prepared expression library may be utilized in a differential expression analysis, including e.g., where the relative expression (i.e., the up or down regulation) of one or more genes is determined. Differential expression may be qualitatively or quantitatively determined and such analyses may be transcriptome wide or may be targeted. As such, the number of expressed transcripts evaluated in a subject differential expression analysis will vary. In some instances, a differential expression analysis may evaluate 50% or more of the expressed transcripts in a subject genome, including but not limited to e.g., 60% or more, 70% or more, 80% or more, 90% or more 95% or more, 99% or more, or essentially all the expressed transcripts of the subject genome. Targeted differential expression analyses may include analysis of only a subset or a particular category of transcripts. Transcript categories to which a targeted expression analysis may be limited will vary and may include but not be limited to e.g., immune gene transcripts.

Useful categories and subcategories of immune genes generally include those groups of genes responsible for functioning of the immune system and the successful defense against pathogens, including but not limited to e.g., those genes associated with immune system process (such as the genes identified by gene ontology (GO) accession number GO:0002376 (available online at geneontology(dot)org) including but not limited to e.g., those genes associated with B cell mediated immunity, B cell selection, T cell mediated immunity, T cell selection, activation of immune response, antigen processing and presentation, antigen sampling in mucosal-associated lymphoid tissue, basophil mediated immunity, eosinophil mediated immunity, hemocyte differentiation, hemocyte proliferation, immune effector process, immune response, immune system development, immunological memory process, leukocyte activation, leukocyte homeostasis, leukocyte mediated immunity, leukocyte migration, lymphocyte costimulation, lymphocyte mediated immunity, mast cell mediated immunity, myeloid cell homeostasis, myeloid leukocyte mediated immunity, natural killer cell mediated immunity, negative regulation of immune system process, neutrophil mediated immunity, positive regulation of immune system process, production of molecular mediator of immune response, regulation of immune system process, somatic diversification of immune receptors, tolerance induction, and the like. Specific genes of interest include, but are not limited to: cytokines, interleukins, interleukin receptors, CD4, CD8, CD3, PD-1, etc.

As summarized above, in some embodiments the present methods include preparing an immune cell receptor repertoire library from an RNA sample. Aspects of the subject methods include amplifying an immune cell-specific cDNA from a product double stranded cDNA generated from a RNA sample to produce an immune cell receptor repertoire library. By "immune cell receptor repertoire library" is generally meant a nucleic acid library that includes full length or partial sequences of one or more types of immune receptors of a cell or a population of cells. For example, an immune cell receptor repertoire library may be generated for a single cell or for a population of cells derived from a single cellular sample or a single subject or a population of cellular samples, including e.g., a population of samples from two or more subjects. In some instances, a subject library may be generated from individual singlecells which, following the addition of an identifying nucleic acid sequence, may be pooled.

As noted above, the members of an immune cell receptor repertoire library may vary in length and may be full length or less than full length. In some instances, the members of the library will preferentially include the 5' end of an immune cell receptor. Immune cell receptors of interest include but are not limited to e.g., the T-cell receptor (TCR) and the B-cell receptor (BCR).

In some instances, an immune cell receptor repertoire library may include a TCR repertoire library. The TCR complex is a disulfide-linked membrane-anchored heterodimeric protein normally expressed on the surface of T cells and consisting of the highly variable alpha (α) and beta (β) chains expressed as part of a complex with CD3 chain molecules. Many native TCRs exist in heterodimeric αβ or γδ forms. The complete endogenous TCR complex in heterodimeric αβ form includes eight chains, namely an alpha chain (referred to herein as TCRα or TCR alpha), beta chain (referred to herein as TCRβ or TCR beta), delta chain, gamma chain, two epsilon chains and two zeta chains. The alpha and beta TCR chains include variable (V) and constant (C) regions. TCR diversity is generated from genetic recombination (VJ recombination of alpha chains and VDJ recombination of beta chains) resulting in areas of intersection that are important for antigen (i.e., peptide/MHC) recognition.

In some instances, a TCR repertoire library may include TCR-α chain sequences, TCR-β chain sequences, or both TCR-α chain sequences and TCR-β chain sequences. TCR chain sequences of a subject TCR repertoire library may include full length TCR chain sequences (e.g., full length TCR alpha chain sequences, full length TCR beta chain sequences) or partial TCR chain sequences (e.g., partial length TCR alpha chain sequences, partial length TCR beta chain sequences).

Where the subject TCR repertoire library members include partial TCR chain sequences, the partial TCR chain sequences may include the entire or essentially the entire TCR chain variable region (e.g., the TCR alpha chain variable region, the TCR beta chain variable region). In some instances, the resulting library members include the TCR variable region and at least a portion of the TCR constant region. In some instances, the resulting library members include sequence corresponding to the TCR alpha and/or beta chain 5' mRNA ends. In some instances, the resulting library members include sequence from the TCR alpha or beta chain 5' end to at least a portion of the corresponding chain constant region.

In certain embodiments, preparation of the immune cell-specific library may include TCR specific amplification. Such TCR specific amplification may make use of a TCR specific primer. By "TCR specific primer" is meant a primer that specifically hybridizes to a region of a TCR chain (e.g., a TCR alpha chain, a TCR beta chain) nucleic acid sequence or the complement thereof. In some instances, a TCR specific primer may hybridize to only one type of TCR chain, e.g., only a TCR alpha chain or only a TCR beta chain. In some instances, a TCR specific primer may be configured to hybridize to more than one type of TCR chain, e.g., configured to hybridize to both a TCR alpha chain and a TCR beta chain.

TCR specific primers may be designed to specifically hybridize to a TCR alpha chain constant region or the complement thereof. For example, in some instances, a TCR specific primer may hybridize to a mammalian TCR alpha chain constant region or a complement thereof, including e.g., a human TCR alpha chain constant region, a mouse TCR alpha chain constant region, or the like.

An exemplary human TCR alpha chain constant region has the following amino acid sequence:

```
                                    (SEQ ID NO: 01)
PNIQNPDPAVYQLRDSKSSDKSVCLFTDFDSQTNVSQSKDSDVYITDKTV

LDMRSMDFKSNSAVAWSNKSDFACANAFNNSIIPEDTFFPSPESSCDVKL

VEKSFETDTNLNFQNLSVIGFRILLLKVAGFNLLMTLRLWSS,
``` which is encoded by the following nucleic acid sequence:

```
(SEQ ID NO: 02; T-cell receptor alpha chain C
region, human; GenBank: AY247834.1, AAO72258.1;
UniProtKB: P01848)
CCAAATATCCAGAACCCTGACCCTGCCGTGTACCAGCTGAGAGACTCTAA

ATCCAGTGACAAGTCTGTCTGCCTATTCACCGATTTTGATTCTCAAACAA

ATGTGTCACAAAGTAAGGATTCTGATGTGTATATCACAGACAAAACTGTG

CTAGACATGAGGTCTATGGACTTCAAGAGCAACAGTGCTGTGGCCTGGAG

CAACAAATCTGACTTTGCATGTGCAAACGCCTTCAACAACAGCATTATTC

CAGAAGACACCTTCTTCCCCAGCCCAGAAAGTTCCTGTGATGTCAAGCTG

GTCGAGAAAAGCTTTGAAACAGATACGAACCTAAACTTTCAAAACCTGTC

AGTGATTGGGTTCCGAATCCTCCTCCTGAAAGTGGCCGGGTTTAATCTGC

TCATGACGCTGCGGCTGTGGTCCAGCTGA.
```

An exemplary mouse TCR alpha chain constant region has the following amino acid sequence:

```
(SEQ ID NO: 03; UniProtKB: P01849)
PYIQNPEPAVYQLKDPRSQDSTLCLFTDFDSQINVPKTMESGTFITDKTV

LDMKAMDSKSNGAIAWSNQTSFTCQDIFKETNATYPSSDVPCDATLTEKS

FETDMNLNFQNLSVMGLRILLLKVAGFNLLMTLRLWSS
or
```

(SEQ ID NO: 04; GenBank: AAA53226.1)
PNIQNPEPAVYQLKDPRSQDSTLCLFTDFDSQINVPKTMESGTFITDKTV

LDMKAMDSKSNGAIAWSNQTSFTCQDIFKETNATYPSSDVPCDATLTEKS

FETDMNLNFQNLSVMGLRILLLKVAGFNLLMTLRLWSS which are encoded by the following nucleic acid sequences, respectively:

(SEQ ID NO: 05)
CCATACATCCAGAACCCAGAACCTGCTGTGTACCAGTTAAAAGATCCTCG

GTCTCAGGACAGCACCCTCTGCCTGTTCACCGACTTTGACTCCCAAATCA

ATGTGCCGAAAACCATGGAATCTGGAACGTTCATCACTGACAAAACTGTG

CTGGACATGAAAGCTATGGATTCCAAGAGCAATGGGGCCATTGCCTGGAG

CAACCAGACAAGCTTCACCTGCCAAGATATCTTCAAAGAGACCAACGCCA

CCTACCCCAGTTCAGACGTTCCCTGTGATGCCACGTTGACCGAGAAAAGC

TTTGAAACAGATATGAACCTAAACTTTCAAAACCTGTCAGTTATGGGACT

CCGAATCCTCCTGCTGAAAGTAGCGGGATTTAACCTGCTCATGACGCTGA

GGCTGTGGTCCAGT, (SEQ ID NO: 06; GenBank: U07662.1)
CCAAACATCCAGAACCCAGAACCTGCTGTGTACCAGTTAAAAGATCCTCG

GTCTCAGGACAGCACCCTCTGCCTGTTCACCGACTTTGACTCCCAAATCA

ATGTGCCGAAAACCATGGAATCTGGAACGTTCATCACTGACAAAACTGTG

CTGGACATGAAAGCTATGGATTCCAAGAGCAATGGGGCCATTGCCTGGAG

CAACCAGACAAGCTTCACCTGCCAAGATATCTTCAAAGAGACCAACGCCA

CCTACCCCAGTTCAGACGTTCCCTGTGATGCCACGTTGACCGAGAAAAGC

TTTGAAACAGATATGAACCTAAACTTTCAAAACCTGTCAGTTATGGGACT

CCGAATCCTCCTGCTGAAAGTAGCGGGATTTAACCTGCTCATGACGCTGA

GGCTGTGGTCCAGT.

TCR specific primers may be designed to specifically hybridize to a TCR beta chain (e.g., a TCR beta 1 chain constant region or a TCR beta 2 chain constant region) constant region or the complement thereof. For example, in some instances, a TCR specific primer may hybridize to a mammalian TCR beta chain constant region or a complement thereof, including e.g., a human TCR beta chain constant region, a mouse TCR beta chain constant region, or the like.

An exemplary human TCR beta chain 1 constant region has the following amino acid sequence:

(SEQ ID NO: 07); UniProtKB: P01850;
GenBank: CAA25134.1)
EDLNKVFPPEVAVFEPSEAEISHTQKATLVCLATGFFPDHVELSWWVNG

KEVHSGVSTDPQPLKEQPALNDSRYCLSSRLRVSATFWQNPRNHFRCQVQ

FYGLSENDEWTQDRAKPVTQIVSAEAWGRADCGFTSVSYQQGVLSATIL

YEILLGKATLYAVLVSALVLMAMVKRKDF which is encoded by the following nucleic acid sequence:

(SEQ ID NO: 08; GenBank: EF101778.1, X00437.1)
GAGGACCTGAACAAGGTGTTCCCACCCGAGGTCGCTGTGTTTGAGCCATC

AGAAGCAGAGATCTCCCACACCCAAAAGGCCACACTGGTGTGCCTGGCCA

CAGGCTTCTTCCCCGACCACGTGGAGCTGAGCTGGTGGGTGAATGGGAAG

GAGGTGCACAGTGGGGTCAGCACAGACCCGCAGCCCCTCAAGGAGCAGCC

CGCCCTCAATGACTCCAGATACTGCCTGAGCAGCCGCCTGAGGGTCTCGG

CCACCTTCTGGCAGAACCCCCGCAACCACTTCCGCTGTCAAGTCCAGTTC

TACGGGCTCTCGGAGAATGACGAGTGGACCCAGGATAGGGCCAAACCCGT

CACCCAGATCGTCAGCGCCGAGGCCTGGGGTAGAGCAGACTGTGGCTTTA

CCTCGGTGTCCTACCAGCAAGGGGTCCTGTCTGCCACCATCCTCTATGAG

ATCCTGCTAGGGAAGGCCACCCTGTATGCTGTGCTGGTCAGCGCCCTTGT

GTTGATGGCCATGGTCAAGAGAAAGGATTTC.

An exemplary human TCR beta chain 2 constant region has the following amino acid sequence:

(SEQ ID NO: 09; UniProtKB: A0A5B9,
GenBank: AAA60662.1)
DLKNVFPPEVAVFEPSEAEISHTQKATLVCLATGFYPDHVELSWWVNGKE

VHSGVSTDPQPLKEQPALNDSRYCLSSRLRVSATFWQNPRNHFRCQVQFY

GLSENDEWTQDRAKPVTQIVSAEAWGRADCGFTSESYQQGVLSATILYEI

LLGKATLYAVLVSALVLMAMVKRKDSRG which is encoded by the following nucleic acid sequence:

(SEQ ID NO: 10; GenBank: L34740.1)
GACCTGAAAAACGTGTTCCCACCCGAGGTCGCTGTGTTTGAGCCATCAGA

AGCAGAGATCTCCCACACCCAAAAGGCCACACTGGTATGCCTGGCCACAG

GCTTCTACCCCGACCACGTGGAGCTGAGCTGGTGGGTGAATGGGAAGGAG

GTGCACAGTGGGGTCAGCACAGACCCGCAGCCCCTCAAGGAGCAGCCCGC

CCTCAATGACTCCAGATACTGCCTGAGCAGCCGCCTGAGGGTCTCGGCCA

CCTTCTGGCAGAACCCCCGCAACCACTTCCGCTGTCAAGTCCAGTTCTAC

GGGCTCTCGGAGAATGACGAGTGGACCCAGGATAGGGCCAAACCCGTCAC

CCAGATCGTCAGCGCCGAGGCCTGGGGTAGAGCAGACTGTGGCTTCACCT

CCGAGTCTTACCAGCAAGGGGTCCTGTCTGCCACCATCCTCTATGAGATC

TTGCTAGGGAAGGCCACCTTGTATGCCGTGCTGGTCAGTGCCCTCGTGCT

GATGGCCATGGTCAAGAGAAAGGATTCCAGAGGCTAG.

An exemplary mouse TCR beta chain 1 constant region has the following amino acid sequence:

(SEQ ID NO: 11; UniProtKB: P01852)
EDLRNVTPPKVSLFEPSKAEIANKQKATLVCLARGFFPDHVELSWWVNGK

EVHSGVSTDPQAYKESNYSYCLSSRLRVSATFWHNPRNHFRCQVQFHGLS

EEDKWPEGSPKPVTQNISAEAWGRADCGITSASYQQGVLSATILYEILLG

KATLYAVLVSTLVVMAMVKRKNS which is encoded by the following nucleic acid sequence:

(SEQ ID NO: 12; GenBank: FJ188408.1)
GAGGATCTGAGAAATGTGACTCCACCCAAGGTCTCCTTGTTTGAGCCATC

AAAAGCAGAGATTGCAAACAAACAAAAGGCTACCCTCGTGTGCTTGGCCA

GGGGCTTCTTCCCTGACCACGTGGAGCTGAGCTGGTGGGTGAATGGCAAG

GAGGTCCACAGTGGGGTCAGCACGGACCCTCAGGCCTACAAGGAGAGCAA

TTATAGCTACTGCCTGAGCAGCCGCCTGAGGGTCTCTGCTACCTTCTGGC

ACAATCCTCGCAACCACTTCCGCTGCCAAGTGCAGTTCCATGGGCTTTCA

GAGGAGGACAAGTGGCCAGAGGGCTCACCCAAACCTGTCACACAGAACAT

CAGTGCAGAGGCCTGGGGCCGAGCAGACTGTGGGATTACCTCAGCATCCT

ATCAACAAGGGGTCTTGTCTGCCACCATCCTCTATGAGATCCTGCTAGGG

AAAGCCACCCTGTATGCTGTGCTTGTCAGTACACTGGTGGTGATGGCTAT

GGTCAAAAGAAAGAATTCATGA.

An exemplary mouse TCR beta chain 2 constant region has the following amino acid sequence:

(SEQ ID NO: 13; UniProtKB: P01851)
EDLRNVTPPKVSLFEPSKAEIANKQKATLVCLARGFFPDHVELSWWVNGK

EVHSGVSTDPQAYKESNYSYCLSSRLRVSATFWHNPRNHFRCQVQFHGLS

EEDKWPEGSPKPVTQNISAEAWGRADCGITSASYHQGVLSATILYEILLG

KATLYAVLVSGLVLMAMVKKKNS which is encoded by the following nucleic acid sequence:

(SEQ ID NO: 14; GenBank: U46841.1)
GAGGATCTGAGAAATGTGACTCCACCCAAGGTCTCCTTGTTTGAGCCATC

AAAAGCAGAGATTGCAAACAAACAAAAGGCTACCCTCGTGTGCTTGGCCA

GGGGCTTCTTCCCTGACCACGTGGAGCTGAGCTGGTGGGTGAATGGCAAG

GAGGTCCACAGTGGGGTCAGCACGGACCCTCAGGCCTACAAGGAGAGCAA

TTATAGCTACTGCCTGAGCAGCCGCCTGAGGGTCTCTGCTACCTTCTGGC

ACAATCCTCGAAACCACTTCCGCTGCCAAGTGCAGTTCCATGGGCTTTCA

GAGGAGGACAAGTGGCCAGAGGGCTCACCCAAACCTGTCACACAGAACAT

CAGTGCAGAGGCCTGGGGCCGAGCAGACTGTGGAATCACTTCAGCATCCT

ATCATCAGGGGTTCTGTCTGCAACCATCCTCTATGAGATCCTACTGGGG

AAGGCCACCCTATATGCTGTGCTGGTCAGTGGCCTGGTGCTGATGGCCAT

GGTCAAGAAAAAAAATTCCTGA.

In some instances, an immune cell receptor repertoire library may include a BCR repertoire library. The BCR complex is found on the surface of B cells and includes a membrane bound immunoglobulin (i.e., antibody) binding moiety, which includes a heavy and a light chain, each of which contains a constant (C) and a variable (V) region. The immunoglobulin chain of the BCR is bound by disulfide bridges to a signal transducing CD79A/B chains. The immunoglobulin chains of the BCR may be of various isotypes including IgD, IgM, IgA, IgG or IgE. Similar to the TCR, the immunoglobulin portion of the BCR undergoes V(D)J recombination to generate enormous diversity within a population.

In some instances, an immune cell receptor repertoire library may include a BCR repertoire library, where e.g., the BCR repertoire library may include BCR immunoglobulin chain sequences (including e.g., IgD, IgM, IgA, IgG or IgE chain sequences). Immunoglobulin chain sequences of a subject BCR repertoire library may include full length immunoglobulin chain sequences (e.g., full length heavy chain sequences, full length light chain sequences) or partial immunoglobulin sequences (e.g., partial heavy chain sequences, partial light chain sequences).

Where the subject BCR repertoire library members include partial immunoglobulin chain sequences, the partial immunoglobulin chain sequences may include the entire or essentially the entire immunoglobulin variable region (e.g., the immunoglobulin light chain variable region(s), the immunoglobulin heavy chain variable region(s)). In some instances, the resulting library members include the immunoglobulin variable region(s) and at least a portion of an immunoglobulin constant region. In some instances, the resulting library members include sequence corresponding to the immunoglobulin heavy and/or light chain 5' mRNA ends. In some instances, the resulting library members include sequence from the immunoglobulin heavy or light chain 5' end to at least a portion of the corresponding immunoglobulin chain constant region.

In certain embodiments, preparation of the immune cell-specific library may include BCR specific amplification (including e.g., immunoglobulin chain specific amplification). Such immunoglobulin specific amplification may make use of an immunoglobulin specific primer. By "immunoglobulin specific primer" is meant a primer that specifically hybridizes to a region of an immunoglobulin chain (e.g., a immunoglobulin heavy chain, an immunoglobulin light chain) nucleic acid sequence or the complement thereof. In some instances, an immunoglobulin specific primer may hybridize to only one type of immunoglobulin chain, e.g., only an immunoglobulin heavy chain, only an immunoglobulin light chain, only an IgD chain, only an IgM chain, only an IgA chain, only an IgG chain, only an IgE chain, etc.

Immunoglobulin specific primers may be designed to specifically hybridize to an immunoglobulin heavy chain constant region or the complement thereof. For example, in some instances, an immunoglobulin specific primer may hybridize to a mammalian immunoglobulin heavy chain constant region or a complement thereof, including e.g., a human immunoglobulin heavy chain constant region, a mouse immunoglobulin heavy chain constant region, or the like.

Immunoglobulin specific primers may be designed to specifically hybridize to an immunoglobulin light chain constant region or the complement thereof. For example, in some instances, an immunoglobulin specific primer may hybridize to a mammalian immunoglobulin light chain constant region or a complement thereof, including e.g., a human immunoglobulin light chain constant region, a mouse immunoglobulin light chain constant region, or the like.

Amplification performed during library preparation, including e.g., immune receptor specific amplification, may be performed in a single round or multiple rounds of amplification may be employed. For example, in some instances, after a first round of amplification one or more amplification primers not utilized in the first round may be added to the reaction mixture to facilitate a second round of amplification using the product of the first round of amplification as a nucleic acid template. In some instances, the second or subsequent round(s) of amplification may involve nested amplification, i.e., where the primer binding sites utilized in the second or subsequent round(s) of amplification are within (i.e., one or more nucleotides from the 3' or 5' end) of the product generated in the first round of amplification. Where employed, the degree of nesting will vary as desired including e.g., where the second or subsequent primer binding site is one or more, including 2 or more, 3 or more, 4 or more, 5 or more, 6 or more, 7 or more, 8 or more, 9 or more, 10 or more, 15 or more, 20 or more, etc., nucleotides from the 3' or 5' end of the amplicon generated in the first round of amplification.

In some instances, second or subsequent round(s) amplification will not be nested, including where the second round of amplification makes use of one or more primer binding sites utilized in the prior round of amplification or a primer binding site added during the prior round of amplification (e.g., a primer binding site added as part of a non-templated sequence). In some instances, a second or subsequent round of amplification may make use of a nested primer amplification site at one end and a non-nested (e.g., a prior used primer binding site or an added primer binding site) at the other end, including where the nested site is at the 3' end of the amplicon or the 5' end of the amplicon.

Following prescribed library amplification steps, the prepared libraries may be considered ready for sequencing. In certain embodiments, the methods provided may further include subjecting a prepared immune cell receptor repertoire library to an NGS protocol. The protocol may be carried out on any suitable NGS sequencing platform. NGS sequencing platforms of interest include, but are not limited to, a sequencing platform provided by Illumina® (e.g., the HiSeq™, MiSeq™ and/or NextSeq™ sequencing systems); Ion Torrent™ (e.g.,the Ion PGM™ and/or Ion Proton™ sequencing systems); Pacific Biosciences (e.g., the PACBIO RS II Sequel sequencing system); Life Technologies™ (e.g., a SOLID sequencing system); ROCHE (e.g., the 454 GS FLX+ and/or GS Junior sequencing systems); or any other sequencing platform of interest. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS sequencing system employed.

Single Cells, Reaction Vessels and Droplets

As summarized above, in some instances, a RNA sample may be derived from a single cell to generate a one or more libraries as described herein. Such "single cell libraries" may then be employed in further downstream applications, such as sequencing applications. As used herein, a "single cell" refers to one cell. Single cells useful as the source of template RNAs and/or in generating single cell libraries, such as expression libraries and/or immune cell receptor repertoire libraries can be obtained from a tissue of interest, or from a biopsy, blood sample, or cell culture. Additionally, cells from specific organs, tissues, tumors, neoplasms, or the like can be obtained and used in the methods described herein.

Single cells, for use in such methods, may be obtained by any convenient method. For example, in some instances, single cells may be obtained through limiting dilution of cellular sample. In some instances, the present methods may include a step of obtaining single cells. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 172 by 72 nanowells, with a diameter of 0.1 mm.

In some instances, single cells may be obtained by sorting a cellular sample using a cell sorter instrument. By "cell sorter" as used herein is meant any instrument that allows for the sorting of individual cells into an appropriate vessel for downstream processes, such as those processes of library preparation as described herein.

Useful cell sorters include flow cytometers, such as those instruments utilized in fluorescence activated cell sorting (FACS). Flow cytometry is a well-known methodology using multi-parameter data for identifying and distinguishing between different particle (e.g., cell) types i.e., particles that vary from one another terms of label (wavelength, intensity), size, etc., in a fluid medium. In flow cytometrically analyzing a sample, an aliquot of the sample is first introduced into the flow path of the flow cytometer. When in the flow path, the cells in the sample are passed substantially one at a time through one or more sensing regions, where each of the cells is exposed separately individually to a source of light at a single wavelength (or in some instances two or more distinct sources of light) and measurements of scatter and/or fluorescent parameters, as desired, are separately recorded for each cell. The data recorded for each cell is analyzed in real time or stored in a data storage and analysis means, such as a computer, for later analysis, as desired.

Cells sorted using a flow cytometer may be sorted into a common vessel (i.e., a single tube), or may be separately sorted into individual vessels. For example, in some instances, cells may be sorted into individual wells of a multi-well plate, as described below.

According to certain embodiments, cell sorting may include upstream processes of cell analysis and/or identification, also sometimes referred to as phenotyping. For example, in some instances, cells of a cellular sample may be identified by FACS sorting as having a particular phenotypic characteristic (surface marker expression, viability, morphology, gene expression, cytokine expression, etc.) and selected for further processing based on the characteristic. For example, in some instances, cells of a cellular sample may be sorted based on expressing one or more immune cell markers including e.g., a T cell marker, a B cell marker, or the like, and collected for further downstream processes. In one example, T cells may be selected based on the expression of one or more T cell surface markers (e.g., CD4, CD8, etc.) and the T cells may be collected for further processing. In some instances, cells collected (e.g., through FACS sorting) may be redistributed into single cell samples prior to further processing, including library preparation, as described herein.

Useful cell sorters also include multi-well-based systems that do not employ flow cytometry. Such multi-well based systems include essentially any system where cells may be deposited into individual wells of a multi-well container by any convenient means, including e.g., through the use of Poisson distribution (i.e., limiting dilution) statistics (e.g., multi-sample nanodispense (MSND) systems), individual placement of cells (e.g., through manual cell picking or dispensing using a robotic arm or pipettor). In some instances, useful multi-well systems include a multi-well wafer or chip, where cells are deposited into the wells or the wafer/chip and individually identified by a microscopic analysis system. In some instances, an automated microscopic analysis system may be employed in conjunction with a multi-well wafer/chip to automatically identify individual cells to be subjected to downstream analyses, including library preparation, as described herein.

In some instances, one or more cells may be sorted into or otherwise transferred to an appropriate reaction vessel, where such vessels include those sufficient for performing one or more of the aspects of library preparation as described herein. Reaction components may be added to reaction vessels, including e.g., components for preparing an RNA sample, components for generating a product double stranded cDNA, components for one or more library preparation reactions, etc. Reaction vessels into which the reaction mixtures and components thereof may be added and within which the reactions of the subject methods may take place will vary. Useful reaction vessels include but are not limited to e.g., tubes (e.g., single tubes, multi-tube strips, etc.), wells (e.g., of a multi-well plate (e.g., a 96-well plate, 384 well plate, or a plate with any number of wells such as 2000, 4000, 6000, or 10000 or more). Multi-well plates may be independent or may be part of a chip and/or device.

In some instances, reaction mixtures and components thereof may be added to and the reactions of the subject methods may take place in a liquid droplet (e.g., a water-oil emulsion droplet), e.g., as described in more detail below. Whereas the droplets may serve the purpose of individual reaction vessels, the droplets (or emulsion containing droplets) will generally be housed in a suitable container such as, e.g., a tube or well or microfluidic channel. Amplification reactions performed in droplets may be sorted, e.g., based on fluorescence (e.g., from nucleic acid detection reagent or labeled probe), using a fluorescence based droplet sorter. Useful fluorescence based droplet sorters will vary and may include e.g., a flow cytometers, microfluidic-based droplet sorters, and the like.

As indicated above, in protocols that include a pooling step, the pooling step can be performed after production of a product double stranded cDNA, e.g., from a single cell, from a droplet, from a well, etc. As such, in certain embodiments of the methods described herein, cells are obtained from a tissue of interest (e.g., blood) and a single-cell suspension is obtained. A single cell is placed in one well of a multi-well plate, or other suitable container, such as a microfluidic chamber or tube. The cells are lysed and reaction components are added directly to the lysates. Whether or not pooling of single cells samples is employed the generated libraries may be sequenced to produce reads. This may allow identification of genes that are expressed in each single cell.

In certain embodiments of the methods described herein, droplets are obtained and a single droplet is sorted into one well of a multi-well plate, or other suitable container, such as a microfluidic chamber or tube. The reaction mixture may be added directly to the droplet, e.g., without additional purification.

In some instances, the methods may include the step of obtaining single droplets. Obtaining droplets cells may be done according to any convenient protocol, including e.g., mechanically sorting droplets (e.g., utilizing a fluorescence based sorter (e.g., a flow cytometer or microfluidic-based sorter). Single droplets can be placed in any suitable reaction vessel in which single droplets can be treated individually. For example a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 72 by 72 or 125 by 125 nanowells, with a diameter of 0.1 mm.

The wells (e.g., nanowells) in the multi-well plates may be fabricated in any convenient size, shape or volume. The well may be 100 µm to 1 mm in length, 100 µm to 1 mm in width, and 100 µm to 1 mm in depth. In various embodiments, each nanowell has an aspect ratio (ratio of depth to width) of from 1 to 4. In one embodiment, each nanowell has an aspect ratio of 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from 0.1 nl to 1 µl. The nanowell may have a volume of 1 µl or less, such as 500 nl or less. The volume may be 200 nl or less, such as 100 nl or less. In an embodiment, the volume of the nanowell is 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

The wells can be designed such that a single well includes a single cell or a single droplet. An individual cell or droplet may also be isolated in any other suitable container, e.g., microfluidic chamber, droplet, nanowell, tube, etc. Any convenient method for manipulating single cells or droplets may be employed, where such methods include fluorescence activated cell sorting (FACS), robotic device injection, gravity flow, or micromanipulation and the use of semi-automated cell pickers (e.g. the Quixell™ cell transfer system from Stoelting Co.), etc. In some instances, single cells or droplets can be deposited in wells of a plate according to Poisson statistics (e.g., such that approximately 10%, 20%, 30% or 40% or more of the wells contain a single cell or droplet—which number can be defined by adjusting the number of cells or droplets in a given unit volume of fluid that is to be dispensed into the containers). In some instances, a suitable reaction vessel comprises a droplet (e.g., a microdroplet). Individual cells or droplets can, for example, be individually selected based on features detectable by microscopic observation, such as location, morphology, the presence of a reporter gene (e.g., expression), the presence of a bound antibody (e.g., antibody labeling), FISH, the presence of an RNA (e.g., intracellular RNA labeling), or qPCR.

Following obtainment of a desired cell population or single cells, e.g., as described above, nucleic acids can be released from the cells by lysing the cells. Lysis can be achieved by, for example, heating or freeze-thaw of the cells, or by the use of detergents or other chemical methods, or by a combination of these. However, any suitable lysis method can be used. In some instances, a mild lysis procedure can advantageously be used to prevent the release of nuclear chromatin, thereby avoiding genomic contamination of a cDNA library, and to minimize degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., Neurosci Res 60(4):439-51 (2008)); or 70° C. for 90 seconds in PCR buffer II (Applied Biosystems) supplemented with 0.5% NP-40 (Kurimoto et al., Nucleic Acids Res 34(5):e42 (2006)); or lysis can be achieved with a protease such as Proteinase K or by the use of chaotropic salts such as guanidine isothiocyanate (U.S. Publication No. 2007/0281313).

Where desired, a given single cell or droplet workflow may include a pooling step where a nucleic acid product composition, e.g., made up of product double stranded cDNA, is combined or pooled with the nucleic acid product compositions obtained from one or more additional cells or droplets. The number of different nucleic acid product compositions produced from different cells or droplets that are combined or pooled in such embodiments may vary, where the number ranges in some instances from 2 to 50, such as 3 to 25, including 4 to 20 or 10,000, or more.

In some embodiments, a multi-sample nano-dispenser (MSND) system that includes a multiwell plate, e.g., in the form of an array of addressable nanowells, and a sample dispenser is employed. An example of such a MSND system is the ICELL8® Single-Cell MSND System (Wafergen, Fremont, Ca). Details of the ICELL8® MSND system are further found in U.S. Pat. Nos. 7,833,709 and 8,252,581, as well as published United States Patent Application Publication Nos. 2015/0362420 and 2016/0245813, the disclosures of which are herein incorporated by reference.

Tagmentation

As summarized above, in some instances, the methods provided may include end-capturing one or more ends of a produced product double stranded cDNA. In certain embodiments, such end-capturing may make use of a tagmentation reaction, which may employ one or more tagmentation reaction components. The process of tagmentation employed will vary and may include e.g., 5' end capturing through a tagmentation reaction, 3' end capturing through a tagmentation reaction, or a combination thereof.

Transposomes, employed in tagmentation where present in methods provided, may include a transposase and a transposon nucleic acid that includes a transposon end domain and a post-tagmentation PCR primer binding domain. These domains are defined functionally and so may be one in the same sequence or may be different sequences, as required by the researcher. The domains may also overlap, such that part of the post-tagmentation PCR primer binding domain may be present in the transposon end domain.

A "transposase" means an enzyme that is capable of forming a functional complex with a transposon end domain-containing composition (e.g., transposons, transposon ends, transposon end compositions) and catalyzing insertion or transposition of the transposon end-containing composition into the double-stranded target DNA with which it is incubated in an in vitro transposition reaction. Transposases that find use in practicing the provided methods include, but are not limited to, Tn5 transposases, Tn7 transposases, and Mu transposases. The transposase may be a wild-type transposase. In other aspects, the transposase includes one or more modifications (e.g., amino acid substitutions) to improve a property of the transposase, e.g., enhance the activity of the transposase. For example, hyperactive mutants of the Tn5 transposase having substitution mutations in the Tn5 protein (e.g., E54K, M56A and L372P) have been developed and are described in, e.g., Picelli et al. (2013) *Genome Research* 24:2033-2040.

The term "transposon end domain" means a double-stranded DNA that consists only of the nucleotide sequences (the "transposon end sequences") that are necessary to form the complex with the transposase or integrase enzyme that is functional in an in vitro transposition reaction. A transposon end domain forms a "complex" or a "synaptic complex" or a "transposome complex" or a "transposome composition" with a transposase or integrase that recognizes and binds to the transposon end domain, and which complex is capable of inserting or transposing the transposon end domain into target DNA with which it is incubated in an in vitro transposition reaction. A transposon end domain exhibits two complementary sequences consisting of a "transferred transposon end sequence" or "transferred strand" and a "non-transferred transposon end sequence," or "non-transferred strand." For example, one transposon end domain that forms a complex with a hyperactive Tn5 transposase (e.g., EZ-Tn5 Transposase, EPICENTRE Biotechnologies, Madison, Wis., USA) that is active in an in vitro transposition reaction includes a transferred strand that exhibits a "transferred transposon end sequence" as follows: 5' AGATGTGTATAAGAGACAG 3', (SEQ ID NO:15) and a non-transferred strand that exhibits a "non-transferred transposon end sequence" as follows: 5' CTGTCTCTTATACACATCT 3' (SEQ ID NO:16). The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction. The sequence of the particular transposon end domain to be employed when practicing the provided methods will vary depending upon the particular transposase employed. For example, a Tn5 transposon end domain may be included in the transposon nucleic acid when used in conjunction with a Tn5 transposase. Further details regarding transposases and transposon end domains that may be employed in transposomes of the invention include, but are not limited to: those described in U.S. Pat. Nos. 9,040,256, 9,080,211, 9,080,211 and 9,115,396; the disclosures of which are herein incorporated by reference.

In addition to the transposon end domain, the transposon nucleic acid also includes a post-tagmentation primer binding domain. In some instances, the post-tagmentation primer binding domain may be subsequently utilized in an amplification reaction that adds a sequencing platform adapter construct domain (e.g., through the use of a primer that hybridizes with the post-tagmentation primer binding domain and has an attached sequencing platform adapter construct domain). In some instances, the post-tagmentation primer binding domain may include a sequencing platform adapter construct domain.

Sequencing platform adapter construct domains added during tagmentation or amplification that follows and depends upon tagmentation will vary. Such Sequencing platform adapter constructs may be a nucleic acid domain selected from a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system), a sequencing primer binding domain (e.g., a domain to which the Read 1 or Read 2 primers of the Illumina® platform may bind), a barcode domain (e.g., a domain that uniquely identifies the sample source of the nucleic acid being sequenced to enable sample multiplexing by marking every molecule from a given sample with a specific barcode or "tag"), a barcode sequencing primer binding domain (a domain to which a primer used for sequencing a barcode binds), a molecular identification domain, or any combination of such domains.

As depicted in FIG. 4, the product double stranded cDNA is subjected to tagmentation using transposomes that include a transposase and a transposon nucleic acid including a transposon end domain and a second post-tagmentation PCR primer binding domain. In this example, transposomes including a Tn5 transposase and the Illumina® Nextera® TnRP1 or TnRP2 sequences are used (FIG. 4).

It will be understood that numerous variations to the exemplary tagmentation-mediated end-capture method presented in FIG. 4 are possible. Instead of capturing 3' ends of RNAs, for example, the method may be used to capture 5' ends of RNAs. 5' end capture can be carried out, e.g., by incorporating a post-tagmentation PCR primer binding domain (e.g., an RP2 sequence) into the template switch oligonucleotide, rather than incorporating such a domain into the first strand cDNA primer. According to this variation, post-tagmentation amplification could be carried out using an amplification primer that binds to the post-tagmentation PCR primer binding domain originally present in the template switch oligonucleotide, in conjunction with an amplification primer that binds to, e.g., a TnRP1 or TnRP2 sequence added during a tagmentation step.

In another variation, rather than using two types of transposomes (such as the TnRP1 or TnRP2 transposomes employed in the example above), a single type of transposome (having a single type of post-tagmentation PCR primer binding domain) can be employed. Amplification of the desired tagmentation products could be carried out using a primer that binds to the single type of post-tagmentation PCR primer binding domain provided by the transposome, in conjunction with a primer that binds to a post-tagmentation PCR primer binding domain that has been added during an earlier step (e.g., first strand synthesis or amplification of the double stranded product nucleic acid, etc.).

Figure 5:
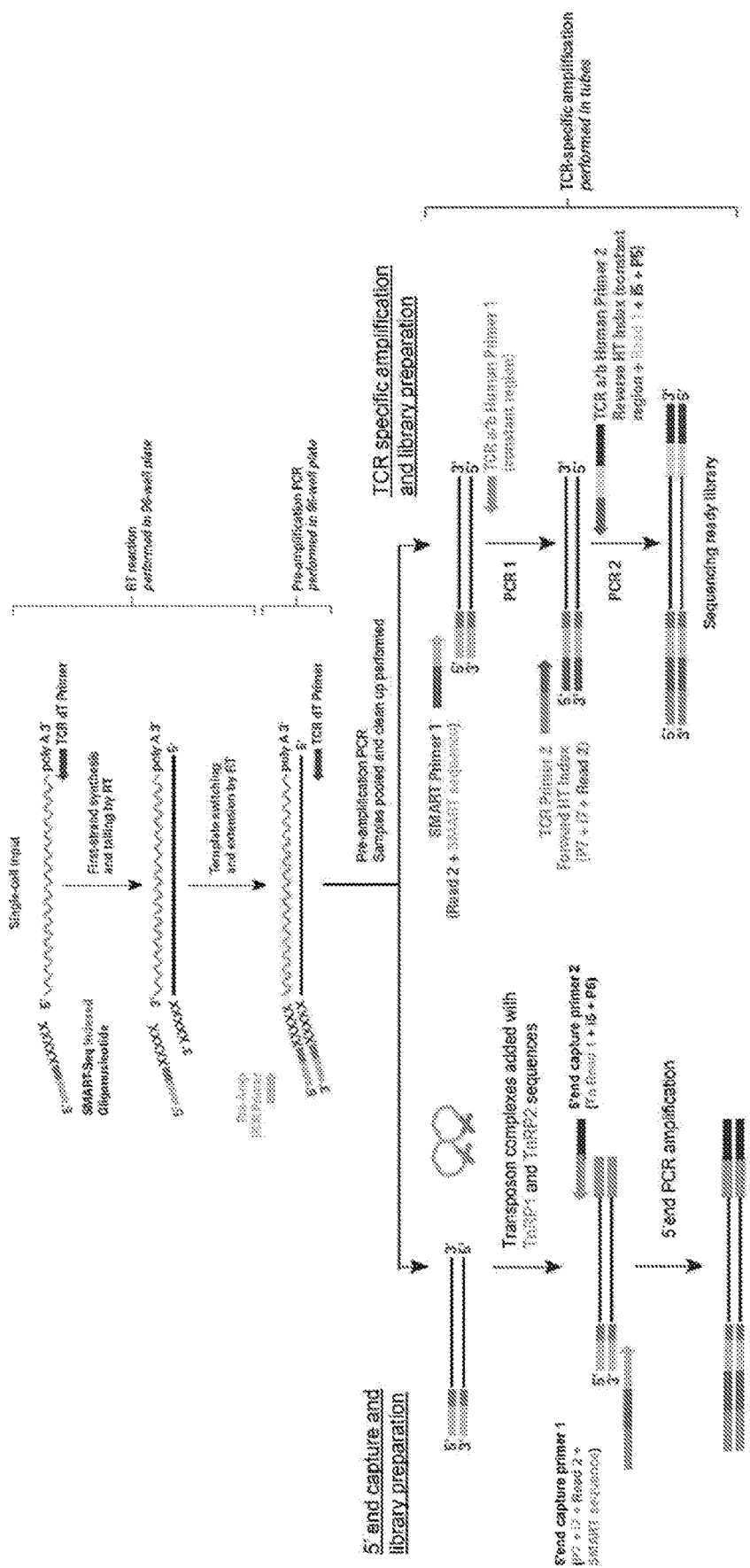
FIG. 5 provides a general schematic showing an overall process employed for producing libraries used for combined differential gene expression analysis and TCR profiling according to an embodiment of the present disclosure.

As a non-limiting example, tagmentation may be performed on a product double stranded cDNA, following splitting of the product double stranded cDNA into two reactions, resulting in the introduction of a TnRP1 sequence into the tagmented 5' end of the product double stranded cDNA. An embodiment of this example is depicted in FIG. 5 which is described in more detail below. As shown in FIG. 5, the tagmentation results in the addition of transposon sequence (e.g., "TnRP1") to the 3' end of the captured 5' product double stranded cDNA. In a subsequent step, the added transposon sequence is utilized as a primer binding site in the amplification of the captured 5' product double stranded cDNA. Specifically, in the example depicted, a first primer that hybridizes the a sequence added in the template switching reaction ("5' end capture primer 1") and a second primer that binds the "Tn Read 1" sequence ("5' end capture primer 2") are used to amplify the captured 5' product double stranded cDNA, while at the same time adding the sequencing platform adapter construct domains necessary to prepare the library for NGS.

In some instances, a primer that binds to an introduced transposon sequence, e.g., at a newly created end of a double stranded nucleic acid caused by the nuclease activity of the transposase, may be referred to as an end amplification primer. Such end amplification primers, in this context, may be employed to amplify from a tagmentation generated end, e.g., towards an original end of the subject RNA. For example, in some instances, an amplification reaction may employ an end amplification primer and second primer that amplifies from the 5' end of a double stranded cDNA (i.e., the end that corresponds to the original 5' end of the RNA). In some instances, an amplification reaction may employ an end amplification primer and second primer that amplifies from the 3' end of a double stranded cDNA (i.e., the end that corresponds to the original 3' end of the RNA).

Other variations include, e.g., replacing Illumina®-specific sequencing domains in the various primers/oligonucleotides with sequencing domains required by sequencing systems from, e.g., Ion Torrent™ (e.g., the Ion PGM™ and Ion Proton™ sequencing systems); Pacific Biosciences (e.g., the PACBIO RS II sequencing system); Life Technologies™ (e.g., a SOLID sequencing system); ROCHE (e.g., the 454 GS FLX+ and GS Junior sequencing systems); or any other sequencing platform of interest.

In a further variation, rather than using one or two types of transposomes (such as the TnRP1 or TnRP2 transposomes employed in the examples above), 3 or more different types of transposomes may be employed for tagmentation. For example, 3 or more, 4 or more, 5 or more, 6 or more, 7 or more, 8 or more, 9 or more, 10 or more, 20 or more, 50 or more, or 100 or more different types of transposomes having different post-tagmentation PCR primer binding domains could be employed. Tagmentation products of interest in such a tagmented sample may be amplified using a primer that binds to a post-tagmentation PCR primer binding domain of a particular type of transposome, in conjunction with a primer that binds to a post-tagmentation PCR primer binding domain added during an earlier step (e.g., first strand synthesis or amplification of the double stranded product nucleic acid, etc.).

When it is desirable to prepare transposomes for the tagmentation step, any suitable transposome preparation approach may be used, and such approaches may vary depending upon, e.g., the specific transposase and transposon nucleic acids to be employed. For example, the transposon nucleic acids and transposase may be incubated together at a suitable molar ratio (e.g., a 2:1 molar ratio, a 1:1 molar ratio, a 1:2 molar ratio, or the like) in a suitable buffer. According to one embodiment, when the transposase is a Tn5 transposase, preparing transposomes may include incubating the transposase and transposon nucleic acid at a 1:1 molar ratio in 2× Tn5 dialysis buffer for a sufficient period of time, such as 1 hour.

Tagmenting the product double stranded cDNA includes contacting the double stranded cDNA with a transposome under tagmentation conditions. Such conditions may vary depending upon the particular transposase employed. Typically, the conditions will include incubating the transposomes and tagged extension products in a buffered reaction mixture (e.g., a reaction mixture buffered with Tris-acetate, or the like) at a pH of from 7 to 8, such as pH 7.5. The transposome may be provided such that about a molar equivalent, or a molar excess, of the transposon is present relative to the tagged extension products. Suitable temperatures include from 32° to 42° C., such as 37° C. The reaction is allowed to proceed for a sufficient amount of time, such as from 5 minutes to 3 hours. The reaction may be terminated by adding a solution (e.g., a "stop" solution), which may include an amount of SDS and/or other transposase reaction termination reagent suitable to terminate the reaction. Protocols and materials for achieving fragmentation of nucleic acids using transposomes are available and include, e.g., those provided in the EZ-Tn5™ transpose kits available from EPICENTRE Biotechnologies (Madison, Wis., USA).

The resultant tagmented sample may then be subjected to PCR amplification conditions using one or more post-tagmentation PCR primers that hybridize to one or more post-tagmentation primer binding sites added during the tagmentation reaction. Post-tagmentation primers may include sequencing platform adapter domains. The sequencing platform adapter construct(s) may include any of the nucleic acid domains described elsewhere herein (e.g., a domain that specifically binds to a surface-attached sequencing platform oligonucleotide, a sequencing primer binding domain, a barcode domain, a barcode sequencing primer binding domain, a molecular identification domain, or any combination thereof). Such embodiments find use, e.g., where nucleic acids of the tagmented sample do not include all of the adapter domains useful or necessary for sequencing in a sequencing platform of interest, and the remaining adapter domains are provided by the primers used for the amplification of the nucleic acids of the tagmented sample.

Template-Switching Reverse Transcription

As summarized above, aspects of the present methods may involve the use of a template-switching reverse transcription reaction. For example, in some instances, the subject methods may include generating a product double stranded cDNA from a nucleic acid sample using a template-switching reverse transcription reaction. Accordingly, in some cases, prior to splitting double-stranded cDNA into separate reaction mixtures that may be separately used to prepare one or more libraries, such as an expression library and/or an immune cell receptor repertoire library, the double-stranded cDNA may be generated from a template nucleic acid using a template-switching reverse transcription reaction.

A template-switching reverse transcription reaction will generally involve a template nucleic acid from which a product double stranded cDNA is generated. Sources and/or methods of generating template nucleic acids will vary. Template nucleic acids may be present in a template nucleic acid composition (e.g., a defined composition) or a biological sample (e.g., a sample obtained from or containing a living organism and/or living cells). Biological samples containing template nucleic acids may be prepared, by any convenient means, to render the nucleic acids of the sample available to components of the herein described methods (e.g., primers, oligonucleotides, etc.).

Methods of preparing biological samples containing template nucleic acids will vary. Useful processes may include but are not limited to e.g., homogenizing the sample, lysing one or more cell types of the sample, enriching the same for desired nucleic acids, removing one or more components present in the sample (e.g., proteins, lipids, contaminating nucleic acids), performing nucleic acid isolation to isolate the template nucleic acids, etc. In some instances, cells of a biological sample may be prepared by lysing the cells of the sample. Useful processes for lysing cells include but are not limited to e.g., chemical lysis, enzymatic lysis, mechanical lysis, freeze/thaw lysis, and the like. In some instances, the cells of the sample may not be fixed prior use of template nucleic acid obtained from the cells or a cell of the sample in a method as described herein. In some instances, the cells of the sample may be fixed prior use of template nucleic acid obtained from the cells or a cell of the sample in a method as described herein.

Template nucleic acids of the subject disclosure may contain a plurality of distinct template nucleic acids of differing sequence. Template nucleic acids (e.g., a template RNA, a template DNA, or the like) may be polymers of any length. While the length of the polymers may vary, in some instances the polymers are 10 nts or longer, 20 nts or longer, 50 nts or longer, 100 nts or longer, 500 nts or longer, 1000 nts or longer, 2000 nts or longer, 3000 nts or longer, 4000 nts or longer, 5000 nts or longer or more nts. In certain aspects, template nucleic acids are polymers, where the number of bases on a polymer may vary, and in some instances is 10 nts or less, 20 nts or less, 50 nts or less, 100 nts or less, 500 nts or less, 1000 nts or less, 2000 nts or less, 3000 nts or less, 4000 nts or less, or 5000 nts or less, 10,000 nts or less, 25,000 nts or less, 50,000 nts or less, 75,000 nts or less, 100,000 nts or less.

According to certain embodiments, the template nucleic acids are template ribonucleic acids (template RNA). Template RNAs may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

The number of distinct template nucleic acids of differing sequence in a given template nucleic acid composition may vary. While the number of distinct template nucleic acids in a given template nucleic acid composition may vary, in some instances the number of distinct template nucleic acids in a given template nucleic acid composition ranges from 1 to $10^8$, such as 1 to $10^7$, including 1 to $10^5$.

The template nucleic acid composition employed in such methods may be any suitable nucleic acid sample. The nucleic acid sample that includes the template nucleic acid may be combined into the reaction mixture in an amount sufficient for producing the product nucleic acid. According to one embodiment, the nucleic acid sample is combined into the reaction mixture such that the final concentration of nucleic acid in the reaction mixture is from 1 fg/µL to 10 µg/µL, such as from 1 µg/µL to 5 µg/µL, such as from 0.001 µg/µL to 2.5 µg/µL, such as from 0.005 µg/µL to 1 µg/µL, such as from 0.01 µg/µL to 0.5 µg/µL, including from 0.1 µg/µL to 0.25 µg/µL. In certain aspects, the nucleic acid sample that includes the template nucleic acid is isolated from a single cell, e.g., as described in greater detail below. In other aspects, the nucleic acid sample that includes the template nucleic acid is isolated from 2, 3, 4, 5, 6, 7, 8, 9, 10 or more, 20 or more, 50 or more, 100 or more, or 500 or more cells. According to certain embodiments, the nucleic acid sample that includes the template nucleic acid is isolated from 500 or less, 100 or less, 50 or less, 20 or less, 10 or less, 9, 8, 7, 6, 5, 4, 3, or 2 cells.

The template nucleic acid may be present in any nucleic acid sample of interest, including but not limited to, a nucleic acid sample isolated from a single cell, a plurality of cells (e.g., cultured cells), a tissue, an organ, or an organism (e.g., mouse, rat, or the like). In certain aspects, the nucleic acid sample is isolated from a cell(s), tissue, organ, and/or the like of a mammal (e.g., a human, a rodent (e.g., a mouse), or any other mammal of interest). In other aspects, the nucleic acid sample is isolated from a source other than a mammal, such as amphibians (e.g., frogs (e.g., *Xenopus*)), fish (zebrafish (*Danio rerio*), or any other non-mammalian nucleic acid sample source.

Approaches, reagents and kits for isolating nucleic acids from such sources are known in the art. For example, kits for isolating nucleic acids from a source of interest—such as the NucleoSpin®, NucleoMag® and NucleoBond® genomic DNA or RNA isolation kits by Takara Bio USA, Inc. (Mountain View, CA)—are commercially available. In certain aspects, the nucleic acid is isolated from a fixed biological sample, e.g., formalin-fixed, paraffin-embedded (FFPE) tissue. Nucleic acids from FFPE tissue may be isolated using commercially available kits—such as the NucleoSpin® FFPE DNA or RNA isolation kits by Takara Bio USA, Inc. (Mountain View, CA).

Figure 3:
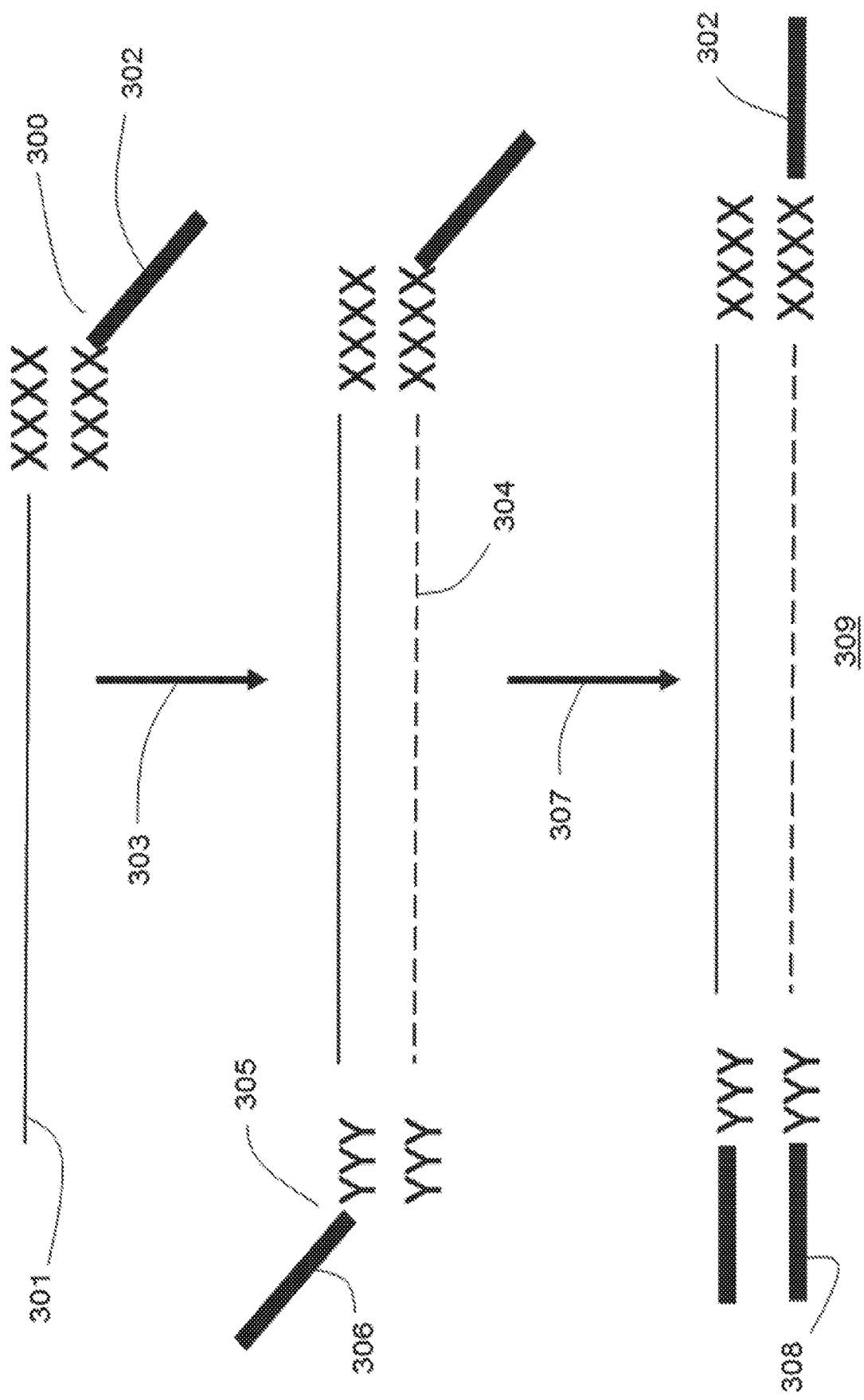
FIG. 3 provides a schematic representation of generating a product double stranded nucleic acid using a template-switching reaction.

A general depiction of a template switching reaction is schematized in FIG. 3. In the example shown, a single product nucleic acid primer (300) hybridizes to a template nucleic acid (301) through complementary sequence (represented by "XXXX") shared by the single product nucleic acid primer and the template. The single product nucleic acid primer may, but need not necessarily, include a region of additional sequence (302) that is not complementary to the template (e.g., non-templated). Following annealing of the single product nucleic acid primer to the template, reverse transcription (303) proceeds, through the use of a reverse transcriptase, to generate a single product nucleic acid strand (304) that is complementary to the template. The reverse transcriptase, having terminal transferase activity, transfers non-templated nucleotides to the generated single product nucleic acid (represented by "YYY") and a template switching oligonucleotide (305) hybridizes to the non-templated nucleotides of the single product nucleic acid by a sequence of complementary nucleotides (also represented by "YYY" and also referred to herein as a 3' hybridization domain) present on the template switch oligonucleotide. The template switch oligonucleotide includes additional sequence (306) that does not hybridize to the non-templated nucleotides. Template switching occurs (307), wherein the reverse transcriptase switches from the template to utilize the template switching oligonucleotide as a second template, transcribing the additional sequence (306) to generate its complement (308). The now fully generated single product nucleic acid strand (309) includes the complete sequence of the single product nucleic acid primer, including any additional sequence (302), if present, that did not hybridize to the template, the complementary sequence of the template and the complementary sequence of the template switch oligonucleotide. Methods and reagents related to template switching are also described in U.S. Pat. No. 9,410,173; the disclosure of which is incorporated herein by reference in its entirety.

Template Switch Oligonucleotide

A template-switching reverse transcription reaction may make use of a template switch oligonucleotide. By "template switch oligonucleotide" is meant an oligonucleotide template to which a polymerase switches from an initial template (e.g., template nucleic acid (e.g., a RNA template)) during a nucleic acid polymerization reaction. In this regard, the template may be referred to as a "donor template" and the template switch oligonucleotide may be referred to as an "acceptor template." As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 10 to 20, 21 to 30, 31 to 40, 41 to 50, 51-60, 61 to 70, 71 to 80, 80 to 100, 100 to 150 or 150 to 200, up to 500 or more nucleotides in length, for example.

A template-switching reverse transcription reaction may make use of a suitable reaction mixture. Suitable reaction mixtures for a template-switching reverse transcription reaction may include the template switch oligonucleotide at a concentration sufficient to readily permit template switching of the polymerase from the template to the template switch oligonucleotide and further elongation by a polymerase as templated by any additional sequence, if present, of the template switch oligonucleotide. For example, the template switch oligonucleotide may be added to the reaction mixture at a final concentration of from 0.01 to 100 μM, such as from 0.1 to 10 μM, such as from 0.5 to 5 μM, including 1 to 2 μM (e.g., 1.2 μM).

In a template-switching reverse transcription reaction, a template switch oligonucleotide may or may not include one or more nucleotides (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the template switch oligonucleotide.

In certain aspects, the template switch oligonucleotide includes a 3' hybridization domain. The 3' hybridization domain may vary in length, and in some instances ranges from 2 to 10 nts in length, such as 3 to 7 nts in length. The 3' hybridization domain of a template switch oligonucleotide may include a sequence complementary to a non-templated sequence added to a single product nucleic acid of the template-switching reaction (e.g., a cDNA). Non-templated sequences, described in more detail below, generally refer to those sequences that do not correspond to and are not templated by a template, e.g., a RNA template or a DNA template. Where present in the 3' hybridization domain of a template switch oligonucleotide, non-templated sequences may encompass the entire 3' hybridization domain or a portion thereof. In some instances, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence may include or consist of a homo-polynucleotide, where such a homo-polynucleotide may vary in length from 2 to 10 nts in length, such as 3 to 7 nts in length, including 3 nts.

A template switch oligonucleotide can be free in solution or can be attached to a solid support (e.g., a bead). In some instances, a template switch oligonucleotide is dried in a container (e.g., a multi well array chip). The dried template switch oligonucleotide can be covalently or non-covalently attached to the container.

Tail Sequences and Tailing

In some instances, the present methods may include generating a double stranded product cDNA and/or amplifying a template nucleic acid having a tail sequence using a primer having a sequence that is complementary to the tail sequence. The term "tail sequence", as used herein, generally refers to a polynucleotide stretch present on the 3' end of the template nucleic acid made up of a single nucleotide species (e.g., A, C, G, T, etc.). In some instances, a first strand complementary deoxyribonucleic acid (cDNA) primer may be, in whole or in part, complementary to a tail sequence. For example, a poly(A) tail of a mRNA template is one non-limiting example of a tail sequence. Accordingly, a first strand cDNA primer may, in some instances, include or consist of a poly(T) sequence that is complementary to the poly(A) tail of a mRNA template.

Tail sequences may be naturally present on a subject template nucleic acid or may be synthetically added. Accordingly, examples of tail sequences that may be present on a subject template nucleic acid include but are not limited to e.g., a poly(A) tail, a poly(C) tail, a poly(G) tail, a poly(T) tail, and the like. Tail sequences may range in size from less than 10 nt to 300 nt or more, including but not limited to e.g., 10 to 300 nt, 10 to 200 nt, 10 to 150 nt, 10 to 100 nt, 10 to 90 nt, 10 to 80 nt, 10 to 70 nt, 10 to 60 nt, 10 to 50 nt, 10 to 40 nt, 10 to 30 nt, 10 to 20 nt, 20 to 300 nt, 20 to 200 nt, 20 to 150 nt, 20 to 100 nt, 20 to 90 nt, 20 to 80 nt, 20 to 70 nt, 20 to 60 nt, 20 to 50 nt, 20 to 40 nt, 20 to 30 nt, 15 nt, 16 nt, 18 nt, 20 nt, etc. Where a template nucleic acid contains a tail sequence, a primer utilized in generating a double stranded product cDNA, e.g., a first strand cDNA primer, may contain a sequence complementary to the tail sequence to which the primer hybridizes and primes elongation of the first strand cDNA. Useful sequences complementary to the tail sequence will vary and may include but are not limited to e.g., a poly(dA) sequence, a poly(dC) sequence, a poly(dG) sequence, a poly(dT) sequence, and the like.

As noted above, tail sequences present on template nucleic acids may be naturally occurring (e.g., in the case of the poly(A) tail of an mRNA template) or may be artificially or synthetically produced. For example, in some instances, a tail sequence may be added to a nucleic acid template, in a tailing reaction. Tailing reactions will vary and may include, e.g., where the tail sequence is added to the template through an enzymatic process. Useful enzymes for tailing a subject nucleic acid template include but are not limited to e.g., terminal transferase (e.g., Terminal Deoxynucleotidyl Transferase, RNA-specific nucleotidyl transferases, and the like). The nucleotide specie of the tailing sequence may be controlled as desired, e.g., by making available in a tailing reaction utilizing a terminal transferase only the desired species of dNTP (e.g., only dATP, only dCTP, only dGTP or only dTTP). In some instances, a "dNTP tailing mix" is used in a tailing reaction where such a mix contains only one species of dNTP (e.g., ATP). In some instances, a nucleic acid template may be prepared for a tailing reaction e.g., by removal of a 3' phosphate (dephosphorylation) present on the nucleic acid template. Any convenient and appropriate phosphatase may be employed for such purposes including but not limited to e.g., Alkaline Phosphatase (e.g., Shrimp Alkaline Phosphatase and derivative thereof), and the like.

In some instances, the subject methods may include performing a tailing reaction to add a tailing sequence to a template nucleic acid, e.g., by contacting a template nucleic acid with a terminal transferase in the presence of a species of dNTP under conditions sufficient to produce the template having the tail sequence (i.e., a tailed template). The rate of addition of dNTPs—and thus the length of tail sequence—is a function of the ratio of 3' ends to the dNTP concentration, and also which dNTP is used. The terminal transferase reaction is carried out at a temperature at which the terminal transferase is active, such as between 30° C. and 50° C., including 37° C. The dNTPs in the terminal transferase reaction may be present at a final concentration of from 0.01 mM to 1 mM, such as from 0.05 mM to 0.5 mm, including 0.1 mM. The template nucleic acid may be present in the terminal transferase reaction at a concentration of from 0.05 to 500 pmol, such as from 0.5 to 50 pmol, including 1 to 25 pmol, e.g., 5 pmol. A terminal transferase buffer solution and any other useful components (e.g., a metal cofactor such as Co, or the like) may also be included in the terminal transferase reaction, e.g., as a separate solution (e.g., buffer) or as part of a "dNTP tailing mix". The terminal transferase reaction results in the addition of nucleotides at the 3' end of the nucleic acid template and the resulting tailed-template nucleic acid may then be utilized in further steps of the reaction according to the subject methods.

In some instances, a template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

In some instances, a template switch oligonucleotide may include a 5' adapter sequence (e.g., a defined nucleotide sequence 5' of the 3' hybridization domain of the template switch oligonucleotide), the 5' adapter sequence may serve various purposes in downstream applications. In some instances, the 5' adapter sequence may serve as a primer binding site for further amplification or, e.g., nested amplification or suppression amplification, of the amplified dsDNA.

Primers

A single product nucleic acid primer, also referred to as a single product nucleic acid synthesis primer (e.g., a first strand cDNA primer) or a first strand primer, includes a template binding domain. For example, the nucleic acid may include a first (e.g., 3') domain that is configured to hybridize to a template nucleic acid, e.g., mRNA, etc., and may or may not include one or more additional domains which may be viewed as a second (e.g., 5') domain that does not hybridize to the template nucleic acid, e.g., a non-template sequence domain as described in more detail below. The sequence of the template binding domain may be independently defined or arbitrary. In certain aspects, the template binding domain has a defined sequence, e.g., poly dT or gene specific sequence. In other aspects, the template binding domain has an arbitrary sequence (e.g., a random sequence, such as a random hexamer sequence). While the length of the template binding domain may vary, in some instances the length of this domain ranges from 5 to 50 nts, such as 6 to 25 nts, e.g., 6 to 20 nts.

The single product nucleic acid primer may or may not include one or more nucleotides (or analogs thereof) that are modified or otherwise non-naturally occurring. For example, the single product nucleic acid primer may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the single product nucleic acid primer.

In some instances, a single product nucleic acid primer may include a 5' adapter sequence (e.g., a defined nucleotide sequence 5' of the 3' hybridization domain of the single product nucleic acid primer), the 5' adapter sequence may serve various purposes in downstream applications. In some instances, the 5' adapter sequence may serve as a primer binding site for further amplification or, e.g., nested amplification or suppression amplification.

In some instances, one or more of the primers or oligonucleotides employed (including e.g., single product nucleic acid primers, template switch oligonucleotides, etc.) may include two or more domains. For example, the primer or oligonucleotide may include a first (e.g., 3') domain that hybridizes to a template and a second (e.g., 5') domain that does not hybridize to a template. The sequence of the first and second domains may be independently defined or arbitrary. In certain aspects, the first domain has a defined sequence and the sequence of the second domain is defined or arbitrary. In other aspects, the first domain has an arbitrary sequence (e.g., a random sequence, such as a random hexamer sequence) and the sequence of the second domain is defined or arbitrary. In some instances, the sequences of both domains are defined. Where a primer (including e.g., single product nucleic acid primers, template switch oligonucleotides, etc.) utilized in the subject methods includes two or more domains, one or more of the domains may include a non-templated sequence as described below.

Polymerases

In some instances, a polymerase combined into a template-switching reverse transcription reaction mixture is capable of template switching, where the polymerase uses a first nucleic acid strand as a template for polymerization, and then switches to the 3' end of a second template nucleic acid strand to continue the same polymerization reaction. In some instances, the polymerase capable of template switching is a reverse transcriptase. Reverse transcriptases capable of template-switching that find use in practicing the subject methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof, e.g., RNase H minus or RNase H reduced enzymes. For example, the reverse transcriptase may be a Moloney Murine Leukemia Virus reverse transcriptase (MMLV RT) or a Bombyx mori reverse transcriptase (e.g., Bombyx mori R2 non-LTR element reverse transcriptase). Polymerases capable of template switching that find use in practicing the subject methods are commercially available and include SMARTScribe™ reverse transcriptase and PrimeScript™ reverse transcriptase available from Takara Bio USA, Inc. (Mountain View, CA).

A template-switching reverse transcription reaction of the present methods may include the use of a polymerase having terminal transferase activity. For example, the polymerase (e.g., a reverse transcriptase such as MMLV RT) combined into the reaction mixture has terminal transferase activity such that a homonucleotide stretch (e.g., a homo-trinucleotide, such as C-C-C) may be added to the 3' end of a nascent strand, and the 3' hybridization domain of the template switch oligonucleotide includes a homonucleotide stretch (e.g., a homo-trinucleotide, such as G-G-G) complementary to that of the 3' end of the nascent strand. In other aspects, when the polymerase having terminal transferase activity adds a nucleotide stretch to the 3' end of the nascent strand (e.g., a trinucleotide stretch), the 3' hybridization domain of the template switch oligonucleotide includes a hetero-trinucleotide comprises a nucleotide comprising cytosine and a nucleotide comprising guanine (e.g., an $r(C/G)_3$ oligonucleotide), which hetero-trinucleotide stretch of the template switch oligonucleotide is complementary to the 3' end of the nascent strand. Examples of 3' hybridization domains and template switch oligonucleotides are further described in U.S. Pat. No. 5,962,272, the disclosure of which is herein incorporated by reference.

A polymerase with terminal transferase activity is capable of catalyzing the addition of deoxyribonucleotides to the 3' hydroxyl terminus of a RNA or DNA molecule. In certain aspects, when the polymerase reaches the 5' end of the template, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent strand. All of the nucleotides may be the same (e.g., creating a homonucleotide stretch at the 3' end of the nascent strand) or one or more of the nucleotides may be different from the other(s) (e.g., creating a heteronucleotide stretch at the 3' end of the nascent strand). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). For example, according to one embodiment, the polymerase is an MMLV reverse transcriptase (MMLV RT). MMLV RT incorporates additional nucleotides (predominantly dCTP, e.g., three dCTPs) at the 3' end of the nascent strand. As described in greater detail elsewhere herein, these additional nucleotides may be useful for enabling hybridization between a 3' hybridization domain of a template switch oligonucleotide and the 3' end of the nascent strand, e.g., to facilitate template switching by the polymerase from the template to the template switch oligonucleotide.

Reverse transcriptase utilized in the subject methods may, in some instances, be a thermo-sensitive polymerase, i.e., a polymerase that is not thermostable. Such thermo-sensitive polymerases may become inactive at a temperature above their active temperature range. For example, in some instances, a thermos-sensitive polymerase may become inactive or demonstrate significantly reduced activity after being exposed to temperatures of 75° or higher, 80° or higher, 85° or higher, 90° or higher or 95° or higher.

Where a reverse transcriptase is employed, it may be combined into the reaction mixture such that the final concentration of the reverse transcriptase is sufficient to produce a desired amount of the RT reaction product, e.g., a desired amount of a single product nucleic acid. In certain aspects, the reverse transcriptase (e.g., an MMLV RT, a Bombyx mori RT, etc.) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

Non-Templated Sequences and Non-Template Sequences

Aspects of the described methods may, in some instances, include the use of non-templated sequences. The terms "non-templated sequence" and "non-template sequence" generally refer to those sequences involved in the subject method that do not correspond to the template (e.g., are not present in the templates, do not have a complementary sequence in the template or are unlikely to be present in or have a complementary sequence in the template). Non-templated sequences are those that are not templated by a template, e.g., a RNA or DNA template, thus they may be, e.g., added during an elongation reaction in the absence of corresponding template, e.g., nucleotides added by a polymerase having non-template directed terminal transferase activity. The addition of non-templated sequence to a nucleic acid need not be necessarily limited to elongation reaction. For example, in some instances, a non-templated sequence may be added through ligation of the non-templated sequence to the nucleic acid. In some instances, a non-templated sequence may be added through a transposase mediated reaction, e.g., through a tagmentation reaction which adds the non-templated sequence to a subject nucleic acid. Accordingly, non-templated sequences may vary and may be added to templated sequence through a variety of means.

Non-template and non-templated sequence may, but not exclusively, refer to those sequences present on a primer, template switch oligonucleotide or transposon that do not hybridize to the nucleic acid template (such sequences may, in some instances, be referred to as non-hybridizing sequence). Non-templated sequence will vary, in both size and composition. In some instances, non-templated sequence, e.g., non-templated sequence present on a template switch oligonucleotide or a primer, may range from 10 nt to 1000 nt or more including but not limited to e.g., 10 nt to 900 nt, 10 nt to 800 nt, 10 nt to 700 nt, 10 nt to 600 nt, 10 nt to 500 nt, 10 nt to 400 nt, 10 nt to 300 nt, 10 nt to 200 nt, 10 nt to 100 nt, 10 nt to 90 nt, 10 nt to 80 nt, 10 nt to 70 nt, 10 nt to 60 nt, 10 nt to 50 nt, 10 nt to 40 nt, 10 nt to 30 nt, 10 nt to 20 nt, etc.

In some instances, a non-templated sequence, as noted above, may be included in the 3' hybridization domain of a template switch oligonucleotide. When present in the 3' hybridization domain of a template switch oligonucleotide, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence present in the 3' hybridization domain of a template switch oligonucleotide may include or consist of a homo-polynucleotide, where such a homo-polynucleotide may vary in length from 2 to 10 nts in length, such as 3 to 7 nts in length, including 3 nts.

Non-templated sequences present on an oligonucleotide or a primer may be present at the 5' end of the oligonucleotide or primer and may, in such instances, be referred to as a 5' non-templated sequence. In some instances, only one oligonucleotide or primer may include a non-templated sequence (e.g., a 5' non-templated sequence) in a subject reaction. In some instances, two or more oligonucleotides and/or primers utilized in a subject reaction may include a non-templated sequence (e.g., a 5' non-templated sequence). Where two or more oligonucleotides and/or primers include a non-templated sequence, different non-templated sequences may be employed. In some instances, where two or more oligonucleotides and/or primers have a 5' non-templated sequence, such sequences may have the same 5' non-templated sequence.

In some instances, non-templated sequence, including e.g., 5' non-templated sequence, may include one or more restriction endonuclease recognition sites. In some instances, one or more restriction endonuclease recognition sites may be incorporated into a subject nucleic acid allowing manipulation of the produced nucleic acid, e.g., by cleaving the subject nucleic acid at one or more of the incorporated restriction endonuclease recognition sites.

In some instances, non-templated sequence, including e.g., 5' non-templated sequence, may include one or more primer binding sites. In some instances, one or more primer binding sites may be incorporated into a subject nucleic acid allowing further amplification of the produced nucleic acid, including e.g., amplifying all or a portion of the nucleic acid using one or more of the primer binding sites.

Useful primer binding sites will vary widely depending on the desired complexity of the primer binding site and the corresponding primer. In some instances, useful primer binding sites include those having complementarity to a II A primer (e.g., as available from Takara Bio USA, Inc., Mountain View, Calif.). According to one embodiment, an oligonucleotide or a primer utilized in generating a product double stranded cDNA includes a non-template sequence that includes a II A primer binding site. According to one embodiment, a nucleic acid utilized in an end capturing reaction includes a non-template sequence that includes a II A primer binding site.

In some instances, non-templated sequence, including e.g., 5' non-templated sequence, may include one or more barcode sequences, In some instances, such barcode sequences may be or may include a unique molecular identifier (UMI) domain and/or a barcoded unique molecular identifier (BUMI) domain. UMI and BUMI nucleic acids, and their use in various applications, are further described in published United States Patent Application Publication No. US20150072344; the disclosure of which is incorporated herein by reference in their entirety.

In some instances, one or more barcode sequences of a non-templated sequence may provide for retrospective identification of the source of a generated nucleic acid, e.g., following a sequencing reaction where the barcode is sequenced. For example, in some instances, a non-templated sequence that includes a barcode specific for the source (e.g., sample, well, cell, etc.)

of the template is incorporated during a reaction. Such source identifying barcodes may be referred to herein as a "source barcode sequence" and such sequences may vary and may be assigned a term based on the source that is identified by the barcode. Source barcodes may include e.g., a sample barcode sequence that retrospectively identifies the sample from which the sequenced nucleic acid was generated, a well barcode sequence that retrospectively identifies the well (e.g., of a multi-well plate) from which the sequenced nucleic acid was generated, a droplet barcode sequence that retrospectively identifies the droplet from which the sequenced nucleic acid was generated, a cell barcode sequence that retrospectively identifies the cell (e.g., of a multi-cellular sample) from which the sequenced nucleic acid was generated, etc. Barcodes may find use in various procedures including e.g., where nucleic acids are pooled following barcoding, e.g., prior to sequencing.

In some instances, a non-templated sequence, e.g., present on an oligonucleotide and/or a nucleic acid primer, includes a sequencing platform adapter construct. By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLID sequencing system); ROCHE (e.g., the 454 GS FLX+ and/or GS Junior sequencing systems); or any other sequencing platform of interest.

In certain aspects, a non-templated sequence includes a sequencing platform adapter construct that includes a nucleic acid domain that is a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind). The sequencing platform adapter constructs may include nucleic acid domains (e.g., "sequencing adapters") of any length and sequence suitable for the sequencing platform of interest. In certain aspects, the nucleic acid domains are from 4 to 200 nts in length. For example, the nucleic acid domains may be from 4 to 100 nts in length, such as from 6 to 75, from 8 to 50, or from 10 to 40 nts in length. According to certain embodiments, the sequencing platform adapter construct includes a nucleic acid domain that is from 2 to 8 nts in length, such as from 9 to 15, from 16-22, from 23-29, or from 30-36 nts in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGACCACCGA-3') (SEQ ID NO:17), P7 (5'-CAAGCAGAAGACGGCATACGAGAT-3') (SEQ ID NO:18), Read 1 primer (5'-ACACTCTTTCCCTACACGACGCTCTTCCGATCT-3') (SEQ ID NO:19) and Read 2 primer (5'-GTGACTGGAGTTCAGACGTGTGCTCTTCCGATCT-3') (SEQ ID NO:20) domains employed on the Illumina®-based sequencing platforms. Other example nucleic acid domains include the A adapter (5'-CCATCTCATCCCTGCGTGTCTCCGACTCAG-3') (SEQ ID NO:21) and P1 adapter (5'-CCTCTCTATGGGCAGTCGGTGAT-3') (SEQ ID NO:22) domains employed on the Ion Torrent™-based sequencing platforms.

The nucleotide sequences of non-templated sequence domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the non-templated sequence (e.g., a template switch oligonucleotide and/or a single product nucleic acid primer, and/or the like) may be designed to include all or a portion of one or more nucleic acid domains in a configuration that enables sequencing the nucleic acid insert (corresponding to the template nucleic acid) on the platform of interest. Sequencing platform adaptor constructs that may be included in a non-templated sequence as well as other nucleic acid reagents described herein, are further described in U.S. patent application Ser. No. 14/478,978 published as US 2015-0111789 A1, the disclosure of which is herein incorporated by reference.

Non-templated sequence may be added to a nucleic acid of interest, e.g., to an oligonucleotide, a nucleic acid primer, a generated dsDNA, etc., by a variety of means. For example, as noted above, non-templated sequence may be added through the action of a polymerase with terminal transferase activity. Non-templated sequence, e.g., present on a primer or oligonucleotide, may be incorporated into a product nucleic acid during an amplification reaction. In some instances, non-templated nucleic acid sequence may be directly attached to a nucleic acid, e.g., to a primer or oligonucleotide prior to amplification, to a product of nucleic acid amplification, etc. Methods of directly attaching a non-templated sequence to a nucleic acid will vary and may include but are not limited to e.g., ligation, chemical synthesis/linking, enzymatic nucleotide addition (e.g., by a polymerase with terminal transferase activity), and the like.

In some instances, the methods may include attaching sequencing platform adapter constructs to ends of a nucleic acid. For example, in some instances, oligonucleotides and/or primers utilized in the subject methods may not include sequencing platform adapter constructs and thus desired sequencing platform adapter constructs may be attached following the production of a nucleic acid of interest. Adapter constructs attached to the ends of a nucleic acid of interest or a derivative thereof may include any sequence elements useful in a downstream sequencing application, including any of the elements described above with respect to the optional sequencing platform adapter constructs of the oligonucleotides and/or primers of the herein described methods. For example, the adapter constructs attached to the ends of nucleic acid of interest or a derivative thereof may include a nucleic acid domain or complement thereof selected from the group consisting of: a domain that specifically binds to a surface-attached sequencing platform oligonucleotide, a sequencing primer binding domain, a barcode domain, a barcode sequencing primer binding domain, a molecular identification domain, and combinations thereof.

Attachment of the sequencing platform adapter constructs may be achieved using any suitable approach. In certain aspects the adapter constructs are attached to the ends of the product nucleic acid or a derivative thereof using an approach that is the same or similar to "seamless" cloning strategies. Seamless strategies eliminate one or more rounds of restriction enzyme analysis and digestion, DNA end-repair, de-phosphorylation, ligation, enzyme inactivation and clean-up, and the corresponding loss of nucleic acid material. Seamless attachment strategies of interest include: the In-Fusion® cloning systems available from Takara Bio USA, Inc. (Mountain View, CA), SLIC (sequence and ligase independent cloning) as described in Li & Elledge (2007) *Nature Methods* 4:251-256; Gibson assembly as described in Gibson et al. (2009) *Nature Methods* 6:343-345; OPEC (circular polymerase extension cloning) as described in Quan & Tian (2009) *PLoS ONE* 4(7): e6441; SLiCE (seamless ligation cloning extract) as described in Zhang et al.

(2012) *Nucleic Acids Research* 40(8): e55, and the GeneArt® seamless cloning technology by Life Technologies (Carlsbad, CA).

Any suitable approach may be employed for providing additional nucleic acid sequencing domains to a nucleic acid of interest or derivative thereof having less than all of the useful or necessary sequencing domains for a sequencing platform of interest. For example, the a nucleic acid of interest or derivative thereof could be amplified using PCR primers having adapter sequences at their 5' ends (e.g., 5' of the region of the primers complementary to the nucleic acid of interest or derivative thereof), such that the amplicons include the adapter sequences in the original nucleic acid as well as the adapter sequences in the primers, in any desired configuration. Other approaches, including those based on seamless cloning strategies, restriction digestion/ligation, or the like may be employed.

Additional Method Parameters

As summarized above, the herein described method may include certain nucleic acid reactions, including e.g., template-switching reverse transcription reactions, nucleic acid amplification reactions, end-capturing reactions, tagmentation reactions and the like. The reaction mixture components in such reaction are combined under conditions sufficient to produce the product of the reaction. For example, in some instances, the reaction components of a template-switching reverse transcription reaction are combined under conditions sufficient to produce a product double stranded cDNA. In some instances, the reaction components of a nucleic acid amplification reaction are combined under conditions sufficient to produce an amplified product nucleic acid. In some instances, the reaction components of an end-capturing reaction are combined under conditions sufficient to produce an end captured nucleic acid. In some instances, the reaction components of a tagmentation reaction are combined under conditions sufficient to produce tagmentated nucleic acid.

By "conditions sufficient to produce" the subject nucleic acid is meant reaction conditions that permit the relevant nucleic acids and/or other reaction components in the reaction to interact with one another in the desired manner. For example, in some instances, the conditions may be sufficient for nucleic acids of the reaction mixture to hybridize. In some instances, the conditions may be sufficient for an enzyme of the reaction mixture to catalyze a chemical process such as e.g., polymerization, hydrolysis, etc. Achieving suitable reaction conditions may include selecting reaction mixture components, concentrations thereof, and a reaction temperature to create an environment in which the relevant processes proceed, including e.g., the relevant nucleic acids hybridize with one another in a sequence specific manner, the relevant polymerase polymerizes resulting in elongation of a nucleic acid, etc. In addition to specific nucleic acids (e.g., template nucleic acids, oligonucleotides, primers, etc.) of a reaction the reaction mixture may include buffer components that establish an appropriate pH, salt concentration (e.g., KCl concentration), etc. Conditions sufficient to produce a double stranded nucleic acid complex may include those conditions appropriate for hybridization, also referred to as "hybridization conditions".

Achieving suitable reaction conditions may include selecting reaction mixture components, concentrations thereof, and a reaction temperature to create an environment in which one or more polymerases are active and/or the relevant nucleic acids in the reaction interact (e.g., hybridize) with one another in the desired manner. In suitable reaction conditions, in addition to reaction components, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction(s) and/or template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Takara Bio USA, Inc. (Mountain View, CA)), betaine, DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and/or template-switching.

One or more reaction mixtures may have a pH suitable for a primer extension reaction and/or template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for primer extension reactions may vary according to factors such as the particular polymerase employed, the melting temperatures of any primers employed, etc. In some instances, a reverse transcriptase (e.g., an MMLV reverse transcriptase) may be employed and the reaction mixture conditions sufficient for reverse transcriptase-mediated extension of a hybridized primer include bringing the reaction mixture to a temperature ranging from 4° C. to 72° C., such as from 16° C. to 70° C., e.g., 37° C. to 50° C., such as 40° C. to 45° C., including 42° C.

In some instances, the methods described herein may include denaturing the template, e.g., by subjecting a reaction mixture containing the template to a temperature sufficient to denature secondary structure of the template. Depending on the context, denaturing may take place before or after one or more reaction components have been added to the reaction mixture and, in some instances, is performed prior to the start of transcription, e.g., reverse transcription to generate the single product nucleic acid. Useful denaturing temperatures will vary and may range from less than 50° C. to more than 100° C., including but not limited to e.g., 50° C. or more, 55° C. or more, 65° C. or more, 70° C. or more, 72° C. or more, 75° C. or more, 80° C. or more, 85° C. or more, 90° C. or more, 95° C. or more, etc.

In some instances, methods provided may include isolating and/or purifying a final nucleic acid product (e.g., a nucleic acid library) and/or an intermediate nucleic acid product (e.g., a double stranded product cDNA). Any convenient method of purification may be employed including but not limited to e.g., nucleic acid precipitation (i.e., alcohol precipitation), gel purification, etc.

In some instances, methods provided may include the use of an amplification polymerase, e.g., for use in amplifying a produced double stranded cDNA, a produced nucleic acid library, etc. Any convenient amplification polymerase may be employed including but not limited to DNA polymerases including thermostable polymerases. Useful amplification polymerases include e.g., Taq DNA polymerases, Pfu DNA polymerases, derivatives thereof and the like. In some instances, the amplification polymerase may be a hot start polymerase including but not limited to e.g., a hot start Taq DNA polymerase, a hot start Pfu DNA polymerase, and the like.

An amplification polymerase may be combined into a reaction mixture such that the final concentration of the amplification polymerase is sufficient to produce a desired amount of the product nucleic acid, e.g., a desired amount of amplified product double stranded cDNA, a desired amount of library nucleic acid, etc. In certain aspects, the amplification polymerase (e.g., a thermostable DNA polymerase, a hot start DNA polymerase, etc.) is present in the reaction mixture at a final concentration of from 0.1 to 200 units/μL (U/μL), such as from 0.5 to 100 U/μL, such as from 1 to 50 U/μL, including from 5 to 25 U/μL, e.g., 20 U/μL.

Nucleic acid reactions, e.g., amplification reactions, of the subject methods may include combining dNTPs into a reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). In some instances, one or more types of nucleotide added to the reaction mixture may be a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

Reaction mixtures may be subjected to various temperatures to drive various aspects of the reaction including but not limited to e.g., denaturing/melting of nucleic acids, hybridization/annealing of nucleic acids, polymerase-mediated elongation/extension, etc. Temperatures at which the various processes are performed may be referred to according to the process occurring including e.g., melting temperature, annealing temperature, elongation temperature, etc. The optimal temperatures for such processes will vary, e.g., depending on the polymerase used, depending on characteristics of the nucleic acids, etc. Optimal temperatures for particular polymerases, including reverse transcriptases and amplification polymerases, may be readily obtained from reference texts. Optimal temperatures related to nucleic acids, e.g., annealing and melting temperatures may be readily calculated based on known characteristics of the subject nucleic acid including e.g., overall length, hybridization length, percent G/C content, secondary structure prediction, etc.

According to certain embodiments, the subject methods may include isolating, amplifying and/or analyzing (e.g., sequencing) a deoxyribonucleic acid (DNA). Where the subject methods include isolating, amplifying and/or analyzing DNA the DNA employed may be referred to as a DNA template (or sometimes referred to as template DNA). Template DNAs may be any type of DNA (or sub-type thereof) including, but not limited to, genomic DNA (e.g., animal genomic DNA (e.g., mammalian genomic DNA (e.g., human genomic DNA, rodent genomic DNA (e.g., mouse, rat, etc.), etc.), mitochondrial DNA, or any combination of DNA types thereof or subtypes thereof.

In certain embodiment, genomic DNA (gDNA) may be isolated and/or processed for analysis as desired. For example, in some instances, the provided methods may include the preparation of one or more libraries from a sample containing RNA and further include isolating, processing and/or analyzing gDNA from the sample. Accordingly, in some instances, samples may include those that contain both RNA and DNA (e.g., gDNA), including e.g., nucleic acid samples isolated from a plurality of cells and samples isolated from a single cell. For example, in some instances, the subject methods may include isolating, processing and/or analyzing RNA and DNA from a single cell, including where e.g., processing of the RNA includes the preparation of two or more libraries (e.g., an expression library and an immune cell receptor repertoire library) from the RNA sample.

Isolating, processing and/or analyzing of gDNA may be performed for a variety of purposes. For example, in some instances, the gDNA of a sample may be sequenced to obtain genomic sequence information. Such sequencing of gDNA of a subject sample may, in some instances, include sequencing an immune locus or one or more immune loci. By "immune locus" is generally meant a genetic locus of any immune related gene, including those genes associated with immune system process (such as the genes identified by gene ontology (GO) accession number GO:0002376 (available online at geneontology(dot)org) including but not limited to e.g., those genes associated with B cell mediated immunity, B cell selection, T cell mediated immunity, T cell selection, activation of immune response, antigen processing and presentation, antigen sampling in mucosal-associated lymphoid tissue, basophil mediated immunity, eosinophil mediated immunity, hemocyte differentiation, hemocyte proliferation, immune effector process, immune response, immune system development, immunological memory process, leukocyte activation, leukocyte homeostasis, leukocyte mediated immunity, leukocyte migration, lymphocyte costimulation, lymphocyte mediated immunity, mast cell mediated immunity, myeloid cell homeostasis, myeloid leukocyte mediated immunity, natural killer cell mediated immunity, negative regulation of immune system process, neutrophil mediated immunity, positive regulation of immune system process, production of molecular mediator of immune response, regulation of immune system process, somatic diversification of immune receptors, tolerance induction, and the like.

In some instances, an immune locus that may be sequenced and/or otherwise analyzed in the subject methods may be a TCR locus. In some instances, an immune locus that may be sequenced and/or otherwise analyzed in the subject methods may be a BCR locus. In some instances, sequencing the gDNA of an immune locus may allow for coordinated analysis with one or more NGS analyses of a library produced herein, including e.g., an expression library and/or an immune cell receptor repertoire library. In some instances, gDNA analysis performed in the provided methods may include whole genome sequencing.

Compositions and Kits

Aspects of the present disclosure also include compositions and kits. The compositions and kits may include, e.g., one or more of any of the reaction mixture components described above with respect to the subject methods. For example, the compositions and kits may include a nucleic acid sample (e.g., an RNA sample, a combined RNA and DNA sample, etc.), an amplification polymerase (e.g., a thermostable polymerase, etc.), a reverse transcriptase (e.g., a reverse transcriptase capable of template-switching, etc.), a template switch oligonucleotide, an end-capture primer, an immune receptor specific primer, one or more components of a tagmentation reaction, dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s).

In some instances, components of the subject compositions and/or kits may be presented as a "cocktail" where, as used herein, a cocktail refers to a collection or combination of two or more different but similar components in a single vessel. Useful cocktails in the subject kits include but are not limited to e.g., "primer cocktails" where the composition of such cocktails may vary and may include e.g., a cocktail of two or more primers including e.g., an end amplification primer and an immune receptor specific primer, and the like. Useful cocktails in the subject kits may also include but are not limited to e.g., "tagmentation cocktails" where the composition of such cocktails may vary and may include e.g., a cocktail of two or more components of a tagmentation reaction including e.g., a transposon and a transposase.

In certain embodiments, the kits include reagents for isolating nucleic acids from a nucleic acid source of interest. The reagents may be suitable for isolating nucleic acid samples from a variety of DNA or RNA sources including single cells, cultured cells, tissues, organs, or organisms. The subject kits may include reagents for isolating a nucleic acid sample from a fixed cell, tissue or organ, e.g., formalin-fixed, paraffin-embedded (FFPE) tissue. Such kits may include one or more deparaffinization agents, one or more agents suitable to de-crosslink nucleic acids, and/or the like.

Components of the kits may be present in separate containers, or multiple components may be present in a single container. For example, components for performing a template-switching reaction and components for library preparation (e.g., used after the splitting of a produced double stranded cDNA) may be provided in different tubes. In some instances, a template switch oligonucleotide and a first strand cDNA primer may be provided in the same tube, or may be provided in different tubes. In some instances, one or more immune receptor specific primers and one or more end (e.g., 5' end) primers may be provided in the same tube, or may be provided in different tubes. In some instances, one or more end (e.g., 5' end or 3' end) primers and one or more post-tagmentation primers may be provided in the same tube, or may be provided in different tubes. In some instances, deoxyribonucleotide triphosphates (dNTPs) may be included in the same tube as the reverse transcriptase, the amplification polymerase, or one or more primers or oligonucleotides.

In certain embodiments, the provided kits may include some combination of a 5' amplification primer, an immune cell receptor-specific amplification primer (i.e., an immune receptor specific primer) and an end amplification primer. For example, a kit may include a combination of: a 5' amplification primer that binds to a primer binding site added by template switch oligonucleotide; an immune cell receptor-specific amplification primer that specifically binds to a region (e.g., a constant region) of one or more immune cell receptor polypeptides (e.g., a TCRα chain, a TCRβ chain, an immunoglobulin chain); and an end amplification primer that is employed in end-capture (e.g., that binds to a primer binding site added in an end-capture process such as, e.g., a tagmentation reaction).

In certain instances, the provided kits may include one or more components for performing a template-switching reverse transcription reaction. Such components include but are not limited to those described herein including e.g., a template switching oligonucleotide, a primer, a reverse transcriptase, etc. Such components, e.g., oligonucleotides and primers, may, in some instances, include an adapter sequence. For example, in some instances, the provided template switching oligonucleotide may include a 5' adapter sequence.

In certain instances, the provided kits may include one or more components for performing a tagmentation reaction. For example, such kits may include one reagent or some combination of a transposon nucleic acid comprising a post-tagmentation amplification primer binding domain; a post-tagmentation amplification primer that hybridizes to the post-tagmentation amplification primer binding domain; a transposase (e.g., a Tn5 transposase); or some other combination that may include one or more additional components described herein a combination thereof.

In certain instances, the provided kits may included on or more components for running a plurality of reactions on an automation system (e.g., ICELL8 system from Takara Bio USA). The provided kit can include a multi-well plate (i.e., array chip.) The multi-well array chip can comprise a template switch oligonucleotide and/or any other primer of the disclosure in the wells of the multi-well array chip (e.g., in a dried down format).

In addition to the above-mentioned components, a subject kit may further include instructions for using the components of the kit, e.g., to practice the subject methods as described above. In addition, e.g., where the primers and/or oligonucleotides of a kit include a BUMI domain, the kit may further include programming for analysis of results including, e.g., decoding encoded BUMI domains, counting unique molecular species, etc. The instructions and/or analysis programming are generally recorded on a suitable recording medium. The instructions and/or programming may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The subject compositions may be present in any suitable environment. According to one embodiment, the composition is present in a reaction tube (e.g., a 0.2 mL tube, a 0.6 mL tube, a 1.5 mL tube, or the like) or a well or microfluidic chamber or droplet or other suitable container. In certain aspects, the composition is present in two or more (e.g., a plurality of) reaction tubes or wells (e.g., a plate, such as a 96-well plate, a multi-well plate, e.g., containing about 1000, 5000, or 10,000 or more wells). The tubes and/or plates may be made of any suitable material, e.g., polypropylene, or the like, PDMS, or aluminum. The containers may also be treated to reduce adsorption of nucleic acids to the walls of the container. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells or materials such as aluminum having high heat conductance. In some instances, the compositions of the disclosure may be present in droplets. In certain embodiments it may be convenient for the reaction to take place on a solid surface or a bead, in such case, the single product nucleic acid primer and/or template switch oligonucleotide, or one or more other primers, may be attached to the solid support or bead by methods known in the art—such as biotin linkage or by covalent linkage—and reaction allowed to proceed on the support. Alternatively, the oligos may be synthesized directly on the solid support—e.g. as described in Macosko, E Z et. al, Cell 161, 1202-1214, May 21, 2015).

Other suitable environments for the subject compositions include, e.g., a microfluidic chip (e.g., a "lab-on-a-chip device", e.g., a microfluidic device comprising channels and inlets). The composition may be present in an instrument configured to bring the composition to a desired temperature, e.g., a temperature-controlled water bath, heat block, heat block adaptor, or the like. The instrument configured to bring the composition to a desired temperature may be configured to bring the composition to a series of different desired temperatures, each for a suitable period of time (e.g., the instrument may be a thermocycler).

Utility

The subject methods find use in a variety of applications, including those that employ immune cell receptor repertoire analysis and/or analysis of two or more differently prepared sequencing libraries, including where such analysis may be performed sequentially of simultaneously.

As noted above, in some instances, data obtained from two differently prepared libraries may be coordinated. Such coordinated data may serve a common or related purpose. For example, in some instances, data obtained from an immune cell receptor repertoire library may be coordinated with data obtained from an expression library. In some embodiments, sequencing of an immune cell receptor repertoire library may provide information as to identifying the repertoire of immune receptors expressed by a cell, a population of cells, or a subject or a population of subjects, and differential expression analysis of an expression library may provide information as to relative levels of gene expression that may be correlated with the immune receptor repertoire information. For example, in some instances, the expression library may provide differential expression information related to the whole transcriptome of one or more cells (e.g., as part of a whole transcriptome analysis (WTA)) and such transcriptome information may be compared to or correlated with immune receptor repertoire information for the same one or more cells. As another example, in some instances, the expression library may provide differential expression information related to the expression of one or more immune related genes (e.g., cytokines, interleukins, interleukin receptors, CD4, CD8, CD3, PD-1, etc.) in one or more cells and such immune related gene expression information may be compared to or correlated with immune receptor repertoire information for the same one or more cells. Through such processes, relationships between a cell's, or a population of cells', immune receptor repertoire and the expression of other genes, including immune related gene and non-immune related genes, may be identified and/or further investigated.

Furthermore, the use of a single product double stranded cDNA in parallel library preparation may allow for an increase in the consistency of results and in the ability to correlate results across data sets. In addition, using a single product double stranded cDNA in multiple library preparation methods further finds use in those methods where reduced user input and "hands-on time" is desired to produce two or more libraries, regardless of whether the data from the two or more libraries is or is not to be later correlated.

Applications of the subject methods include medical and research applications where the identification and/or screening of immune molecules is desired. Such applications include human clinical research applications as well as pre-clinical research applications, such as those performed on animal models such as e.g., rodents, small and large mammals, non-human primates, etc.

The sequencing-ready libraries generated in the herein disclosed methods include adapter sequences that enable sequencing of the library members using any convenient sequencing platform, including: the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLID sequencing systems from Life Technologies™, the 454 GS FLX+ and GS Junior sequencing systems from ROCHE, or any other convenient sequencing platform. The provided methods find use in generating one or more sequencing ready libraries corresponding to any single sample of RNA starting material of interest, e.g., mRNA, non-polyadenylated RNA (e.g., microRNA). In addition, the present methods may be employed to generate sequencing-ready cDNA libraries, singly or in parallel, from single RNA samples derived an individual single cells or from related populations of cells.

The following example is offered by way of illustration and not by way of limitation.

EXAMPLES

Example 1

Combined Differential Gene Expression Analysis and TCR Profiling from Single Cells The general schematic showing the overall process employed for producing the libraries used for combined differential gene expression analysis and TCR profiling from single cells is provide in FIG. 5.

Reverse Transcription (RT) Reaction and Pre-Amplification PCR

In the first section of the protocol, double stranded cDNA was produced from a mRNA sample obtained from a single-cell input through a template-switching reverse transcription reaction. Single cell mRNA samples were dispersed in wells of a 96-well plate and a T cell receptor (TCR) dT Primer and reverse transcriptase (RT) were used in each well for first-strand synthesis from the single cell mRNA samples. The terminal transferase activity of the RT resulted in tailing of the synthesized first-strands. A SMART-SEQ Indexed Oligonucleotide was hybridized to the tailed nucleotides allowing for template-switching of the RT and extension of the synthesized first-strands to include the index and pre-amplification PCR primer binding site sequences templated by the SMART-SEQ Indexed Oligonucleotide.

Next TCR dT Primer and Pre-Amp PCR Primer, which hybridizes to the pre-amplification PCR primer binding site, were used to amplify the product of the template-switching reaction to ultimately generate product double stranded cDNA. The produced product double stranded cDNA from each well, which contains an index sequence unique to each single cell reaction, were pooled and PCR clean-up was performed. After pooling and clean-up, the double-stranded cDNA was split between two reactions to separately generate sequencing libraries for (1) differential sequence analysis and (2) TCR profiling.

Differential Sequence Analysis Library Preparation

Preparation of the sequencing library for differential sequence analysis was performed by 5' end capture. In brief, the product double-stranded cDNA was tagmented using TnRP1 and TnPR2 transposons and a Tn5 transposase. Tagmentation resulted in product double stranded cDNA fragments having a complete 5' end (i.e., maintaining the index and pre-amplification PCR primer binding site sequences) and a tagmented 3' end with an incorporated post-tagmentation amplification primer binding domain. Two 5' end capture primers, the first ("5'end capture primer 1") hybridizing to the pre-amplification PCR primer binding site sequence and the second ("5'end capture primer 2") to the post-tagmentation amplification primer binding domain, were used to amplify the tagmented 5' fragment and incorporate sequencing adapter sequences. The first primer ("5' end capture primer 1") included P7, i7, Read 2 and SMART sequences. The second primer ("5' end capture primer 2") included P5, i5, and Tn Read 1 sequences). Following amplification the library was complete and ready for sequencing.

TCR Profiling Library Preparation

Preparation of the TCR specific library for TCR profiling analysis was performed in tubes using TCR specific amplification and sequence adapter addition. TCR specific amplification was achieved using SMART Primer 1, which included Read 2 sequence as well as SMART sequence and a primer specific for the human TCR alpha/beta chain constant regions ("TCR a/b Human Primer 1"). In the first round of amplification ("PCR 1") SMART Primer 1 hybridized to the pre-amplification PCR primer binding site sequence and TCR a/b Human Primer 1 hybridized to the TCR alpha/beta chain constant regions. A second round of amplification ("PCR 2") was performed using: TCR Primer 2 Forward HT Index, which hybridized to Read 2 sequence and incorporated P7 and i7 sequences; and TCR a/b Human Primer 2 Reverse HT Index, which hybridized to the amplified TCR alpha/beta constant region sequence and incorporated Read 1, i5 and P5 sequences. Following amplification the library was complete and ready for sequencing.

Example 2

Single-Cell T-Cell Receptor Profiling

Figure 7:
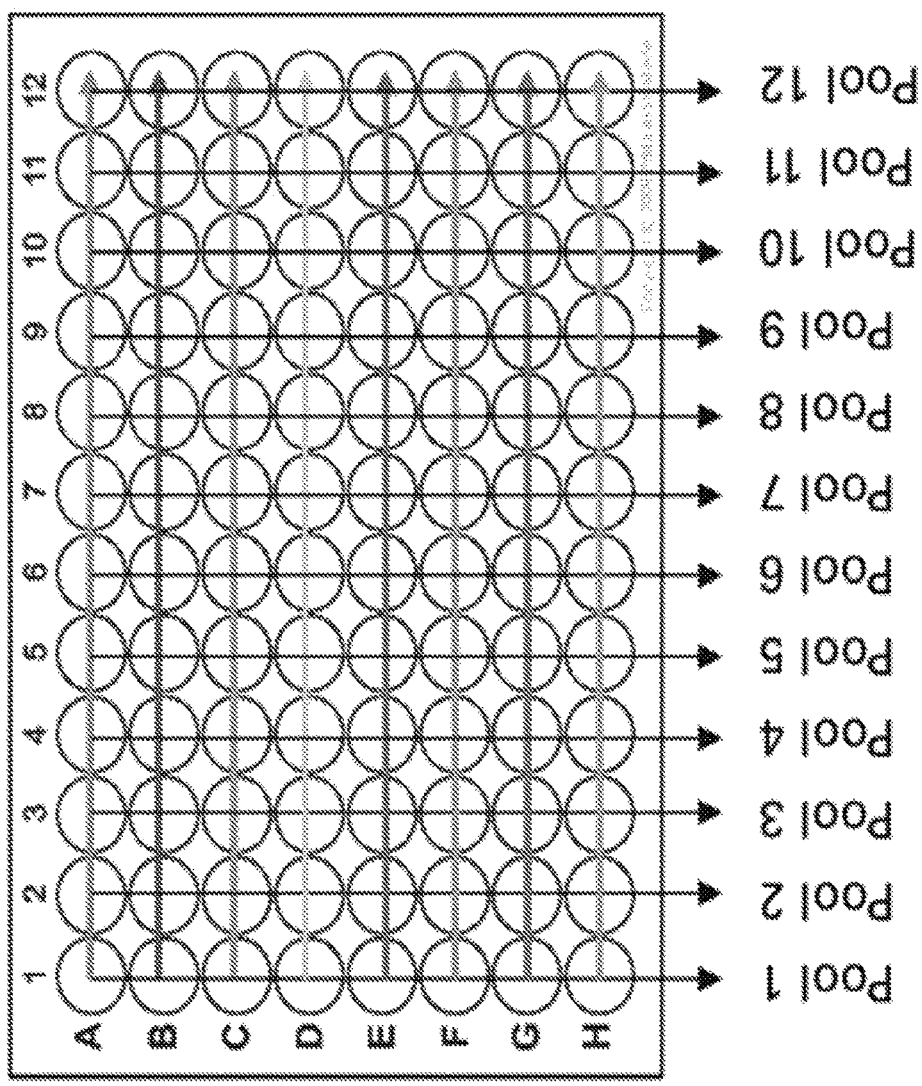
FIG. 7 depicts the indexing oligo distribution and pooling of samples in a 96-well plate as related to the example illustrated in FIG. 6.

Single cells were sorted into lysis buffer in individual wells of a 96-well plate. Reverse transcription reagents were then added to the plate, including a uniquely-indexed SMART-SEQ oligonucleotide for each row (A-H, FIG. 7). RT and pre-amplification PCR steps were performed in each well of the plate, and products were pooled by column, yielding 12 pools that each contain a mixture of cDNA molecules that were barcoded according to the individual cells from which they were derived. Subsequent library construction steps (as described in more detail below) were performed on each of the 12 pools, reducing the number of libraries that need to be prepared from 96 to 12. Inclusion of the barcodes allowed for demultiplexing of sequencing data for each pool, thereby allowing for single-cell resolution and pairing of sequence information for TCR-α and TCR-β subunits.

Figure 6:
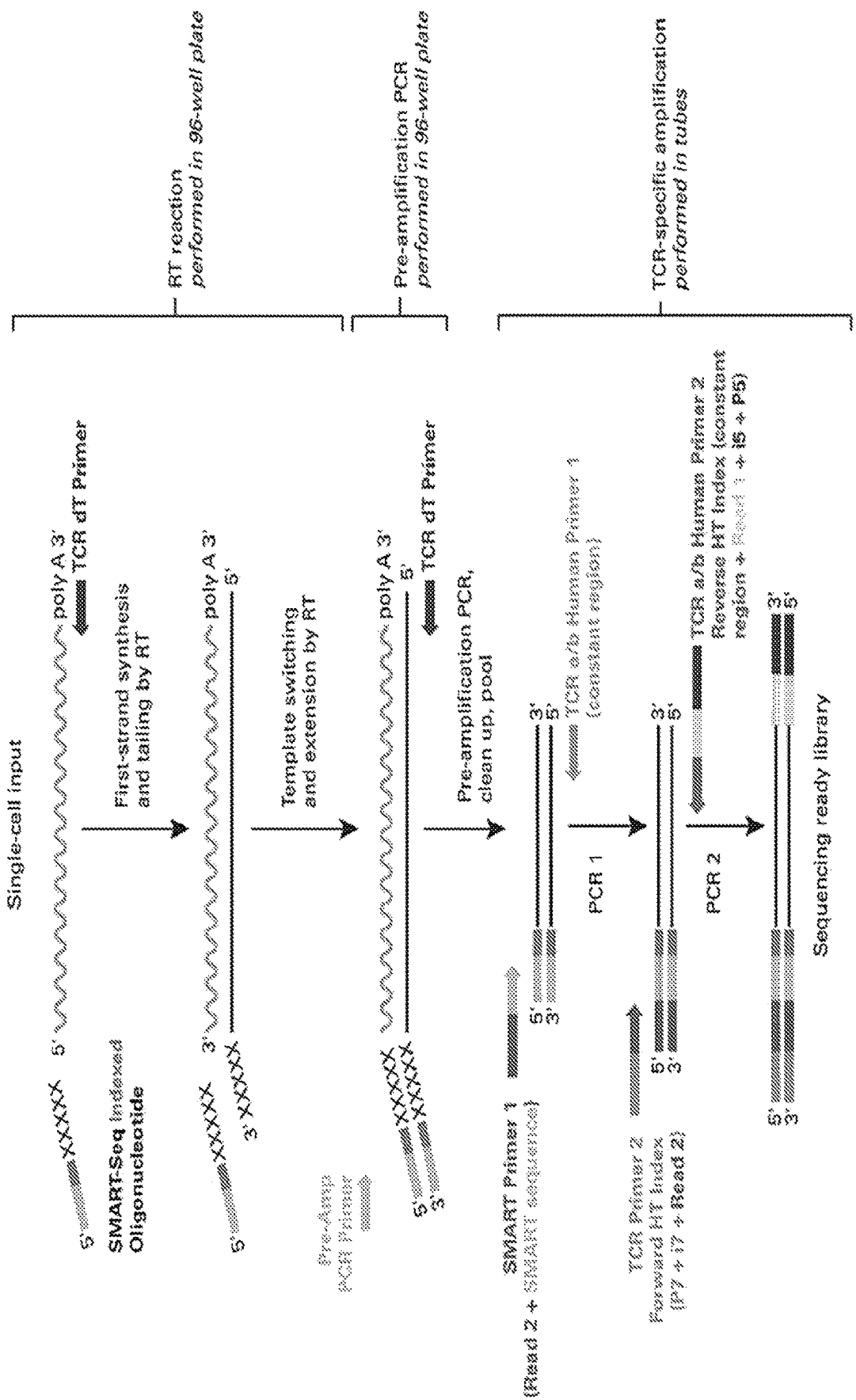
FIG. 6 provides a general schematic showing the overall process employed for TCR profiling library preparation from single T cells as described in the relevant example provided herein.

The general schematic showing the overall process employed for TCR profiling library preparation from single T cells is provide in FIG. 6. The process employed for library preparation was similar to the TCR profiling library preparation portion of the process described in Example 1.

In brief, single cells were sorted into a 96-well plate. First-strand cDNA synthesis was primed by the TCR dT Primer and performed by an MMLV-derived reverse transcriptase (RT). Upon reaching the 5' end of each mRNA molecule, the RT added non-templated nucleotides to the first-strand cDNA. The SMART-SEQ® Indexed Oligonucleotide included a sequence that is complementary to the non-templated nucleotides added by the RT in addition to a row-specific index sequence, and hybridized to the first-strand cDNA. In the template-switching step, the RT used the remainder of the SMART-SEQ Indexed Oligonucleotide as a template for the incorporation of an additional sequence on the end of the first-strand cDNA.

A pre-amplification PCR step was then performed in each well to generate double-stranded cDNA, which serves as starting material for PCR amplification and library construction. Following a cleanup step, cDNA from each column of the 96-well plate was pooled in separate tubes (see FIG. 7), and TCR-specific sequences were amplified by PCR using primers that are complementary to the oligonucleotide-templated sequence ("SMART Primer 1") and the constant region(s) of TCR-α and/or TCR-β subunits ("TCR a/b Human Primer 1"). A subsequent round of PCR was performed to further amplify variable regions of TCR-α and/or TCR-β subunits and incorporate adapter sequences, using TCR Primer 2 Forward HT Index and TCR a/b Human Primer 2 Reverse HT Index. Included in the primers were adapter and index sequences (read 2+i7+P7 and read 1+i5+P5, respectively) that are compatible with the Illumina® sequencing platform. Following purification, size selection, and quality analysis, TCR cDNA libraries were sequenced on the Illumina platform using 300 bp paired-end reads.

For testing of workflow performance, TCR-α and TCR-β sequence libraries were generated from either single Jurkat cells or from single cell-equivalent amounts of Jurkat RNA (2.5 pg of RNA). Eight cells and eight RNA samples were processed individually in a 96-well plate, using a different SMART-SEQ Indexed Oligo for each input of the same type. RT and pre-amplification PCR reactions were performed in each well, and cDNA products derived from inputs of the same type were pooled together prior to subsequent rounds of PCR, as described above. Final libraries were sequenced on a MiSeq with 300 bp paired-end reads. Following sequencing, barcode sequences derived from the SMART-SEQ Indexed Oligos were used to demultiplex the sequencing data, which was then analyzed using MiXCR (Bolotin et al., (2015) Nat. Methods 12(5):380-381).

Figure 8:
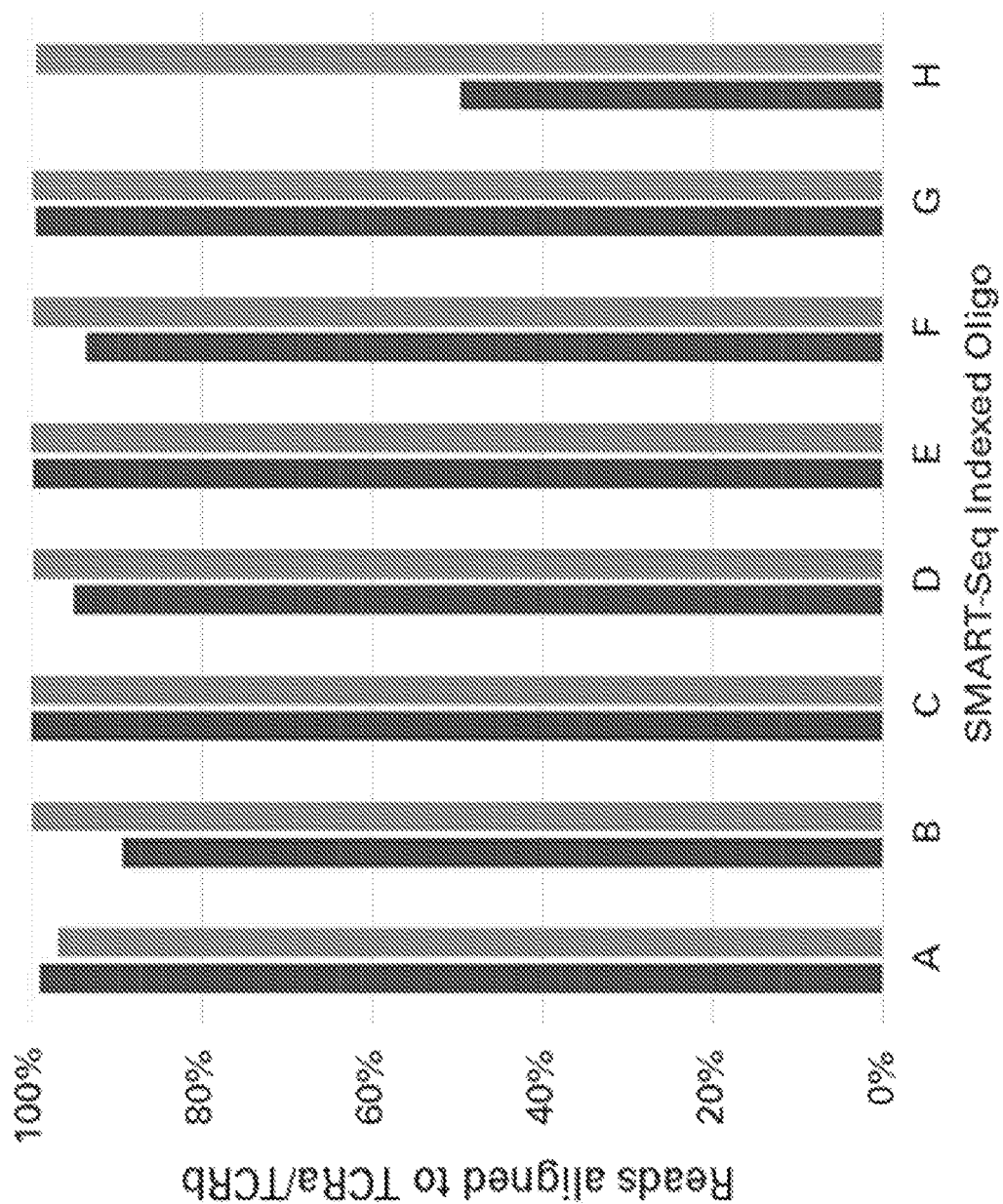
FIG. 8 provides data testing the performance of an immune cell profiling workflow, showing the percentages of sequencing reads that map to TCR-α or TCR-β CDR3 regions generated from either single Jurkat cells or single cell-equivalent amounts of Jurkat RNA.

The percentages of sequencing reads that map to CDR3 regions in TCR-α or TCR-β from each cell or RNA sample were determined (FIG. 8). For each RNA sample, >96% of reads mapped to either TCR subunit. For seven out of the eight cells analyzed, >89% of reads mapped to either TCR subunit.

Figure 9:
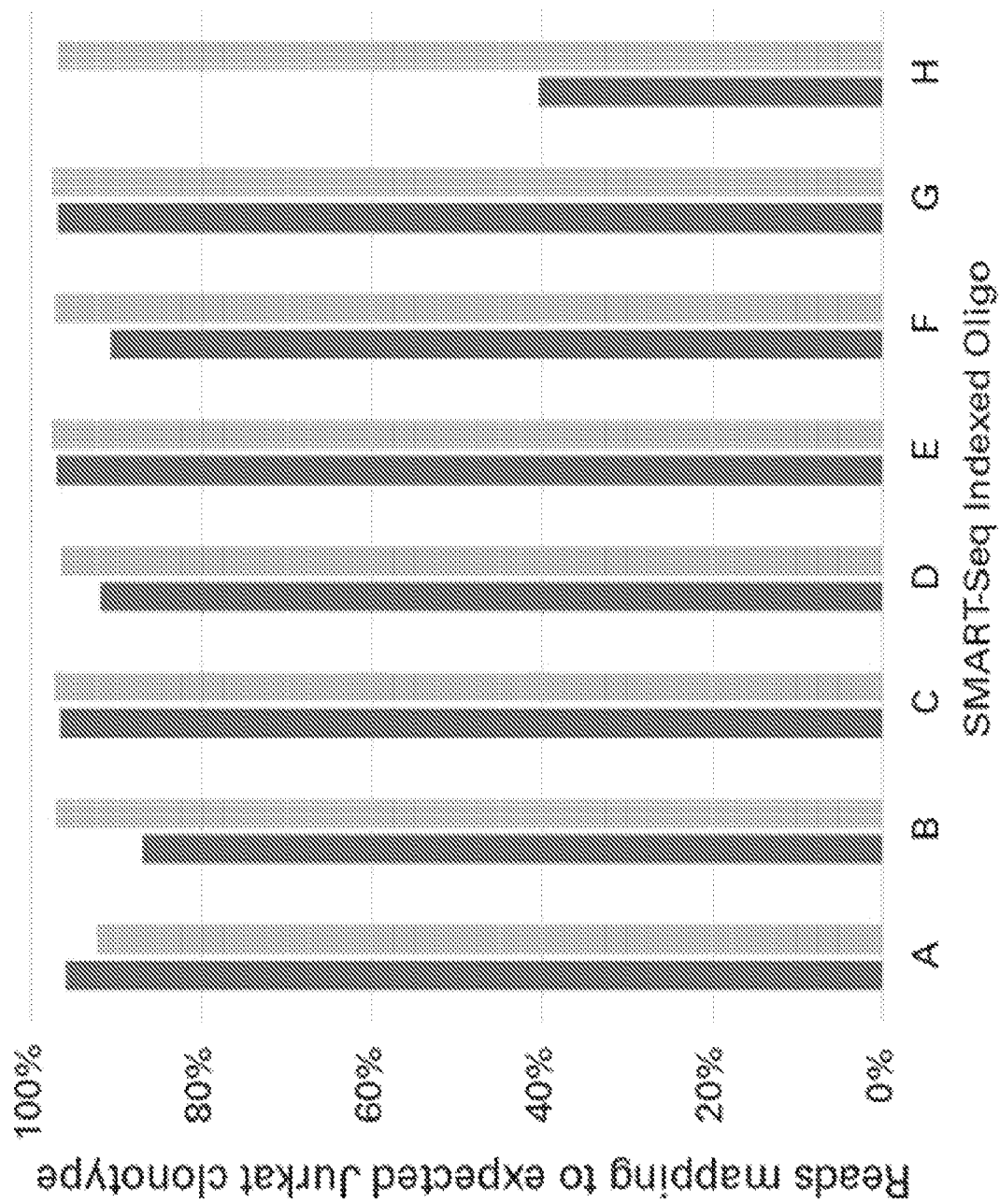
FIG. 9 provides further data testing the performance of an immune cell profiling workflow, showing the percentages of sequencing reads that map to the expected Jurkat clonotype.

The percentages of sequencing reads that map to the expected Jurkat clonotype (TRAV8-4, TRAJ3/TRBV12-3, TRBJ1-2) from each cell or RNA sample were also determined (FIG. 9). For each RNA sample, >92% of reads identified the correct Jurkat clonotype. For seven out of the eight cells analyzed, >86% of reads identified the correct Jurkat clonotype, in agreement with the read-alignment data.

In summary, testing of Jurkat cells in the 96-well format assay approach demonstrated that 92% of sequencing reads mapped to TCR sequences on average, while an average of 90% of reads identified the correct Jurkat clonotype Example 3

Figure 10:
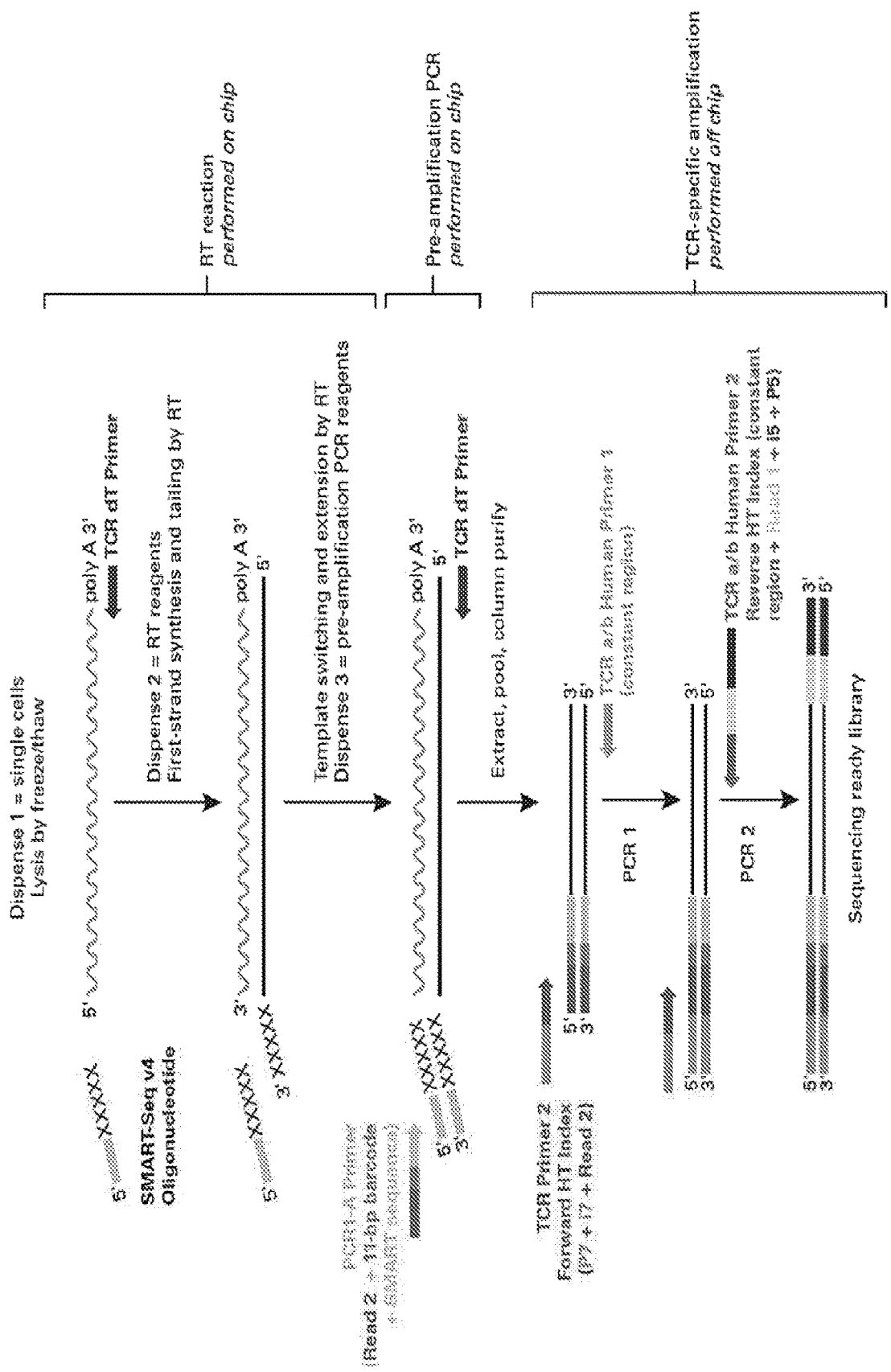
FIG. 10 provides a general schematic of a single cell TCR profiling workflow tested in a multi-sample nano-dispenser (MSND) format.

Single-Cell T-Cell Receptor Profiling Using the ICELL8 System a. Two-Primer Mediated cDNA Synthesis Single cell TCR profiling was also tested in a multi-sample nano-dispenser (MSND) format. A WaferGen (Fremont, CA) ICELL8® MSND system was utilized to dispense cells and reagents in nanoliter volumes into wells of an ICELL8® chip. The workflow is generally schematized in FIG. 10.

The on-chip reaction processes included three dispensing steps. In "Dispense #1" (single-cell solution), T cells were dispensed using MSND into WaferGen 72×72 chips with (or without) pre-printed, barcoded PCR primers, using methods designed to maximize the single-cell yield as dictated by Poisson statistics. Automated imaging of the cells was performed using CellSelect® software (Wafergen, Fremont CA). Single cell-containing wells were down-selected so each barcode was used only once. There were three copies of each barcode (n=1,728) on the chip that provide well-specific addresses. Cells were lysed on-chip by freeze-thaw and immediately processed.

In "Dispense #2" (RT mix) first-strand cDNA synthesis was primed by the TCR dT Primer and performed by an MMLV-derived reverse transcriptase (RT) in the presence of cell lysis buffer. Upon reaching the 5' end of each mRNA molecule, the RT added non-templated nucleotides to the first-strand cDNA. The SMART-SEQ v4 Oligonucleotide contains a sequence that is complementary to the non-templated nucleotides added by the RT, and hybridized to the first-strand cDNA. In the template-switching step, the RT used the remainder of the SMART-SEQ v4 template-switching oligo as a template for the incorporation of an additional sequence on the end of the first-strand cDNA.

In Dispense #3 (pre-amp mix) ten cycles of pre-amplification were performed to incorporate the pre-printed, PCR1-A Primer (used in concert with the TCR dT Primer). The contents of the chip are extracted by centrifugation using a fixture, followed by column purification.

PCR amplification reactions were performed in tubes. Full-length variable regions of TCR cDNA were selectively amplified by PCR using indexed primers that are complementary to the oligonucleotide-templated sequence (TCR primer 2 Forward HT Index), and the constant region(s) of TCR-α and/or TCR-β subunits (TCR α/β Human Primer 1). A subsequent round of PCR was performed to further amplify variable regions of TCR-α and/or TCR-β subunits and incorporate adapter sequences, using TCR Primer 2 Forward HT Index and TCR a/b Human Primer 2 Reverse HT Index. Included in the primers were adapter and index sequences (Read 2+i7+P7 and Read 1+i5+P5, respectively) that are compatible with the Illumina sequencing platform. Following purification, size selection, and quality analysis, TCR cDNA libraries were sequenced on the Illumina platform using 300 bp paired-end reads.

To evaluate the performance of the SMARTer® cDNA synthesis kit (Takara Bio USA, Mountain View, CA) the on-chip workflow, the sequencing data generated using the ICELL8® MSND System was analyzed for three independent library preparation runs. The protocol was initially performed on Jurkat cells and RNA control samples, and libraries were generated using a single barcode ((1) and (2)). Validation was then performed on pre-printed chips containing 1,728 barcodes. The resulting cDNA libraries were sequenced and then analyzed using MiXCR (Bolotin et al., (2015) Nat. Methods 12(5):380-381).

In the validation experiments where a single barcode was used, 1,471 Jurkat cells and either 6 or 48 PBMC RNA control wells were included in the final library. Both of these experiments gave good numbers of reads mapping to CDR3 regions in TCR-α or TCR-β (~84% and ~69% for run 1 (1) and run 2 (2), respectively), with the vast majority of these reads being used for clonotype calling. In (1), over 99% of the reads used for clonotype calling identified the correct Jurkat clonotype (TRAV8-4,TRAJ3/TRBV12-3,TRBJ1-2). In (2), where more PBMC RNA control samples were used, this number was ~95% (the remaining ~5% of reads identified alternative clonotypes present in the PBMC RNA controls).

The workflow on ICELL8® MSND chips pre-printed with 1,728 barcodes was then tested. In this experiment, 824 Jurkat cells, 10 Jurkat RNA controls, and 10 PBMC controls were included in the final library. In this case, ~67% of reads mapped to CDR3 regions in TCR-α or TCR-β. Over 99% of the reads used for clonotype calling identified the correct Jurkat clonotype (TRAV8-4,TRAJ3/TRBV12-3,TRBJ1-2), with good representation of both the alpha and beta chains. A summary of this data is provided in the table below:

|  | Single Barcode (1) | Single Barcode (2) | 1,728 Barcodes |
|---|---|---|---|
| Number of single-cell wells (Jurkat cells) | 1,471 | 1,471 | 824 |
| Number of control wells (RNA) | 6 | 48 | 10 + 10 |
| Total sequencing reads | 734,613 | 1,130,907 | 4,168,990 |
| Successfully aligned reads | 614,886 | 778,300 | 2,790,532 |
| Successfully aligned reads (percent) | 83.7% | 68.8% | 66.9% |
| Number of reads used in clonotype calling | 594,173 | 716,531 | 2,663,900 |
| Reads used (percent of total) | 80.9% | 63.4% | 63.9% |
| High-quality reads (percent of reads used) | 69.9% | 72.0% | 61.8% |
| Low-quality reads (percent of reads used) | 30.1% | 28.0% | 38.2% |
| Reads mapping to Jurkat clonotype: |  |  |  |
| TRAV8-4, TRAJ3 | 50.3% | 80.9% | 35.2% |
| TRBV12-3, TRBJ1-2 | 49.7% | 13.7% | 64.6% |
| TOTAL | 99.9% | 94.6% | 99.8% |

Figure 11:
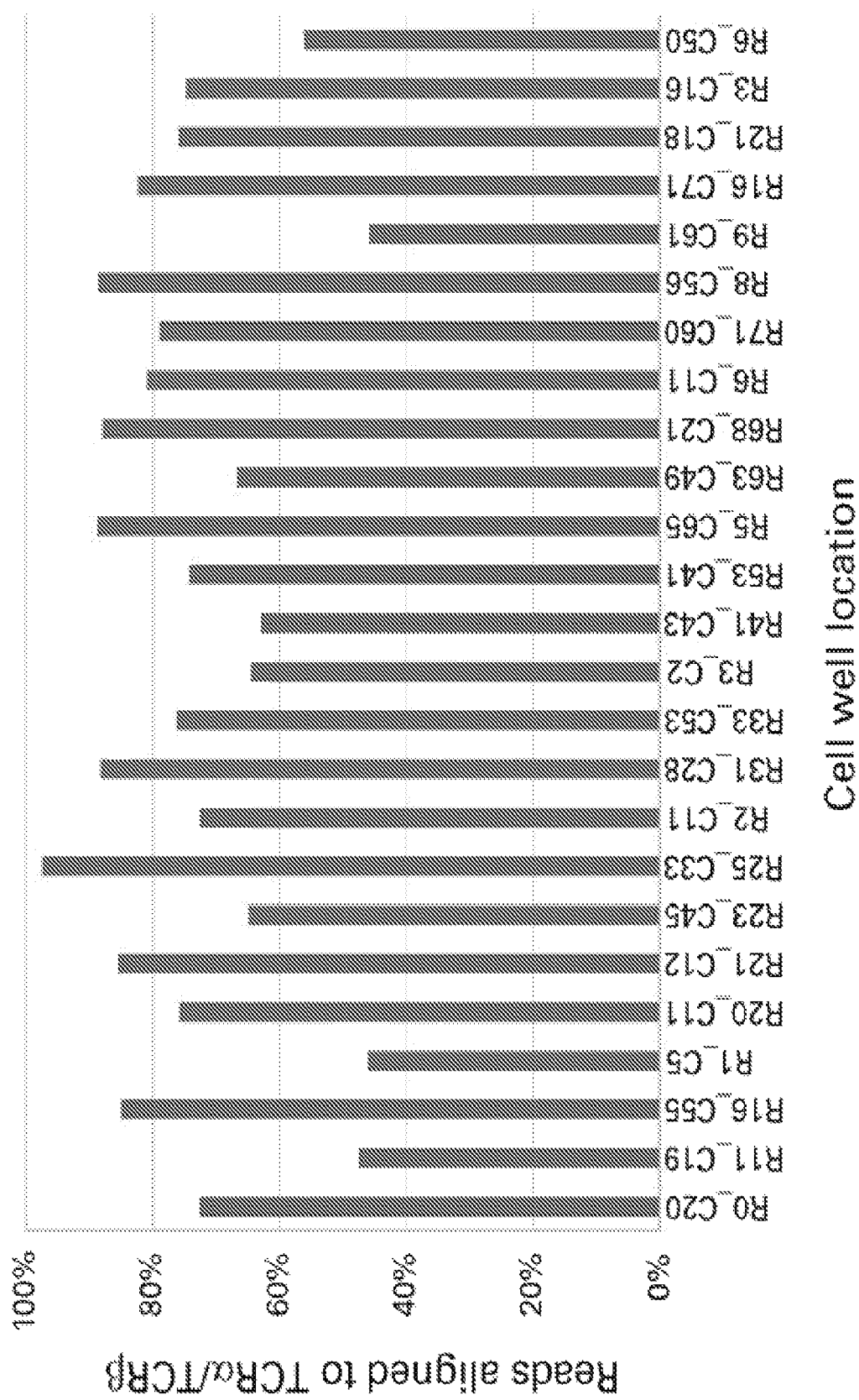
FIG. 11 provides the results of an alignment analysis of sequencing reads from single Jurkat cells mapped to CDR3 regions of TCR-α or TCR-β.

Alignment of sequencing reads from single Jurkat cells was further analyzed. Sequencing data for 25 randomly selected cells included in the experiment described above was analyzed to determine the percentages of sequencing reads that map to CDR3 regions in TCR-α or TCR-β. The results of this analysis are provide in FIG. 11, where "R" and "C" refer to row and column positions, respectively, for each cell. In the majority of cells (21/25), >60% of reads mapped to TCR-α or TCR-β sequences. The correct Jurkat clonotype (TRAV8-4,TRAJ3/TRBV12-3,TRBJ1-2) was identified for all cells. Data from control wells yielded a similar range of alignment rates.

The above demonstrates that single cell TCR profiling in MSND format can generate sequencing libraries for ~1,000 cells at a time and these libraries can be pooled together and successfully analyzed on a single run (e.g., a single MiSeq® run). Using this approach, analysis of individual Jurkat cells identified >60% of reads mapping to TCR sequences in most cells, with ~70-80% of these reads being used in clonotype identification.

b. Single-Primer Mediated cDNA Synthesis

FIGS. 12A-12D illustrate a variation on the above example where a single primer is employed to produce cDNA using an ICELL8® MSND system, which cDNA is further employed in accordance with embodiments of the invention. As in Example 3a, above, a WaferGen (Fremont, CA) ICELL8® MSND system is utilized to dispense cells and reagents in nanoliter volumes into wells of an ICELL8® MSND chip.

Figure 12A:
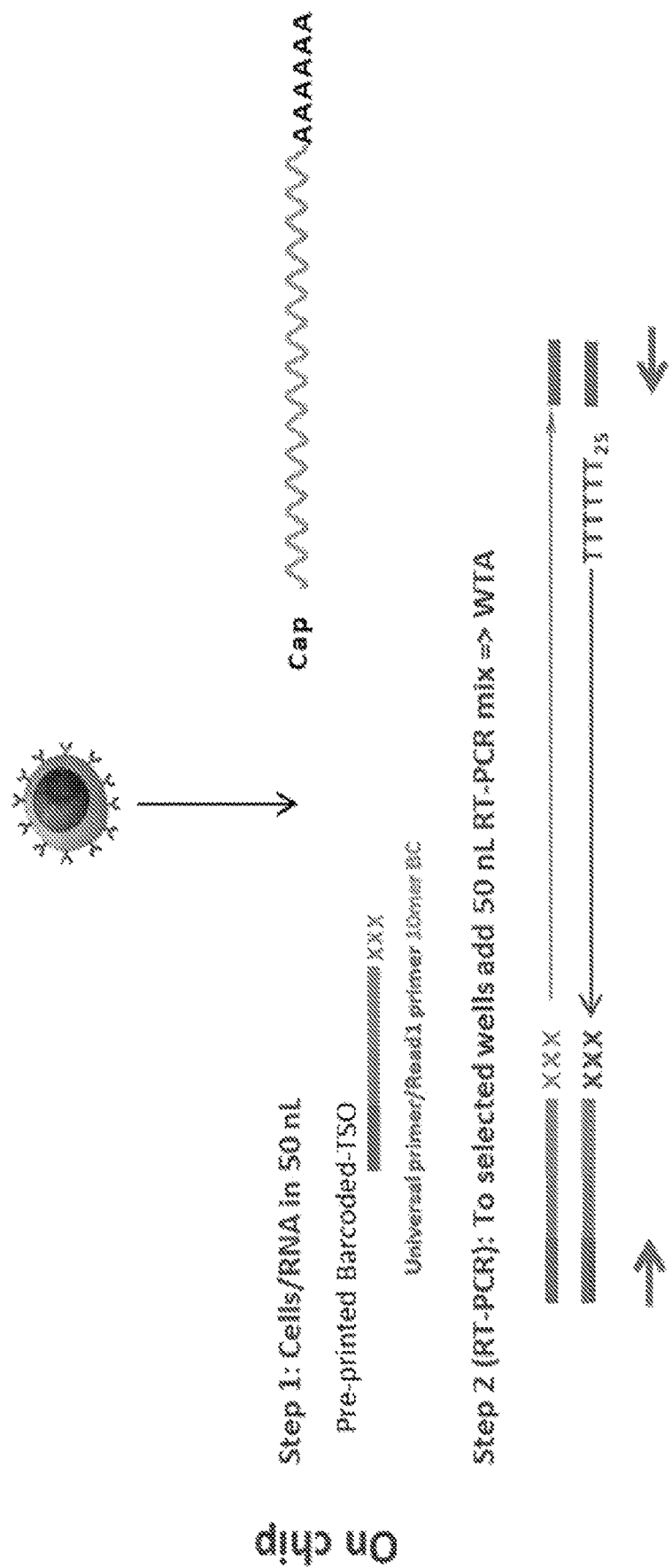
FIG. 12A-12D provide a general details of a single cell TCR profiling workflow tested in a multi-sample nano-dispenser (MSND) format according to an embodiment of the invention.
Figure 12B:
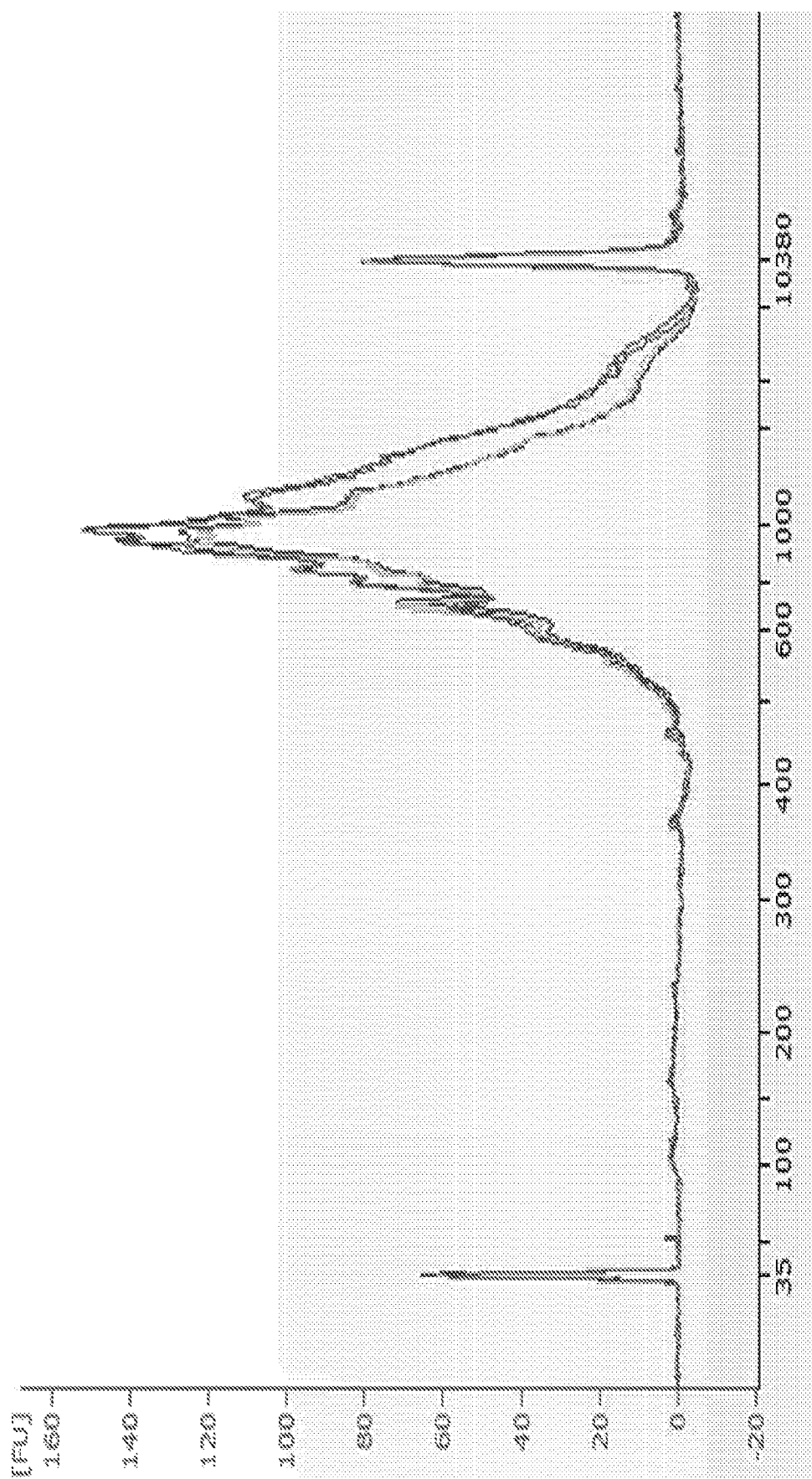

The on-chip reaction process illustrated in FIG. 12A includes three dispensing steps. In "Dispense #1" (single-cell solution), T cells are dispensed using dispenser of the MSND into WaferGen 72×72 SmartChip chips that include pre-printed, barcoded TSOs, using methods designed to maximize the single-cell yield as dictated by Poisson statistics. The barcoded TSO can comprise on or more primer binding sites and a barcode sequence. The barcode sequence can be a well barcode sequence that indicates the well from which the same originated on the 72×72 SmartChips. Automated imaging of the cells is performed using CellSelect® software. Wells containing single cells are down-selected so each barcode is used only once. Cells are lysed on-chip by freeze-thaw and immediately processed.

In "Dispense #2" (RT-PCR mix) first-strand cDNA synthesis is primed by the oligo dT Primer and performed by an MMLV-derived reverse transcriptase (RT) in the presence of cell lysis buffer. Upon reaching the 5' end of each mRNA molecule, the RT adds non-templated nucleotides to the first-strand cDNA. The preprinted TSO contains a sequence that is complementary to the non-templated nucleotides added by the RT, and hybridized to the first-strand cDNA. In the template-switching step, the RT uses the remainder of the TSO as a template for the incorporation of an additional sequence on the end of the first-strand cDNA.

In the illustrated protocol, the end sequences of the TSO and CDS are the same to enable single primer amplification for double-stranded cDNA synthesis. The TSO may contain one or more additional TSO-specific sequence, which can be, for example, a primer binding site, a UMI, a cell/sample barcode, and the like. While still on the chip the cDNA is amplified using a single primer, thereby generating a full length cDNA library (as shown in the bioanalyzer trace in FIG. 12B). The single primer can be a new primer or it can be the TSO and CDS primers used in reverse transcription.

Figure 12C:
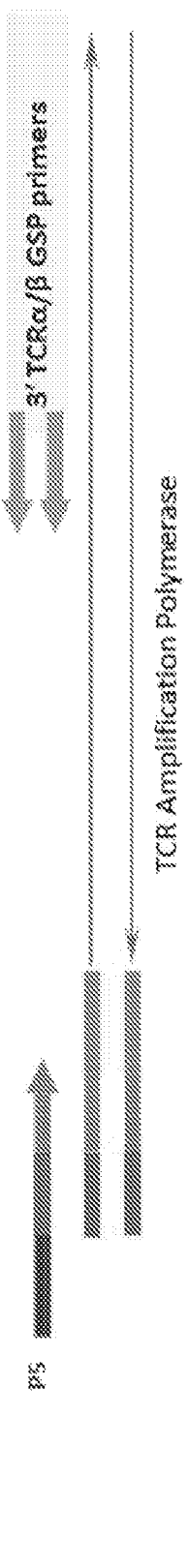
Figure 12C:
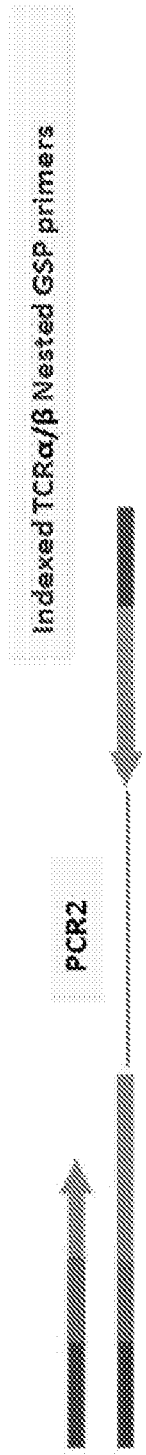
Figure 12D:
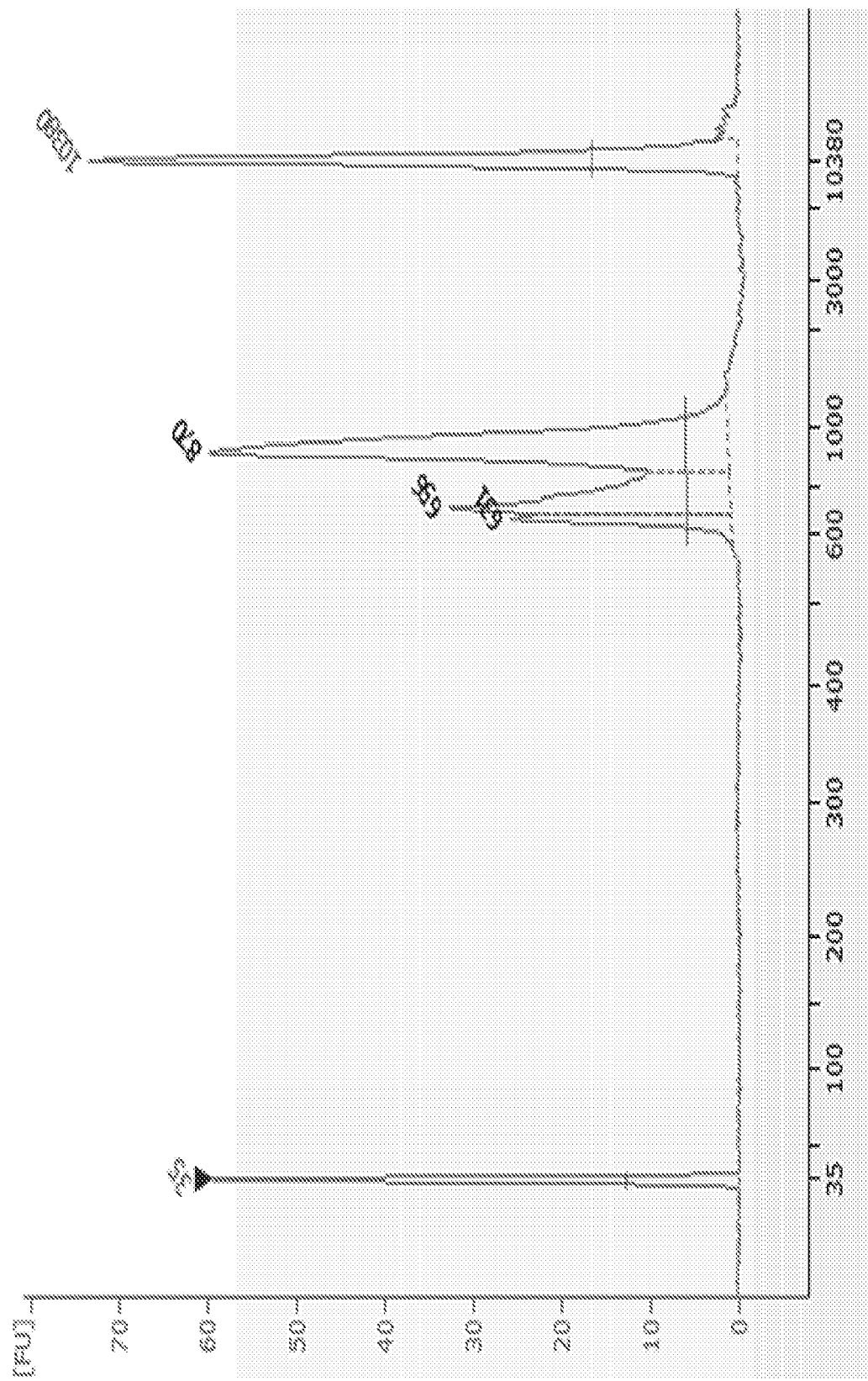

As illustrated in FIG. 12C, the samples are removed from the chip and pooled in an "Off chip" portion of the protocol. The pooled sample may then be split so as to generate two samples. One sample may be employed for generating an immune cell receptor repertoire sequencing library. The other sample may be employed for WTA or other gene specific amplification.

As illustrated, the sample for generating the immune cell receptor repertoire library may be amplified using a TCRα/β gene-specific primer and a TSO end specific primer. A second nested PCR amplification can occur as well. The amplification can produce a library containing both the TCR α and β receptor, as shown in the bioanalyzer trace in FIG. 12D.

In an example of an implementation of above protocol, two chips were dispensed with different T-cell lines. Chip 1 had 188 TALL-104 cells, two Positive control wells (Jurkat RNA—5 pg/well), and two Negative control wells. Chip 2 had 94 CCRF-CEM cells, 94 CCRF-CEM cells treated with PMA, two positive control wells (Jurkat RNA—5 pg/well), two negative control wells.

Figure 13:
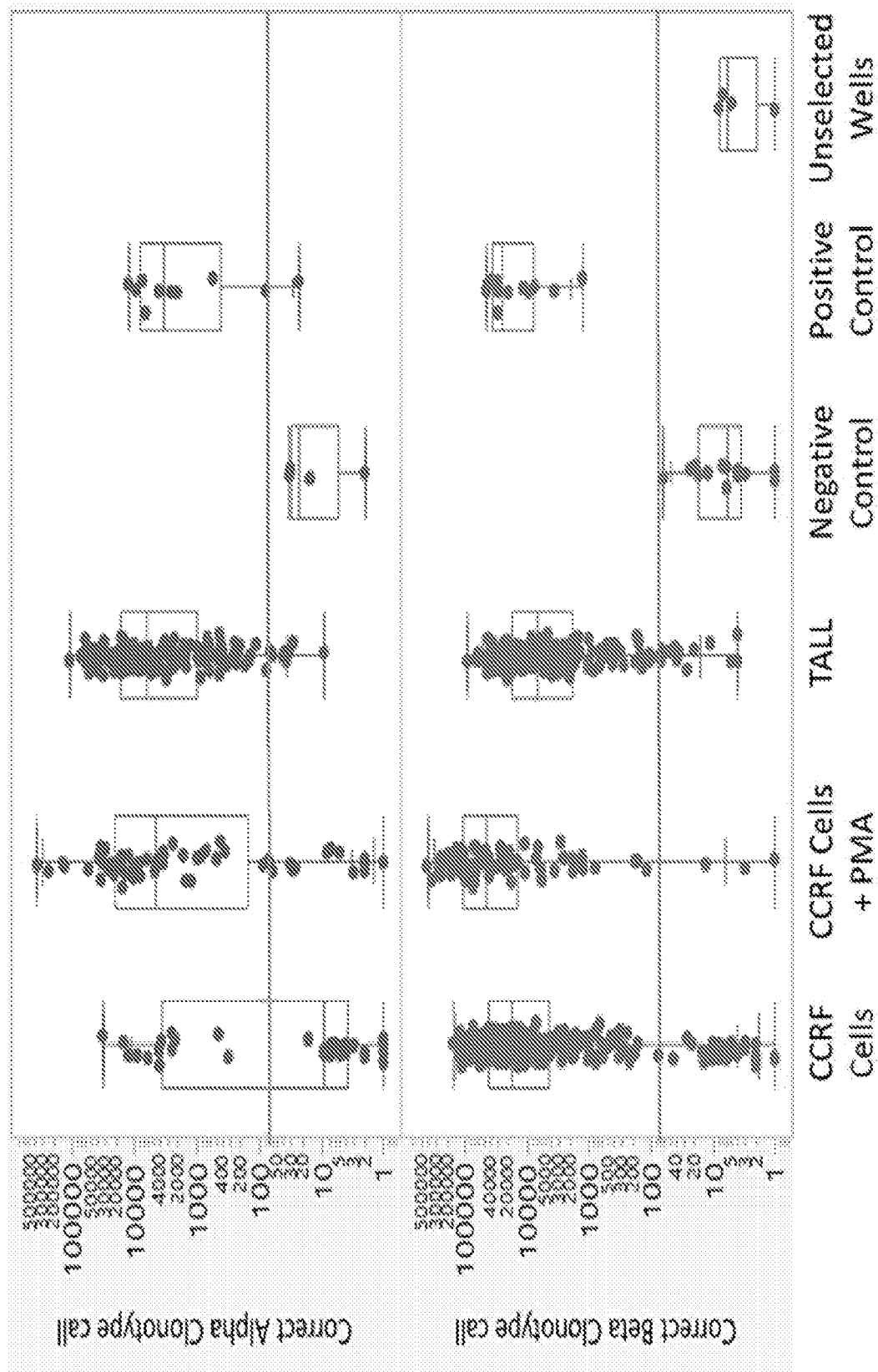
FIG. 13 depicts the α and β receptor read counts from an immune cell receptor sequencing library produced using the protocol of FIGS. 12A to 12D, as described in the Experimental Section, below.

The cells were sorted in an ICELL8® MSND system and subjected to the TCR amplification method as described above. Libraries were sequenced and analyzed. As shown in FIG. 13, TCR α and β receptors of the CCRF and TALL cells used in the experiments were able to be identified. CCRF cells treated with PMA also showed an increase in α and β receptor reads, indicating that the method can detect receptors in activated cells. As shown in FIG. 13, the MiXCR output was filtered using Excel to define a read threshold for both TCRα and TCRβ clonotypes (the solid line marks 80 read counts) greater than the 1× PBS negative controls. The data was analyzed using the JMP software and plotted into box plots where the lower bar represents 25th percentile and the upper bar the 75th percentile. Each dot represents TCRα and TCRβ clonotypes in a cell. On-chip negative controls were used to set thresholds to enable the distinction between samples and NTC or "junk" low-read clonotypes. The data generated from unstimulated and stimulated CCRF-CEM cells and Jurkat RNA (positive control) are shown. Induction of CCRF-CEM cells with phorbol myristate acetate (PMA) increases expression of the TCRα gene. CCRF-CEM data was generated using cells treated with and without PMA. Treatment of CCRF-CEM cells with PMA increased the call rate by four-fold (from 14% to 52%) based on TCRα and TCRβ clonotype data.

Figure 14A:
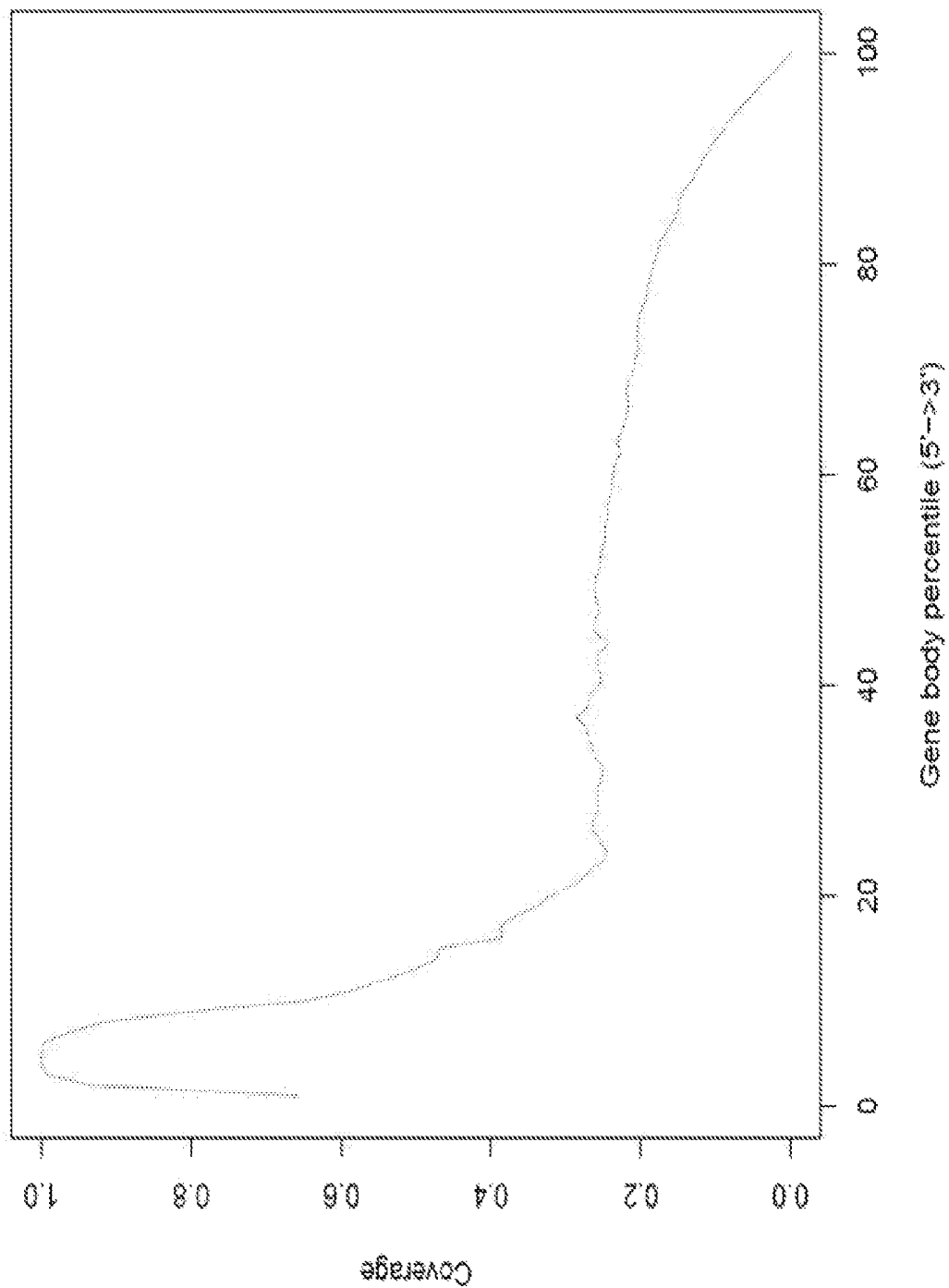
FIG. 14A-14B depict exemplary data from a split WTA library generated using the protocol of FIG. 12A-12D, as described in the Experimental Section, below.
Figure 14B:
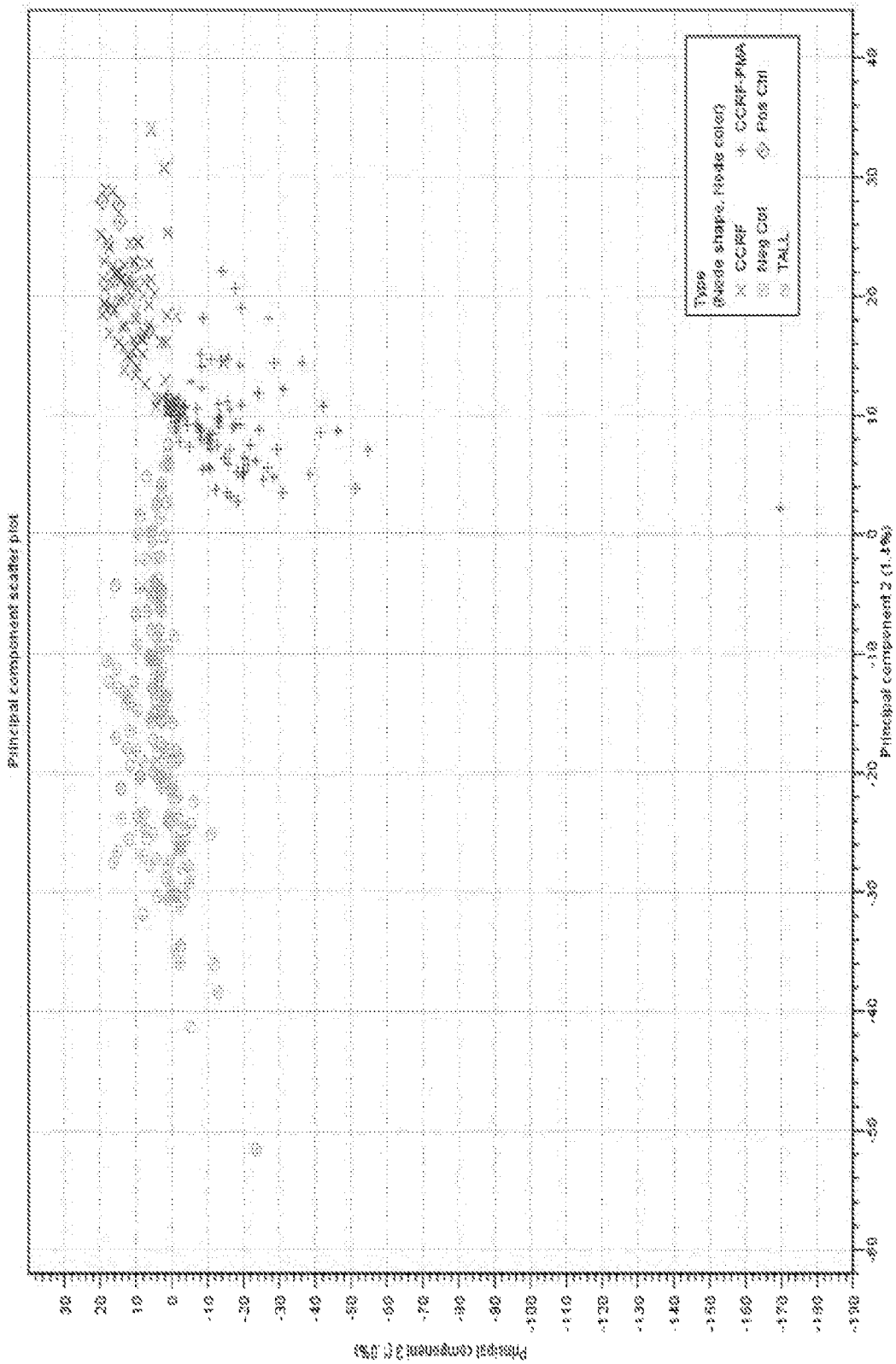

FIGS. 14A and 14B show successful whole transcriptome amplification (WTA) on a sample that was split from the initial amplified double-stranded cDNA sample produced according to the protocol of FIGS. 12A to 12D. The whole transcriptome amplification (WTA), generated by splitting the amplification reaction, was treated with the NEXTERA™ nucleic acid library preparation kit (Illumina) to fragment the amplicons and add adaptor sequences. The 5' end of the amplicons was amplified using a primer specific for the TSO-specific sequence (e.g., primer binding site) and a primer specific for the Nextera-introduced adaptor. 5' differential expression libraries were sequenced and analyzed for gene body coverage and principle genetic components. As shown in FIGS. 14A and B, the 5' DE library prep method adequately captured the 5' end of the amplicons and the different cell types were identified as well.

Notwithstanding the appended clauses, the disclosure is also defined by the following clauses:
1. A method of preparing an expression library and an immune cell receptor repertoire library from a ribonucleic acid (RNA) sample, the method comprising:
    (a) generating a product double stranded cDNA from a RNA sample using a template-switching reverse transcription reaction;

(b) splitting the generated product double stranded cDNA into a first reaction mixture and a second reaction mixture; and (c) end-capturing the product double stranded cDNA to produce an expression library from the first reaction mixture, and amplifying an immune cell-specific cDNA of the product double stranded cDNA to produce an immune cell receptor repertoire library from the second reaction mixture.

2. The method according to Clause 1, wherein the end-capturing and the amplifying occur simultaneously.

3. The method according to Clause 1, wherein the end-capturing and the amplifying occur sequentially.

4. The method according to any of the preceding clauses, wherein the RNA sample is obtained from a cellular sample.

5. The method according to any of Clauses 1 to 3, wherein the RNA sample is obtained from a single cell.

6. The method according to Clause 5, wherein the single cell is a T-cell.

7. The method according to Clause 5, wherein the single cell is a B-cell.

8. The method according to any of Clauses 5 to 7, wherein the method further comprises pooling product double stranded cDNA generated from a plurality of single cell RNA samples prior to the splitting.

9. The method according to any of Clauses 5 to 8, wherein a primer or oligonucleotide used in generating the product double stranded cDNA comprises an indexing sequence that identifies the single cell from which the product double stranded cDNA was produced.

10. The method according to Clause 9, wherein the primer or oligonucleotide is a template switching oligonucleotide.

11. The method according to any of Clauses 5 to 10, wherein the single cell is obtained from a biological sample.

12. The method according to Clause 11, wherein the method further comprises isolating the single cell using a cell sorter.

13. The method according to Clause 12, wherein the cell sorter is a flow cytometer.

14. The method according to Clause 12, wherein the cell sorter is a multi-well-based system.

15. The method according to any of the preceding clauses, wherein the expression library is a 5' end library.

16. The method according to any of Clauses 1 to 14, wherein the expression library is a 3' end library.

17. The method according to any of the preceding clauses, wherein the method further comprises sequencing the expression library and the immune cell receptor repertoire library.

18. The method according to Clause 17, wherein the method further comprises differential expression analysis of the sequenced expression library.

19. The method according to Clause 18, wherein the differential expression analysis comprises whole transcriptome analysis (WTA).

20. The method according to Clauses 18 or 19, wherein the differential expression analysis comprises targeted expression analysis.

21. The method according to Clause 20, wherein the targeted expression analysis comprises immune gene expression analysis.

22. The method according to any of the preceding clauses, wherein the immune cell receptor-specific cDNA comprises the 5' end of an immune cell receptor sequence.

23. The method according to any of the preceding clauses, wherein the immune cell receptor-specific cDNA comprises a full length immune cell receptor sequence.

24. The method according to any of the preceding clauses, wherein the amplifying comprises contacting the second reaction mixture with a 5' amplification primer and an immune cell receptor-specific amplification primer.

25. The method according to Clause 24, wherein the immune cell receptor-specific amplification primer specifically hybridizes to a constant region of one or more chains of an immune cell receptor.

26. The method according to Clause 25, wherein the immune cell receptor is a T-cell receptor (TCR).

27. The method according to Clauses 25 or 26, wherein the one or more chains is a TCR-α chain, a TCR-β chain or both.

28. The method according to Clause 25, wherein the immune cell receptor is a B-cell receptor (BCR).

29. The method according to Clauses 25 or 28, wherein the one or more chains is an immunoglobulin chain.

30. The method according to any of Clauses 24 to 29, wherein the immune cell receptor-specific amplification primer comprises one or more sequencing platform adapter constructs.

31. The method according to any of Clauses 24 to 30, wherein the 5' amplification primer comprises an indexing sequence.

32. The method according to any of Clauses 24 to 31, wherein the 5' amplification primer comprises one or more sequencing platform adapter constructs.

33. The method according to any of the preceding clauses, wherein the end-capturing comprises contacting the first reaction mixture with an end amplification primer.

34. The method according to Clause 33, wherein the end-capturing comprises 5' end-capture.

35. The method according to Clause 34, wherein the 5' end-capture comprises contacting the first reaction mixture with a 5' end amplification primer.

36. The method according to Clause 35, wherein the 5' end amplification primer comprises one or more sequencing platform adapter constructs.

37. The method according to Clause 33, wherein the end-capturing comprises 3' end-capture.

38. The method according to Clause 37, wherein the 3' end-capture comprises contacting the first reaction mixture with a 3' end amplification primer.

39. The method according to Clause 38, wherein the 3' end amplification primer comprises one or more sequencing platform adapter constructs.

40. The method according to any of the preceding clauses, wherein the end-capturing comprises tagmenting to add a post-tagmentation amplification primer binding domain to the product double stranded cDNA.

41. The method according to Clause 40, wherein the tagmenting comprises amplifying the product double stranded cDNA using an end amplification primer and a post-tagmentation amplification primer that hybridizes to the post-tagmentation amplification primer binding domain.

42. The method according to Clauses 40 or 41, wherein the tagmenting further comprises contacting the product double stranded cDNA with a Tn5 transposase.

43. The method according to any of the preceding clauses, wherein generating the product double stranded cDNA comprises combining:

the RNA sample;
a first strand complementary deoxyribonucleic acid (cDNA) primer;
a template switch oligonucleotide comprising a 3' hybridization domain and a 5' adapter sequence binding domain;
a reverse transcriptase; and
dNTPs;
in a reaction mixture under conditions sufficient to produce the product double stranded cDNA.

44. The method according to any of the preceding clauses, wherein the method further comprises sequencing genomic DNA (gDNA) of the single cell.

45. The method according to Clause 44, wherein the method further comprises isolating the gDNA of the single cell prior to the sequencing.

46. The method according to Clauses 44 or 45, wherein sequencing gDNA of the single cell comprises immune locus specific sequencing.

47. The method according to Clause 46, wherein the immune locus specific sequencing comprises T-cell receptor (TCR) locus specific sequencing.

48. The method according to Clauses 46 or 47, wherein the immune locus specific sequencing comprises B-cell receptor (BCR) locus specific sequencing.

49. The method according to any of Clauses 44 to 48, wherein sequencing gDNA of the single cell comprises whole genome sequencing.

50. The method according to any of the preceding clauses, wherein the expression library is a full length expression library.

51. A kit comprising:
a 5' amplification primer;
an immune cell receptor-specific amplification primer; and
an end amplification primer.

52. The kit according to Clause 51, wherein the kit further comprises a poly(dT) primer.

53. The kit according to Clauses 51 or 52, wherein the 5' amplification primer comprises an indexing sequence.

54. The kit according to any of Clauses 51 to 53, wherein the 5' amplification primer comprises one or more sequencing platform adapter constructs.

55. The kit according to any of Clauses 51 to 54, wherein the immune cell receptor-specific amplification primer comprises an indexing sequence.

56. The kit according to any of Clauses 51 to 55, wherein the immune cell receptor-specific amplification primer comprises one or more sequencing platform adapter constructs.

57. The kit according to any of Clauses 51 to 56, wherein the end amplification primer comprises an indexing sequence.

58. The kit according to any of Clauses 51 to 57, wherein the end amplification primer comprises one or more sequencing platform adapter constructs.

59. The kit according to any of Clauses 51 to 58, wherein the end amplification primer is a 5' end amplification primer.

60. The kit according to any of Clauses 51 to 58, wherein the end amplification primer is a 3' end amplification primer.

61. The kit according to any of Clauses 51 to 60, wherein the kit further comprises one or more components for performing a template-switching reverse transcription reaction comprising a template switching oligonucleotide comprising a 5' adapter sequence.

62. The kit according to Clause 61, wherein the 5' amplification primer comprises the 5' adapter sequence or the complement thereof.

63. The kit according to Clauses 61 or 62, wherein the end amplification primer comprises the 5' adapter sequence or the complement thereof.

64. The kit according to any of Clauses 51 to 63, wherein the kit comprises a second 5' amplification primer comprising a sequence identical to a 5' portion of the 5' amplification primer.

65. The kit according to any of Clauses 51 to 64, wherein the kit comprises a second immune cell receptor-specific amplification primer comprising a sequence identical to a portion of the immune cell receptor-specific amplification primer.

66. The kit according to Clause 65, wherein the portion is a 5' portion of the immune cell receptor-specific amplification primer.

67. The kit according to Clause 65, wherein the portion is a 3' portion of the immune cell receptor-specific amplification primer.

68. The kit according to any of Clauses 51 to 67, wherein the kit further comprises one or more components for performing a tagmentation reaction.

69. The kit according to Clause 68, wherein the one or more components for performing a tagmentation reaction comprise:
a transposon nucleic acid comprising a post-tagmentation amplification primer binding domain;
a post-tagmentation amplification primer that hybridizes to the post-tagmentation amplification primer binding domain;
a transposase; or
a combination thereof.

70. The kit according to Clause 69, wherein the transposase is a Tn5 transposase.

71. A method of preparing an immune cell receptor repertoire library from a plurality of single cells, the method comprising:
(a) isolating an RNA sample from each single cell of the plurality;
(b) generating an indexed product double stranded cDNA from the RNA sample using a template-switching reverse transcription reaction;
(c) pooling the generated indexed product double stranded cDNAs;
(d) amplifying immune cell-specific cDNAs of the indexed product double stranded cDNAs to produce an immune cell receptor repertoire library comprising single cell indexed immune cell-specific cDNAs.

72. The method according to Clause 71, wherein the single cell is a T-cell.

73. The method according to Clause 71, wherein the single cell is a B-cell.

74. The method according to any of Clauses 71 to 73, wherein a primer or oligonucleotide used in generating the indexed product double stranded cDNA comprises an indexing sequence that identifies the single cell.

75. The method according to Clause 74, wherein the primer or oligonucleotide is a template switching oligonucleotide.

76. The method according to Clause 74, wherein the primer or oligonucleotide is a 5' amplification primer comprising a sequence that is identical to a 5' portion of a template switching oligonucleotide used in the template-switching reverse transcription reaction.

77. The method according to any of Clauses 71 to 76, wherein the indexed immune cell receptor-specific cDNAs comprise the 5' end of immune cell receptor sequences.

78. The method according to any of Clauses 71 to 77, wherein the indexed immune cell receptor-specific cDNAs comprise full length immune cell receptor sequences.

79. The method according to any of Clauses 71 to 78, wherein the amplifying comprises contacting the pooled indexed product double stranded cDNAs with a 5' amplification primer and an immune cell receptor-specific amplification primer.

80. The method according to Clause 79, wherein the immune cell receptor-specific amplification primer specifically hybridizes to a constant region of one or more chains of an immune cell receptor.

81. The method according to Clause 80, wherein the immune cell receptor is a T-cell receptor (TCR).

82. The method according to Clause 81, wherein the one or more chains is a TCR-α chain, a TCR-β chain or both.

83. The method according to Clause 80, wherein the immune cell receptor is a B-cell receptor (BCR).

84. The method according to Clause 83, wherein the one or more chains is an immunoglobulin chain.

85. The method according to any of Clauses 79 to 84, wherein the immune cell receptor-specific amplification primer comprises one or more sequencing platform adapter constructs.

86. The method according to any of Clauses 79 to 85, wherein the 5' amplification primer comprises an indexing sequence.

87. The method according to any of Clauses 79 to 86, wherein the 5' amplification primer comprises one or more sequencing platform adapter constructs.

88. The method according to any of Clauses 79 to 87, wherein the single cell is obtained from a biological sample.

89. The method according to Clause 88, wherein the method further comprises isolating the single cell using a cell sorter.

90. The method according to Clause 89, wherein the cell sorter is a flow cytometer.

91. The method according to Clause 89, wherein the cell sorter is a multi-well-based system.

92. The method according to any of Clauses 71 to 91, wherein the method further comprises sequencing genomic DNA (gDNA) of the single cell.

93. The method according to Clause 92, wherein the method further comprises isolating the gDNA of the single cell prior to the sequencing.

94. The method according to Clauses 92 or 93, wherein sequencing gDNA of the single cell comprises immune locus specific sequencing.

95. The method according to Clause 94, wherein the immune locus specific sequencing comprises T-cell receptor (TCR) locus specific sequencing.

96. The method according to Clauses 94 or 95, wherein the immune locus specific sequencing comprises B-cell receptor (BCR) locus specific sequencing.

97. The method according to any of Clauses 92 to 96, wherein sequencing gDNA of the single cell comprises whole genome sequencing.

98. The method according to any of Clauses 71 to 97, wherein the method further comprises sequencing the immune cell receptor repertoire library.

99. A kit comprising:
a template switching oligonucleotide comprising a 5' adapter sequence;
a 5' amplification primer comprising the 5' adapter sequence; and
an immune cell receptor-specific amplification primer.

100. The kit according to Clause 99, wherein the template switching oligonucleotide comprises an indexing sequence.

101. The kit according to Clauses 99 or 100, wherein the 5' amplification primer comprises an indexing sequence.

102. The kit according to any of Clauses 99 to 101, wherein the 5' amplification primer comprises one or more sequencing platform adapter constructs.

103. The kit according to any of Clauses 99 to 102, wherein the immune cell receptor-specific amplification primer comprises an indexing sequence.

104. The kit according to any of Clauses 99 to 103, wherein the immune cell receptor-specific amplification primer comprises one or more sequencing platform adapter constructs.

105. The kit according to any of Clauses 99 to 104, wherein the kit further comprises a poly(dT) primer.

106. The kit according to any of Clauses 99 to 105, wherein the kit further comprises one or more components for performing a template-switching reverse transcription reaction in addition to the template switching oligonucleotide.

107. The kit according to any of Clauses 99 to 106, wherein the kit comprises a second 5' amplification primer.

108. The kit according to Clause 107, wherein the second 5' amplification primer comprises one or more sequencing platform adapter constructs.

109. The kit according to Clauses 107 or 108, wherein the second 5' amplification primer comprises a sequence identical to a 5' portion of the 5' amplification primer.

110. The kit according to any of Clauses 107 to 109, wherein the kit further comprises a third 5' amplification primer.

111. The kit according to Clause 110, wherein the third 5' amplification primer comprises one or more sequencing platform adapter constructs.

112. The kit according to Clauses 110 or 111, wherein the third 5' amplification primer comprises a sequence identical to a 5' portion of the second 5' amplification primer.

113. The kit according to Clauses 107 or 108, wherein the second 5' amplification primer comprises a sequence that hybridizes to a primer binding site present in a 5' non-templated sequence attached to the 5' amplification primer.

114. The kit according to any of Clauses 99 to 113, wherein the kit comprises a second immune cell receptor-specific amplification primer comprising a sequence identical to a portion of the immune cell receptor-specific amplification primer.

115. The kit according to any of Clauses 99 to 114, wherein the portion is a 5' portion of the immune cell receptor-specific amplification primer.

116. The kit according to any of Clauses 99 to 114, wherein the portion is a 3' portion of the immune cell receptor-specific amplification primer.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of preparing an expression library and an immune cell receptor repertoire library from a ribonucleic acid (RNA) sample obtained from a single cell, the method comprising:
   (a) generating a product double stranded cDNA from an RNA sample obtained from a single cell using a template-switching reverse transcription reaction;
   (b) splitting the generated product double stranded cDNA into a first reaction mixture and a second reaction mixture; and
   (c) producing an expression library from the first reaction mixture and an immune cell receptor repertoire library from the second reaction mixture; wherein:
      (i) producing the expression library comprises employing an end amplification primer in an end-capture method, wherein the end amplification primer hybridizes to a non-template sequence and amplifies from an end introduced in the product double stranded cDNA; and
      (ii) producing the immune cell receptor repertoire library comprises amplifying an immune cell receptor-specific cDNA with an immune cell receptor-specific amplification primer and a 5' amplification primer.

2. The method according to claim 1, wherein the single cell is a T-cell or a B-cell.

3. The method according to claim 1, wherein the method further comprises pooling product double stranded cDNA generated from a plurality of single cell RNA samples prior to the splitting.

4. The method according to claim 1, wherein a primer or oligonucleotide used in generating the product double stranded cDNA comprises an indexing sequence that identifies the single cell from which the product double stranded cDNA was produced.

5. The method according to claim 4, wherein the primer or oligonucleotide is a template switching oligonucleotide.

6. The method according to claim 1, wherein the method further comprises sequencing the expression library and the immune cell receptor repertoire library.

7. The method according to claim 6, wherein sequencing comprises subjecting the expression library and the immune cell receptor repertoire library to a next generation sequencing (NGS) protocol.

8. The method according to claim 6, wherein the method further comprises differential expression analysis of the sequenced expression library.

9. The method according to claim 1, wherein the immune cell receptor-specific amplification primer specifically hybridizes to a constant region of one or more chains of an immune cell receptor.

10. The method according to claim 9, wherein the immune cell receptor is a T-cell receptor (TCR) or a B-cell receptor (BCR).

11. The method according to claim 1, wherein generating the product double stranded cDNA comprises combining:
   the RNA sample;
   a first strand complementary deoxyribonucleic acid (cDNA) primer;
   a template switch oligonucleotide comprising a 3' hybridization domain and a 5' adapter sequence binding domain;
   a reverse transcriptase; and
   dNTPs;
   in a reaction mixture under conditions sufficient to produce the product double stranded cDNA.

12. The method according to claim 11, wherein the reverse transcriptase is selected from the group consisting of: retroviral reverse transcriptase, retrotransposon reverse transcriptase, retroplasmid reverse transcriptases, retron reverse transcriptases, bacterial reverse transcriptases, group II intron-derived reverse transcriptase, and functional fragments thereof.

13. The method according to claim 11, wherein the reverse transcriptase has terminal transferase activity.

14. The method according to claim 13, wherein the reverse transcriptase is a Moloney Murine Leukemia reverse transcriptase (MMLV RT).

15. The method according to claim 1, wherein the end-capture method comprises tagmenting the product double stranded cDNA with a transposome to produce a tagmented sample and contacting the tagmented sample with the end amplification primer, wherein the transposome comprises a transposase and a transposon nucleic acid, and wherein the transposon nucleic acid comprises a transposon end domain and an amplification primer binding domain.

16. The method according to claim 15, wherein the end amplification primer comprises one or more sequencing platform adapter constructs.

17. The method according to claim 15, wherein the end amplification primer is employed to amplify from a tagmentation generated end of the tagmented sample.

18. The method according to claim 17, wherein the end amplification primer binds to the amplification primer binding domain.

19. The method according to claim 1, wherein the expression library is a next generation sequencing (NGS) ready library.

20. The method according to claim 1, wherein the immune cell receptor repertoire library is a next generation sequencing (NGS) ready library.

21. The method according to claim 1, wherein the immune cell receptor-specific cDNA comprises the 5' end of an immune cell receptor sequence.

22. The method according to claim 1, wherein the immune cell receptor-specific amplification primer comprises one or more sequencing platform adapter constructs.

23. The method according to claim 1, wherein the 5' amplification primer comprises one or more sequencing platform adapter constructs.

24. The method according to claim 1, wherein the end amplification primer binds to a primer binding site added in the end-capture method.

25. The method according to claim 1, wherein the expression library comprises sequences complementary to different species of target nucleic acids in the RNA sample.

26. The method according to claim 25, wherein the expression library is a high complexity library comprising sequences complementary to 70% or more of the different species of target nucleic acids in the RNA sample.

27. A method of preparing an expression library and an immune cell receptor repertoire library from a ribonucleic acid (RNA) sample obtained from a single cell, the method comprising:
- (a) generating a product double stranded cDNA from an RNA sample obtained from a single cell using a template-switching reverse transcription reaction;
- (b) splitting the generated product double stranded cDNA into a first reaction mixture and a second reaction mixture; and
- (c) producing an expression library from the first reaction mixture and an immune cell receptor repertoire library from the second reaction mixture; wherein:
- (i) producing the expression library comprises employing an end amplification primer in an end-capture method, wherein the end-capture method comprises tagmenting the product double stranded cDNA with a transposome to produce a tagmented sample and contacting the tagmented sample with the end amplification primer, and wherein the end amplification primer hybridizes to a non-template sequence and amplifies from an end introduced in the product double stranded cDNA; and
- (ii) producing the immune cell receptor repertoire library comprises amplifying an immune cell receptor-specific cDNA with an immune cell receptor-specific amplification primer and a 5' amplification primer, wherein the immune cell receptor repertoire library includes sequences of one or more types of immune receptors of a cell or a population of cells.

* * * * *

UNITED STATES PATENT AND TRADEMARK OFFICE
CERTIFICATE OF CORRECTION

PATENT NO. : 12,065,644 B2
APPLICATION NO. : 16/465134
DATED : August 20, 2024
INVENTOR(S) : Magnolia Bostick et al.

It is certified that error appears in the above-identified patent and that said Letters Patent is hereby corrected as shown below:

In the Specification

Please replace "that that" with -- that -- (Column 6, Line 9).

Please replace "singlecells" with -- single cells -- (Column 13, Line 26).

Please replace "07) ;" with -- 07 ; -- (Column 15, Line 54).

Please replace "multiwell" with -- multi-well -- (Column 23, Line 29).

Please replace "(Wafergen," with -- (WaferGen, -- (Column 23, Line 32).

Please replace "the a" with -- a -- (Column 25, Line 61).

Please replace "fg/µL" with -- µg/µL -- (Column 25, Line 61).

Please replace "rerio)," with -- rerio)), -- (Column 29, Line 9).

Please replace "multi well" with -- multi-well -- (Column 31, Line 1).

Please replace "sequences," with -- sequences. -- (Column 36, Line 40).

Please replace "the a" with -- a -- (Column 39, Line 8).

Please replace "etc.), etc.)," with -- etc.), -- (Column 41, Line 64).

Please replace "E Z et. al," with -- EZ et. al, -- (Column 45, Line 18).

Signed and Sealed this
Twenty-ninth Day of October, 2024

Katherine Kelly Vidal
*Director of the United States Patent and Trademark Office*

Please replace "clonotype" with -- clonotype. -- (Column 49, Line 14).

Please replace "(Wafergen," with -- (WaferGen, -- (Column 49, Line 35).

```
                        SEQUENCE LISTING

<160> NUMBER OF SEQ ID NOS: 22

<210> SEQ ID NO 1
<211> LENGTH: 142
<212> TYPE: PRT
<213> ORGANISM: Homo sapiens

<400> SEQUENCE: 1

Pro Asn Ile Gln Asn Pro Asp Pro Ala Val Tyr Gln Leu Arg Asp Ser
1               5                  10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

<210> SEQ ID NO 2
<211> LENGTH: 429
<212> TYPE: DNA
<213> ORGANISM: Homo sapiens

<400> SEQUENCE: 2
ccaaatatcc agaaccctga ccctgccgtg taccagctga gagactctaa atccagtgac        60
aagtctgtct gcctattcac cgattttgat tctcaaacaa atgtgtcaca aagtaaggat       120
tctgatgtgt atatcacaga caaaactgtg ctagacatga ggtctatgga cttcaagagc       180
aacagtgctg tggcctggag caacaaatct gactttgcat gtgcaaacgc cttcaacaac       240
agcattattc cagaagacac cttcttcccc agcccagaaa gttcctgtga tgtcaagctg       300
gtcgagaaaa gctttgaaac agatacgaac ctaaactttc aaaacctgtc agtgattggg       360
ttccgaatcc tcctcctgaa agtggccggg tttaatctgc tcatgacgct gcggctgtgg       420
tccagctga                                                               429
```

<210> SEQ ID NO 3
<211> LENGTH: 138
<212> TYPE: PRT
<213> ORGANISM: Mus musculus

<400> SEQUENCE: 3

Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
    50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro Cys Asp Ala Thr Leu
                85                  90                  95

Thr Glu Lys Ser Phe Glu Thr Asp Met Asn Leu Asn Phe Gln Asn Leu
            100                 105                 110

Ser Val Met Gly Leu Arg Ile Leu Leu Leu Lys Val Ala Gly Phe Asn
        115                 120                 125

Leu Leu Met Thr Leu Arg Leu Trp Ser Ser
    130                 135

<210> SEQ ID NO 4
<211> LENGTH: 138
<212> TYPE: PRT
<213> ORGANISM: Mus musculus

<400> SEQUENCE: 4

Pro Asn Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
    50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro Cys Asp Ala Thr Leu
                85                  90                  95

Thr Glu Lys Ser Phe Glu Thr Asp Met Asn Leu Asn Phe Gln Asn Leu
            100                 105                 110

Ser Val Met Gly Leu Arg Ile Leu Leu Leu Lys Val Ala Gly Phe Asn
        115                 120                 125

Leu Leu Met Thr Leu Arg Leu Trp Ser Ser
    130                 135

<210> SEQ ID NO 5
<211> LENGTH: 414
<212> TYPE: DNA
<213> ORGANISM: Mus musculus

<400> SEQUENCE: 5
ccatacatcc agaacccaga acctgctgtg taccagttaa aagatcctcg gtctcaggac      60

```
agcaccctct gcctgttcac cgactttgac tcccaaatca atgtgccgaa aaccatggaa      120
tctggaacgt tcatcactga caaaactgtg ctggacatga agctatgga ttccaagagc      180 aatggggcca ttgcctggag caaccagaca agcttcacct gccaagatat cttcaaagag      240
accaacgcca cctaccccag ttcagacgtt ccctgtgatg ccacgttgac cgagaaaagc      300
tttgaaacag atatgaacct aaactttcaa aacctgtcag ttatgggact ccgaatcctc      360
ctgctgaaag tagcgggatt taacctgctc atgacgctga ggctgtggtc cagt            414

<210> SEQ ID NO 6
<211> LENGTH: 414
<212> TYPE: DNA
<213> ORGANISM: Mus musculus

<400> SEQUENCE: 6
ccaaacatcc agaacccaga acctgctgtg taccagttaa agatcctcg gtctcaggac       60 agcaccctct gcctgttcac cgactttgac tcccaaatca atgtgccgaa aaccatggaa      120
tctggaacgt tcatcactga caaaactgtg ctggacatga agctatgga ttccaagagc      180 aatggggcca ttgcctggag caaccagaca agcttcacct gccaagatat cttcaaagag      240
accaacgcca cctaccccag ttcagacgtt ccctgtgatg ccacgttgac cgagaaaagc      300
tttgaaacag atatgaacct aaactttcaa aacctgtcag ttatgggact ccgaatcctc      360
ctgctgaaag tagcgggatt taacctgctc atgacgctga ggctgtggtc cagt            414

<210> SEQ ID NO 7
<211> LENGTH: 177
<212> TYPE: PRT
<213> ORGANISM: Homo sapiens

<400> SEQUENCE: 7

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 8
<211> LENGTH: 531
<212> TYPE: DNA
<213> ORGANISM: Homo sapiens

<400> SEQUENCE: 8

```
gaggacctga acaaggtgtt cccacccgag gtcgctgtgt ttgagccatc agaagcagag      60
atctcccaca cccaaaaggc cacactggtg tgcctggcca caggcttctt ccccgaccac     120
gtggagctga gctggtgggt gaatgggaag gaggtgcaca gtggggtcag cacagacccg     180
cagcccctca aggagcagcc cgccctcaat gactccagat actgcctgag cagccgcctg     240
agggtctcgg ccaccttctg gcagaacccc cgcaaccact ccgctgtca agtccagttc      300
tacgggctct cggagaatga cgagtggacc caggataggg ccaaacccgt cacccagatc     360
gtcagcgccg aggcctgggg tagagcagac tgtggcttta cctcggtgtc ctaccagcaa     420
ggggtcctgt ctgccaccat cctctatgag atcctgctag ggaaggccac cctgtatgct     480
gtgctggtca gcgcccttgt gttgatggcc atggtcaaga gaaaggattt c              531
```

<210> SEQ ID NO 9
<211> LENGTH: 178
<212> TYPE: PRT
<213> ORGANISM: Homo sapiens

<400> SEQUENCE: 9

```
Asp Leu Lys Asn Val Phe Pro Pro Glu Val Ala Val Phe Glu Pro Ser
1               5                   10                  15
Glu Ala Glu Ile Ser His Thr Gln Lys Ala Thr Leu Val Cys Leu Ala
            20                  25                  30
Thr Gly Phe Tyr Pro Asp His Val Glu Leu Ser Trp Trp Val Asn Gly
        35                  40                  45
Lys Glu Val His Ser Gly Val Ser Thr Asp Pro Gln Pro Leu Lys Glu
    50                  55                  60
Gln Pro Ala Leu Asn Asp Ser Arg Tyr Cys Leu Ser Ser Arg Leu Arg
65                  70                  75                  80
Val Ser Ala Thr Phe Trp Gln Asn Pro Arg Asn His Phe Arg Cys Gln
                85                  90                  95
Val Gln Phe Tyr Gly Leu Ser Glu Asn Asp Glu Trp Thr Gln Asp Arg
            100                 105                 110
Ala Lys Pro Val Thr Gln Ile Val Ser Ala Glu Ala Trp Gly Arg Ala
        115                 120                 125
Asp Cys Gly Phe Thr Ser Glu Ser Tyr Gln Gln Gly Val Leu Ser Ala
    130                 135                 140
Thr Ile Leu Tyr Glu Ile Leu Leu Gly Lys Ala Thr Leu Tyr Ala Val
145                 150                 155                 160
Leu Val Ser Ala Leu Val Leu Met Ala Met Val Lys Arg Lys Asp Ser
                165                 170                 175
Arg Gly
```

<210> SEQ ID NO 10
<211> LENGTH: 537
<212> TYPE: DNA
<213> ORGANISM: Homo sapiens

<400> SEQUENCE: 10

```
gacctgaaaa acgtgttccc acccgaggtc gctgtgtttg agccatcaga agcagagatc      60
tcccacaccc aaaaggccac actggtatgc ctggccacag gcttctaccc cgaccacgtg     120
```

```
gagctgagct ggtgggtgaa tgggaaggag gtgcacagtg gggtcagcac agacccgcag    180
cccctcaagg agcagcccgc cctcaatgac tccagatact gcctgagcag ccgcctgagg    240
gtctcggcca ccttctggca gaaccccgc aaccacttcc gctgtcaagt ccagttctac    300
gggctctcgg agaatgacga gtggaccag gatagggcca aacccgtcac ccagatcgtc    360
agcgccgagg cctggggtag agcagactgt ggcttcacct ccgagtctta ccagcaaggg    420
gtcctgtctg ccaccatcct ctatgagatc ttgctaggga aggccacctt gtatgccgtg    480
ctggtcagtg ccctcgtgct gatggccatg gtcaagagaa aggattccag aggctag      537
```

<210> SEQ ID NO 11
<211> LENGTH: 173
<212> TYPE: PRT
<213> ORGANISM: Mus musculus
<400> SEQUENCE: 11

```
Glu Asp Leu Arg Asn Val Thr Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 12
<211> LENGTH: 522
<212> TYPE: DNA
<213> ORGANISM: Mus musculus
<400> SEQUENCE: 12

```
gaggatctga gaaatgtgac tccacccaag gtctccttgt ttgagccatc aaaagcagag    60
attgcaaaca acaaaaggc taccctcgtg tgcttggcca ggggcttctt ccctgaccac    120
gtggagctga gctggtgggt gaatggcaag gaggtccaca gtggggtcag cacggaccct    180
caggcctaca aggagagcaa ttatagctac tgcctgagca gccgcctgag ggtctctgct    240
accttctggc acaatcctcg caaccacttc cgctgccaag tgcagttcca tgggctttca    300
gaggaggaca gtggccaga gggctcaccc aaacctgtca cacagaacat cagtgcagag    360
gcctggggcc gagcagactg tgggattacc tcagcatcct atcaacaagg ggtcttgtct    420
gccaccatcc tctatgagat cctgctaggg aaagccaccc tgtatgctgt gcttgtcagt    480
```

```
acactggtgg tgatggctat ggtcaaaaga aagaattcat ga                      522
```

<210> SEQ ID NO 13
<211> LENGTH: 173
<212> TYPE: PRT
<213> ORGANISM: Mus musculus
<400> SEQUENCE: 13

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170
```

<210> SEQ ID NO 14
<211> LENGTH: 522
<212> TYPE: DNA
<213> ORGANISM: Mus musculus
<400> SEQUENCE: 14

```
gaggatctga gaaatgtgac tccacccaag gtctccttgt ttgagccatc aaaagcagag    60
attgcaaaca acaaaaggc taccctcgtg tgcttggcca ggggcttctt ccctgaccac    120
gtggagctga gctggtgggt gaatggcaag gaggtccaca gtggggtcag cacggaccct    180
caggcctaca aggagagcaa ttatagctac tgcctgagca gccgcctgag ggtctctgct    240
accttctggc acaatcctcg aaaccacttc cgctgccaag tgcagttcca tgggctttca    300
gaggaggaca agtggccaga gggctcaccc aaacctgtca cacagaacat cagtgcagag    360
gcctggggcc gagcagactg tggaatcact tcagcatcct atcatcaggg ggttctgtct    420
gcaaccatcc tctatgagat cctactgggg aaggccaccc tatatgctgt gctggtcagt    480
ggcctggtgc tgatggccat ggtcaagaaa aaaaattcct ga                      522
```

<210> SEQ ID NO 15
<211> LENGTH: 19
<212> TYPE: DNA
<213> ORGANISM: Artificial sequence
<220> FEATURE:
<223> OTHER INFORMATION: synthetic sequence
<400> SEQUENCE: 15
agatgtgtat aagagacag                                              19

<210> SEQ ID NO 16
<211> LENGTH: 19
<212> TYPE: DNA
<213> ORGANISM: Artificial sequence
<220> FEATURE:
<223> OTHER INFORMATION: synthetic sequence

<400> SEQUENCE: 16
ctgtctctta tacacatct                                              19

<210> SEQ ID NO 17
<211> LENGTH: 20
<212> TYPE: DNA
<213> ORGANISM: Artificial sequence
<220> FEATURE:
<223> OTHER INFORMATION: synthetic sequence

<400> SEQUENCE: 17
aatgatacgg cgaccaccga                                             20

<210> SEQ ID NO 18
<211> LENGTH: 24
<212> TYPE: DNA
<213> ORGANISM: Artificial sequence
<220> FEATURE:
<223> OTHER INFORMATION: synthetic sequence

<400> SEQUENCE: 18
caagcagaag acggcatacg agat                                        24

<210> SEQ ID NO 19
<211> LENGTH: 33
<212> TYPE: DNA
<213> ORGANISM: Artificial sequence
<220> FEATURE:
<223> OTHER INFORMATION: synthetic sequence

<400> SEQUENCE: 19
acactctttc cctacacgac gctcttccga tct                              33

<210> SEQ ID NO 20
<211> LENGTH: 34
<212> TYPE: DNA
<213> ORGANISM: Artificial sequence
<220> FEATURE:
<223> OTHER INFORMATION: synthetic sequence

<400> SEQUENCE: 20
gtgactggag ttcagacgtg tgctcttccg atct                             34

<210> SEQ ID NO 21
<211> LENGTH: 30
<212> TYPE: DNA
<213> ORGANISM: Artificial sequence
<220> FEATURE:
<223> OTHER INFORMATION: synthetic sequence

<400> SEQUENCE: 21
ccatctcatc cctgcgtgtc tccgactcag                                  30

<210> SEQ ID NO 22
<211> LENGTH: 23
<212> TYPE: DNA

```
<213> ORGANISM: Artificial sequence
<220> FEATURE:
<223> OTHER INFORMATION: synthetic sequence

<400> SEQUENCE: 22
cctctctatg ggcagtcggt gat                                             23
```